United States Patent
Dhugga et al.

(10) Patent No.: US 7,091,398 B2
(45) Date of Patent: Aug. 15, 2006

(54) ISOLATED SUCROSE SYTHASE POLYNUCLEOTIDES AND USES THEREOF

(75) Inventors: Kanwarpal S. Dhugga, Johnston, IA (US); Timothy G. Helentjaris, Ankeny, IA (US); Xiaomu Niu, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 267 days.

(21) Appl. No.: 10/080,114

(22) Filed: Feb. 21, 2002

(65) Prior Publication Data

US 2003/0005482 A1    Jan. 2, 2003

Related U.S. Application Data

(60) Provisional application No. 60/270,777, filed on Feb. 22, 2001.

(51) Int. Cl.
  C12N 15/09    (2006.01)
  C12N 15/29    (2006.01)
  C12N 15/82    (2006.01)
  A01H 5/00     (2006.01)
  A01H 5/10     (2006.01)

(52) U.S. Cl. .................. 800/278; 800/290; 800/298; 800/295; 800/317; 800/320; 435/468; 435/69.1; 536/23.2; 536/23.6

(58) Field of Classification Search .............. 800/278, 800/298, 295, 320, 317, 290; 435/468, 320.1, 435/430.1, 69.1; 536/23.2, 23.6, 24.5

See application file for complete search history.

(56) References Cited

U.S. PATENT DOCUMENTS

| | | | | |
|---|---|---|---|---|
| 5,716,837 | A * | 2/1998 | Barry et al. | 800/284 |
| 5,750,389 | A | 5/1998 | Elling et al. | 435/193 |
| 5,866,790 | A * | 2/1999 | Hesse et al. | 800/284 |
| 5,919,675 | A | 7/1999 | Adams et al. | 435/172.3 |
| 5,955,330 | A | 9/1999 | Vasil et al. | 435/172.3 |
| 5,994,628 | A | 11/1999 | Rodriguez | 800/298 |
| 6,118,047 | A | 9/2000 | Anderson et al. | 800/278 |
| 6,184,440 | B1 | 2/2001 | Shoseyov et al. | 800/290 |
| 6,222,098 | B1 | 4/2001 | Barry et al. | 800/284 |
| 6,331,660 | B1 | 12/2001 | Chomet et al. | 800/278 |
| 2001/0056583 | A1 | 12/2001 | McElroy et al. | 800/278 |
| 2003/0135870 | A1 * | 7/2003 | Cheikh et al. | 800/8 |

FOREIGN PATENT DOCUMENTS

| | | |
|---|---|---|
| WO | WO89/07647 | 8/1989 |
| WO | WO94/01571 | 1/1994 |
| WO | WO95/35027 | 12/1995 |
| WO | WO98/22604 | 5/1998 |
| WO | WO99/67404 | 12/1999 |
| WO | WO00/09706 | 2/2000 |
| WO | WO00/11144 | 3/2000 |
| WO | WO00/11200 | 3/2000 |
| WO | WO00/18930 | 4/2000 |
| WO | WO00/26371 | 5/2000 |
| WO | WO01/17333 | 3/2001 |

OTHER PUBLICATIONS

Bird et al, Biology and Genetic Review, vol. 9, pp. 207-227 (1991).*
Sandler et al. Plant Molecular Biology, vol. 11, pp. 301-310 (1988).*
Napoli et al. The Plant Cell, vol. 2, pp. 279-289, 1990.*
Huber et al. Plant Physiology, 112:793-802, 1996.*
Fu et al. The Plant Cell, vol. 7, pp. 1369-1385, (1995).*
Amor, et al., "A membrane-associated form of sucrose synthase and its potential role in synthesis of cellulose and callose in plants", *Proc. Natl. Acad. Sci. USA*, vol. 92, Sep. 1995, pp. 9353-9357.
Buckeridge, et al., "The mechanism of synthesis of a mixed-linkage (1->3), (1->4) β-D-glucan in maize. Evidence for multiple sites of glucosyl transfer in synthase complex", *Plant Physiology*, vol. 120, Aug. 1999, pp. 1105-1116.
Carlson, et al., "Evidence for plasma membrane-associated forms of sucrose synthase in maize", *Mol. Gen. Genet.*, 1996, pp. 303-310.
Chourey, et al., "Genetic evidence that the two isozymes of sucrose synthase present in developing maize endosperm are critical, one for cell wall integrity and the other for starch biosynthesis", *Mol. Gen. Genet.*, 1998, pp. 88-96.
DeVries, et al., "Products, requirements and efficiency of biosynthesis: A Quantitative approach", *J. Theor. Biol.*, 1974, pp. 339-377.
Huang, et al., "Complete nucleotide sequence of the maize (zea mays L.) sucrose synthase 2 cDNA", *Plant Physiol*, 1994, pp. 293-294.
Huber, et al., "Phosphorylation of serine-15 of maize leaf sucrose synthase", *Plant Physiol.*, 1996, pp. 793-802.
Kang, et al., "Metabolism of glucose-6-phosphate and utilization of multiple metabolites for fatty acid synthesis by plastids from developing oilseed rape embryos", *Planta*, 1996, pp. 321-327.
McCarty, et al., "The cloning, genetic mapping, and expression of the constitutive sucrose synthase locus of maize", *Proc. Natl. Acad. Sci. USA*, 1986, pp. 9099-9103.
Nakai, et al., "Enhancement of celluose production by expression of sucrose synthase in *acetobacter xylinum*", *Proc. Natl. Acad. Sci. USA*, vol. 96, Jan. 1999, pp. 14-18.
Sinclair, et al., "Photosynthate and nitrogen requirements for seed production by various crops", *Science*, 1975, pp. 565-567.
Sturm, et al., "Tissue-specific expression of two genes for sucrose synthase in carrot (dancus carota L.)", *Plant Molecular Biology*, 1999, pp. 349-360.

(Continued)

Primary Examiner—Medina A. Ibrahim
(74) Attorney, Agent, or Firm—Pioneer Hi-Bred International, Inc.; Kathryn K. Lappegard

(57) ABSTRACT

The invention provides a novel isolated sucrose synthase nucleic acid and its encoded protein. The present invention also provides methods and compositions relating to altering sucrose synthase levels in plants, and in particular, in plant stalks and/or plant seeds. The invention further provides recombinant expression cassettes, host cells, transgenic plants, and transgenic seeds.

8 Claims, 17 Drawing Sheets

OTHER PUBLICATIONS

Tang, et al., "Antisense repression of sucrose synthase in carrot (daucus carota L.) affects growth rather than sucrose partitioning", *Plant Molecular Biology*, 1999, pp. 465-479.

Werr, et al., "Structure of the sucrose synthase gene on chromosome 9 of Zea mays L.", *The EMBO Journal*, 1985, pp. 1373-1380.

Winter, et al., "Membrane association of sucrose synthase: changes during the graviresponse and possible control by protein phosphorylation", *FEBS Letters*, 1997, pp. 151-155.

Wu, et al., "Genomic cloning of 18kDa oleosin and detection of triacylglycerols and oleosin isoforms in maturing rice and postgerminative seedlings", *J. Biochem.*, 1986, pp. 386-391.

* cited by examiner

Allele 1: CACCCGG-mu-AGATTG

Allele 2: CACC-mu-CGGAGATTG

| Genotype | structural dry matter (% of total dry matter) | cellulose (% of total dry matter) | cellulose (% of structural dry matter) |
|---|---|---|---|
| Sus-1 (WT) | 63.2 | 25.2 +/-0.38 | 39.9 |
| sus-1 (mutant) | 47.3 | 17.7 +/-0.34 | 37.4 |

Figure 7.

```
                    1                                                  50
Sh1         (1)     -----MAAKLTRLHSLRERLGATFSSHPNELIALFSRYVHQGKGMLQRHQ
Sus1        (1)     MGEGAGDRVLSRLHSVRERIGDSLSAHPNELVAVFTRLKNLGKGMLQPHQ
Sus3        (1)     ----------STHASGDRVEDTLHAHRNELVALLSKYVNKGKGILQPHH
Consensus   (1)              LSRLHSLRERIGDTLSAHPNELVALFSRYVN GKGMLQPHQ
                    51                                                 100
Sh1         (46)    LLAEFD-ALFDSDKE--KYAPFEDILRAAQEAIVLPPWVALAIRPRPGVW
Sus1        (51)    ILAEYNNAIPEAEREKLKDGAFEDVLRAAQEAIVIPPWVALAIRPRPGVW
Sus3        (40)    ILDALDEVQGSGGRA-LAEGPFLDVLRSAQEAIVLPPFVAIAVRPRPGVW
Consensus   (51)    ILAEFD AI DADRE LKDGPFEDVLRAAQEAIVLPPWVALAIRPRPGVW
                    101                                                150
Sh1         (93)    DYIRVNVSELAVEELSVSEYLAFKEQLVDGQSNSNFVLELDFEPFNASFP
Sus1        (101)   EYVRVNVSELAVEELRVPEYLQFKEQLVEEGPNNNFVLELDFEPFNASFP
Sus3        (89)    EYVRVNVHELSVEQLTVSEYLRFKEELVDGQHNDPYVLELDFEPFNVSVP
Consensus   (101)   EYVRVNVSELAVEELSVSEYL FKEQLVDGQ N NFVLELDFEPFNASFP
                    151                                                200
Sh1         (143)   RPSMSKSIGNGVQFLNRHLSSKLFQDKESLYPLLNFLKAHNYKGTTMMLN
Sus1        (151)   RPSLSKSIGNGVQFLNRHLSSKLFHDKESMYPLLNFLRAHNYKGMTMMLN
Sus3        (139)   RPNRSSIGNGVQFLNRHLSSIMFRNRDCLEPLLDFLRGHRHKGHVMMLN
Consensus   (151)   RPSLSKSIGNGVQFLNRHLSSKLF DKESLYPLLNFLRAHNYKG TMMLN
                    201                                                250
Sh1         (193)   DRIQSLRGLQSSLRKAEEYLLSVPQDTPYSEFNHRFQELGLEKGWGDTAK
Sus1        (201)   DRIRSLSALQGALRKAEEHLSTLQADTPYSEFHHRFQELGLEKGWGDCAK
Sus3        (189)   DRIQSLGRLQSVLTKAEEHLSKLPADTPYSQFAYKFQEWGLEKGWGDTAG
Consensus   (201)   DRIQSL ALQSALRKAEEHLSSLPADTPYSEF HRFQELGLEKGWGDTAK
                    251                                                300
Sh1         (243)   RVLDTLHLLLDLLEAPDPANLEKFLGTIPMMFNVVILSPHGYFAQSNVLG
Sus1        (251)   RAQETIHLLLDLLEAPDPSTLEKFLGTIPMVFNVVILSPHGYFAQANVLG
Sus3        (239)   HVLEMIHLLLDIIQAPDPSTLEKFLGRIPMIFNVVVVSPHGYFGQANVLG
Consensus   (251)   RVLETIHLLLDLLEAPDPSTLEKFLGTIPMIFNVVILSPHGYFAQANVLG
                    301                                                350
Sh1         (293)   YPDTGGQVVYILDQVRALENEMLLRIKQQGLDITPKILIVTRLLPDAAGT
Sus1        (301)   YPDTGGQVVYILDQVRAMENEMLLRIKQCGLDITPKILIVTRLLPDATGT
Sus3        (289)   LPDTGGQIVYILDQVRALENEMVLRLKQGLDVSPKILIVTRLIPDAKGT
Consensus   (301)   YPDTGGQVVYILDQVRALENEMLLRIKQQGLDITPKILIVTRLLPDA GT
                    351                                                400
Sh1         (343)   TCGQRLEKVIGTEHTDIIRVPFRNENGILRKWISRFDVWPYLETYTEDVS
Sus1        (351)   TCGQRLEKVLGTEHCHILRVPFRTENGIVRKWISRFEVWPYLETYTDDVA
Sus3        (339)   SCNQRLERISGTQHTYILRVPFRNENGILKKWISRFDVWPYLETFAEDAA
Consensus   (351)   TCGQRLEKVIGTEHTHILRVPFRNENGILRKWISRFDVWPYLETYTEDVA
                    401                                                450
Sh1         (393)   SEIMKEMQAKPDLIIGNYSDGNLVATLLAHKLGVTQCTIAHALEKTKYPN
Sus1        (401)   HEIAGELQANPDLIIGNYSDGNLVACLLAHKMGVTHCTIAHALEKTKYPN
Sus3        (389)   GEIAAELQGTPDFIIGNYSDGNLVASLLSYKMGITQCNIAHALEKTKYPD
Consensus   (401)    EIAAELQA PDLIIGNYSDGNLVASLLAHKMGVTQCTIAHALEKTKYPN
                    451                                                500
Sh1         (443)   SDIYLDKFDSQYHFSCQFTADLIAMNHTDFIITSTFQEIAGSKDTVGQYE
Sus1        (451)   SDLYWKKFEDHYHFSCQFTTDLIAMNHADFIITSTFQEIAGNKDTVGQYE
Sus3        (439)   SDIFWKNFDEKYHFSCQFTADIIAMNNADFIITSTYQEIAGSKNTVGQYE
Consensus   (451)   SDIYWKKFDD YHFSCQFTADLIAMNHADFIITSTFQEIAGSKDTVGQYE
                    501                                                550
Sh1         (493)   SHIAFTLPGLYRVVHGIDVFDPKFNIVSPGADMSVYYPYTETDKRLTAFH
Sus1        (501)   SHMAFTMPGLYRVVHGIDVFDPKFNIVSPGADLSIYFPYTESHKRLTSLH
Sus3        (489)   SHTAFTLPGLYRVVHGIDVFDPKFNIVSPGADMSIYFPHTEKAKRLTSLH
Consensus   (501)   SHIAFTLPGLYRVVHGIDVFDPKFNIVSPGADMSIYFPYTES KRLTSLH
```

Figure 8a

```
              551                                                600
Sh1       (543) PEIEELIYSDVENSEHKFVLKDKKKPIIFSMARLDRVKNMTGLVEMYGKN
Sus1      (551) PEIEELLYSQTENTEHKFVLNDRNKPIIFSMARLDRVKNLTGLVELYGRN
Sus3      (539) GSIENLIYDPEQNDEHIGHLDDRSKPILFSMARLDRVKNITGLVEAFAKC
Consensus (551) PEIEELIYS ENSEHKFVL DR KPIIFSMARLDRVKNITGLVELYGKN
              601                                                650
Sh1       (593) ARLRELANLVIVAGDHGK-ESKDREEQAEFKKMYSLIDEYKLKGHIRWIS
Sus1      (601) KRLQELVNLVVVCGDHGN-PSKDKEEQAEFKKMFDLIEQYNLNGHIRWIS
Sus3      (589) AKLRELVNLVVVAGYNDVNKSKDREEIAEIEKMHELIKTHNLFGQFRWIS
Consensus (601) ARLRELVNLVVVAGDHG   SKDREEQAEFKKMHDLID YNL GHIRWIS
              651                                                700
Sh1       (642) AQMNRVRNGELYRYICDTKGAFVQPAFYEAFGLTVIESMTCGLPTIATCH
Sus1      (650) AQMNRVRNGELYRYICDTKGAFVQPAFYEAFGLTVVEAMTCGLPTFATAY
Sus3      (639) AQTNRARNGELYRYIADTHGAFVQPALYEAFGLTVVEAMTCGLPTFATLH
Consensus (651) AQMNRVRNGELYRYICDTKGAFVQPAFYEAFGLTVVEAMTCGLPTFAT H
              701                                                750
Sh1       (692) GGPAEIIVDGVSGLHIDPYHSDKAADILVNFFDKCKADPSYWDEISQGGL
Sus1      (700) GGPAEIIVHGVSGYHIDPYQGDKASALLVDFFDKCQAEPSHWSKISQGGL
Sus3      (689) GGPAEIIEHGVSGFHIDPYHPEQAVNLMADFFDRCKQDPDHWVNISGAGL
Consensus (701) GGPAEIIVHGVSGFHIDPYH DKAA LLVDFFDKCKADPSHW   ISQGGL
              751                                                800
Sh1       (742) QRIYEKYTWKLYSERLMTLTGVYGFWKYVSNLERRETRRYIEMFYALKYR
Sus1      (750) QRIEEKYTWKLYSERLMTLTGVYGFWKYVSNLERRETRRYLEMLYALKYR
Sus3      (739) QRIYEKYTWKIYSERLMTLAGVYGFWKYVSKLERLETRRYLEMFYILKFR
Consensus (751) QRIYEKYTWKLYSERLMTLTGVYGFWKYVSNLERRETRRYLEMFYALKYR
              801       817
Sh1       (792) SLASQVPLSFD------
Sus1      (800) TMASTVPLAVEGEPSSK
Sus3      (789) ELAKTVPLAID-QPQ--
Consensus (801) SLASTVPLAID  P
```

Figure 8b

```
               1                                                  50
Sh1       (1)  AAACCCTCCCTCCCTCCTCCATTGGACTGCTTGCTCCCTGTTGACCATTG
Sus1      (1)  ----------------------GCCTGAG-GATCCAGGAAGAGGACAG
Sus3      (1)  --------------------------------------------------
Consensus (1)                         G CTG   G TCC  G  GA  A  G
               51                                                100
Sh1      (51)  GGTATTCTGAACCATCGAGCCATGGCTGCCAAGCTGACTCGCCTTCACAG
Sus1     (26)  CA-ATGGGGGAAGGTGCAGGTGACCGTGTC---CTGAGCCGCCTCCACAG
Sus3      (1)  ------------------------------------GTCGAC-CCACGC
Consensus(51)      AT    G A   T  AG        TG C    CTGAGTCGCCTCCACAG
               101                                               150
Sh1     (101)  TCTTCGCGAACGCCTTGGTGCCACCTTCTCCTCCCATCCCAATGAACTGA
Sus1     (72)  CGTCAGGGAGCGCATTGGCGACTCACTCTCTGCCCACCCCAATGAGCTTG
Sus3     (13)  GTCCGGCGACCGCGTCGAGGACACCCTCCACGCGCACCGCAACGAGCTCG
Consensus(101)    TC GCGA CGC TTGG GACACCCTCTCCGCCCACCCCAATGAGCT G
               151                                               200
Sh1     (151)  TAGCACTCTTTTCCAGGTATGTTCACCAGGGCAAGGGAATGCTTCAGCGC
Sus1    (122)  TCGCCGTCTTCACCAGGCTGAAAAACCTTGGAAAGGGTATGCTGCAGCCC
Sus3     (63)  TCGCCCTCCTGTCCAAGTACGTGAACAAGGGGAAGGGCATCCTGCAGCCG
Consensus(151)  TCGCCCTCTT TCCAGGTA GT AACCAGGG AAGGG ATGCTGCAGCCC
               201                                               250
Sh1     (201)  CATCAGCTGCTTGCGGAGTTTGA---TGC----CCTGTT--TGATAGTGA
Sus1    (172)  CACCAGATCATTGCCGAGTACAACAATGCGATCCCTGAGGCTGAGCGCGA
Sus3    (113)  CACCACATCCTCGACGCGCTCGACGAGGT----CCAGGG-CTCCGGGGGC
Consensus(201) CACCAGATCCTTGCCGAGTTCGAC ATGC    CCTG G CTGAG G GA
               251                                               300
Sh1     (242)  CAAGGAGAAG--TATGCACCATTTGAAGACATTCTTCGTGCTGCTCAGGA
Sus1    (222)  GAAGCTCAAG--GATGGTGCTTTTGAGGATGTCCTGAGGGCAGCTCAGGA
Sus3    (158)  CGCGCGCTAGCCGAGGGACCCTTCCTCGACGTCCTCCGCTCCGCGCAGGA
Consensus(251) CAAGC CAAG   GATGGACC TTTGA GACGTCCT CG GC GCTCAGGA
               301                                               350
Sh1     (290)  AGCAATTGTGCTCCCCCCATGGGTTGCACTTGCTATCAGGCCAAGGCCTG
Sus1    (270)  GGCGATTGTCATCCCCCCATGGGTTGCACTTGCCATCCGCCCTAGGCCTG
Sus3    (208)  GGCGATCGTGCTGCCGCCGTTCGTGGCCATCGCGGTGCGCCCGCGCCCGG
Consensus(301) GGCGATTGTGCTCCCCCCATGGGTTGCACTTGC ATCCGCCC AGGCCTG
               351                                               400
Sh1     (340)  GTGTCTGGGATTACATTCGGGTGAATGTAAGTGAGCTGGCTGTGGAGGAG
Sus1    (320)  GTGTCTGGGAGTATGTGAGGGTCAACGTCAGTGAGCTCGCTGTTGAGGAG
Sus3    (258)  GAGTTTGGGAGTACGTCCGCGTCAACGTTCACGAGCTCAGCGTCGAGCAG
Consensus(351) GTGTCTGGGAGTACGT CGGGTCAACGT AGTGAGCTCGCTGT GAGGAG
               401                                               450
Sh1     (390)  CTGAGTGTTTCTGAGTACTTGGCATTCAAGGAACAGCTGGTGGATGGACA
Sus1    (370)  CTGAGAGTTCCTGAGTACCTGCAGTTCAAGGAACAGCTTGTGGAAGAAGG
Sus3    (308)  CTCACAGTCTCGGAGTACCTCCGCTTCAAGGAGGAGCTTGTCGACGGCCA
Consensus(401) CTGAGAGTTTCTGAGTACCTGC  TTCAAGGAACAGCTTGTGGA GGACA
               451                                               500
Sh1     (440)  ATCCAACAGCAACTTTGTGCTTGAGCTTGATTTTGAGCCCTTCAATGCCT
Sus1    (420)  CCCCAACAACAACTTTGTTCTTGAGCTGGACTTTGAGCCATTCAATGCCT
Sus3    (358)  GCACAATGATCCCTACGTTCTCGAGCTTGACTTCGAGCCGTTCAATGTCT
Consensus(451)  CCCAACAACAACTTTGTTCTTGAGCTTGACTTTGAGCC TTCAATGCCT
               501                                               550
Sh1     (490)  CCTTTCCTCGTCCTTCCATGTCGAAGTCCATCGGAAATGGAGTGCAATTC
Sus1    (470)  CCTTCCCCCGTCCTTCTCTGTCAAAGTCCATTGGCAATGGCGTGCAGTTC
Sus3    (408)  CAGTCCCACGCCCAAATCGGTCATCATCTATTGGAAACGGTGTGCAGTTC
Consensus(501) CCTTCCC CGTCCTTCTCTGTCAAAGTCCATTGGAAATGG GTGCAGTTC
```

Figure 9a

```
                    551                                                600
Sh1       (540) CTTAACCGACACCTGTCGTCCAAGTTGTTCCAGGACAAGGAGAGTTTGTA
Sus1      (520) CTCAACAGGCACCTGTCATCAAAGCTCTTCCATGACAAGGAGAGCATGTA
Sus3      (458) CTCAACCGACACTTGTCCTCAATCATGTTCCGCAACAGGGATTGCTTGGA
Consensus (551) CTCAACCGACACCTGTC TCAAAG TGTTCCA GACAAGGAGAGCTTGTA
                    601                                                650
Sh1       (590) CCCCTTGCTGAACTTCCTCAAGGCTCATAACTACAAGGGCACGACGATGA
Sus1      (570) CCCCTTGCTCAACTTCCTTCGCGCCCACAACTACAAGGGGATGACCATGA
Sus3      (508) GCCCCTGTTGGATTTCCTCCGTGGCCACCGGCACAAGGGGCATGTTATGA
Consensus (601) CCCCTTGCTGAACTTCCTCCG GCCCACAACTACAAGGGGA GAC ATGA
                    651                                                700
Sh1       (640) TGTTGAATGACAGAATCCAAAGCCTTCGTGGTCTCCAATCATCCCTGAGA
Sus1      (620) TGTTGAACGACAGAATCCGCAGTCTCAGTGCTCTGCAAGGTGCGCTGAGG
Sus3      (558) TGCTTAATGATAGAATACAAAGCTTGGGGAGGCTTCAGTCTGTGCTGACC
Consensus (651) TGTTGAATGACAGAATCCAAAGCCT GTGGTCT CAATCTGCGCTGAG
                    701                                                750
Sh1       (690) AAGGCAGAGGAGTATCTACTGAGTGTTCCTCAAGACACTCCCTACTCGGA
Sus1      (670) AAGGCTGAGGAGCACCTGTCCACCCTACAAGCTGATACCCCATACTCTGA
Sus3      (608) AAAGCTGAGGAGCACTTGTCAAAGCTCCCTGCTGACACACCATACTCACA
Consensus (701) AAGGCTGAGGAGCACCTGTC A  CT CCTGCTGACAC CCATACTC GA
                    751                                                800
Sh1       (740) GTTCAACCATAGGTTCCAAGAGCTTGGCTTGGAGAAGGGTTGGGGTGACA
Sus1      (720) ATTTCACCACAGGTTCCAGGAACTTGGTCTGGGAGAAGGGTTGGGGTGATT
Sus3      (658) ATTTGCTTATAAATTTCAAGAGTGGGGCCTGGAGAAAGGTTGGGGTGATA
Consensus (751) ATTT ACCATAGGTTCCAAGAGCTTGGCCTGGAGAAGGGTTGGGGTGATA
                    801                                                850
Sh1       (790) CTGCGAAGCGTGTTCTCGACACACTCCACTTGCTTCTCGACCTTCTTGAG
Sus1      (770) GCGCTAAGCGTGCACAGGAGACTATCCACCTCCTCTTGGACCTCCTGGAG
Sus3      (708) CAGCAGGACATGTTTTGGAAATGATCCATCTCCTTCTAGACATCATTCAG
Consensus (801) C GC AAGCGTGTTCTGGA AC ATCCACCTCCTTCT GACCTCCTTGAG
                    851                                                900
Sh1       (840) GCCCCTGATCCTGCCAACTTGGAGAAGTTCCTTGGAACTATACCAATGAT
Sus1      (820) GCCCCAGATCCGTCCACCCTGGAGAAGTTCCTTGGAACGATCCCCATGGT
Sus3      (758) GCGCCAGACCCATCTACCCTAGAGAAATTCTTGGGGAGGATCCCCATGAT
Consensus (851) GCCCCAGATCC TCCACCCTGGAGAAGTTCCTTGGAACGATCCCCATGAT
                    901                                                950
Sh1       (890) GTTCAACGTTGTTATCCTGTCTCCTCATGGCTACTTCGCCCAGTCCAATG
Sus1      (870) GTTCAATGTCGTTATCCTCTCCCTCATGGTTACTTCGCTCAAGCTAATG
Sus3      (808) TTTTAACGTTGTTGTGGTATCCCCTCATGGATACTTTGGTCAAGCTAATG
Consensus (901) GTTCAACGTTGTTATCCT TCCCCTCATGG TACTTCGCTCAAGCTAATG
                    951                                               1000
Sh1       (940) TGCTTGGATACCCTGACACTGGCGGTCAGGTTGTGTACATTCTGGATCAA
Sus1      (920) TCTTGGGTTACCCTGACACCGGAGGCCAGGTTGTCTACATCTTGGATCAA
Sus3      (858) TATTAGGCTTGCCAGACACAGGAGGACAGATCGTCTATATACTGGACCAA
Consensus (951) T TT GG TACCCTGACAC GGAGG CAGGTTGTCTACAT CTGGATCAA
                   1001                                               1050
Sh1       (990) GTCCGTGCTTTGGAGAATGAGATGCTTCTGAGGATTAAGCAGCAAGGCCT
Sus1      (970) GTGCGCGCTATGGAGAACGAAATGCTGCTGAGGATCAAGCAGTGTGGTCT
Sus3      (908) GTCCGTGCACTAGAAAATGAGATGGTTCTCCGTTTAAAGAAACAAGGGCT
Consensus (1001) GTCCGTGCT TGGAGAATGAGATGCTTCTGAGGAT AAGCAGCAAGG CT
```

Figure 9b

```
                       1051                                              1100
        Sh1   (1040)   TGATATCACTCCGAAGATCCTCATTGTTACCAGGCTGTTGCCTGATGCTG
        Sus1  (1020)   TGACATCACGCCGAAGATCCTTATTGTCACCAGGTTGCTCCCTGATGCAA
        Sus3   (958)   TGATGTTTCCCCAAAGATTCTCATTGTTACTCGGCTGATACCAGATGCAA
   Consensus  (1051)   TGATATCAC CCGAAGATCCTCATTGTTACCAGGCTG T CCTGATGCAA 1101                                              1150
        Sh1   (1090)   CTGGGACTACGTGCGGTCAGCGGCTGGAGAAGGTCATTGGTACTGAGCAC
        Sus1  (1070)   CTGGCACCACCTGTGGCCAGCGCCTTGAGAAGGTCCTTGGCACCGAGCAC
        Sus3  (1008)   AAGGAACATCATGCAATCAGCGGCTTGAGAGAATTAGTGGAACACAGCAT
   Consensus  (1101)   CTGG AC AC TGCGGTCAGCGGCTTGAGAAGGTCATTGG AC GAGCAC
                       1151                                              1200
        Sh1   (1140)   ACAGACATCATTCGCGTTCCCTTCAGAAATGAGAATGGCATCCTCCGCAA
        Sus1  (1120)   TGCCATATCCTTCGCGTGCCATTCAGAACAGAAAACGGAATCGTTCGCAA
        Sus3  (1058)   ACTTACATATTACGAGTTCCCTTCAGAAATGAAAATGGATACTTAAGAA
   Consensus  (1151)   AC  ACATC TTCGCGTTCCCTTCAGAAATGAAAATGG ATCCTTCGCAA
                       1201                                              1250
        Sh1   (1190)   GTGGATCTCTCGTTTTGATGTCTGGCCATACCTGGAGACATACACTGAGG
        Sus1  (1170)   GTGGATCTCGCGATTTGAAGTCTGGCCGTACCTGGAGACTTACACTGATG
        Sus3  (1108)   ATGGATATCAAGATTTGATGTGTGGCCATATCTGGAAACATTTGCTGAGG
   Consensus  (1201)   GTGGATCTC CGATTTGATGTCTGGCCATACCTGGAGACATACACTGAGG
                       1251                                              1300
        Sh1   (1240)   ATGTTTCCAGTGAAATAATGAAAGAAATGCAGGCCAAGCCTGACCTTATC
        Sus1  (1220)   ACGTGGCGCATGAGATTGCTGGAGAGCTTCAGGCCAATCCTGACCTGATC
        Sus3  (1158)   ATGCTGCTGGTGAAATTGCTGCTGAATTACAAGGTACTCCAGACTTCATA
   Consensus  (1251)   ATGTTGC  GTGAAATTGCTG AGAA T CAGGCCAATCCTGACCT ATC
                       1301                                              1350
        Sh1   (1290)   ATTGGCAACTACAGCGATGGCAACCTAGTCGCCACTCTGCTCGCGCACAA
        Sus1  (1270)   ATCGGAAACTACAGTGACGGAAACCTTGTTGCGTGTTTGCTCGCCCACAA
        Sus3  (1208)   ATTGGAAACTACAGTGATGGAAATCTTGTGGCGTCATTGCTATCTTACAA
   Consensus  (1301)   ATTGGAAACTACAGTGATGGAAACCTTGT GCGTCTTTGCTCGC CACAA
                       1351                                              1400
        Sh1   (1340)   GTTGGGAGTCACTCAGTGTACCATCGCTCATGCCTTGGAGAAAACCAAAT
        Sus1  (1320)   GATGGGTGTTACTCACTGTACCATTGCCCATGCGCTTGAGAAAACTAAGT
        Sus3  (1258)   GATGGGAATTACCCAGTGCAACATTGCTCATGCTCTGGAAAAGACTAAGT
   Consensus  (1351)   GATGGGAGTTACTCAGTGTACCATTGCTCATGC CTGGAGAAAACTAAGT
                       1401                                              1450
        Sh1   (1390)   ACCCCAACTCGGACATCTACTTGGACAAATTCGACAGCCAGTACCACTTC
        Sus1  (1370)   ACCCTAACTCCGACCTCTACTGGAAGAAGTTTGAGGATCACTACCACTTC
        Sus3  (1308)   ATCCAGATTCAGACATATTTTGGAAGAATTTCGATGAGAAGTACCATTTC
   Consensus  (1401)   ACCC AACTC GACATCTACTGGAAGAA TTCGA GA CAGTACCACTTC
                       1451                                              1500
        Sh1   (1440)   TCTTGCCAGTTCACAGCTGACCTTATTGCCATGAACCACACCGATTTCAT
        Sus1  (1420)   TCGTGCCAGTTCACCACTGACTTGATTGCAATGAACCATGCCGACTTCAT
        Sus3  (1358)   TCCTGCCAGTTCACTGCTGATATAATTGCTATGAACAATGCTGATTTTAT
   Consensus  (1451)   TC TGCCAGTTCAC GCTGAC T ATTGC ATGAACCATGCCGATTTCAT
                       1501                                              1550
        Sh1   (1490)   CATCACCAGCACATTCCAAGAAATCGCGGGAAGCAAGGACACCGTGGGGC
        Sus1  (1470)   CATCACCAGTACCTTCCAAGAGATCGCCGGAAACAAGGACACCGTCGGCC
        Sus3  (1408)   CATCACCAGCACATACCAAGAAATTGCTGGAAGCAAAAATACTGTTGGAC
   Consensus  (1501)   CATCACCAGCACATTCCAAGAAATCGC GGAAGCAAGGACACCGT GG C
```

Figure 9c

```
                 1551                                          1600
Sh1     (1540)   AGTACGAGTCCCATATCGCGTTCACTCTTCCTGGGCTCTACCGTGTCGTC
Sus1    (1520)   AGTACGAGTCACACATGGCGTTCACAATGCCTGGCCTGTACCGCGTTGTC
Sus3    (1458)   AGTATGAGAGTCATACTGCCTTTACTCTGCCTGGTCTGTACCGAGTTGTC
Consensus(1551)  AGTACGAGTC CATAT GCGTTCACTCTGCCTGG CTGTACCG GTTGTC
                 1601                                          1650
Sh1     (1590)   CATGGCATCGATGTTTTCGATCCCAAGTTCAACATTGTCTCTCCTGGAGC
Sus1    (1570)   CACGGCATTGATGTGTTCGACCCCAAGTTCAACATCGTGTCTCCTGGCGC
Sus3    (1508)   CATGGGATCGATGTCTTCGATCCAAAGTTCAATATAGTCTCTCCTGGAGC
Consensus(1601)  CATGGCATCGATGT TTCGATCCCAAGTTCAACAT GTCTCTCCTGGAGC
                 1651                                          1700
Sh1     (1640)   AGACATGAGTGTTTACTACCCTTATACGGAAACCGACAAGAGACTCACTG
Sus1    (1620)   GGACCTGTCCATCTACTTCCCGTACACCGAGTCGCACAAGAGGCTGACCT
Sus3    (1558)   TGACATGTCCATATACTTTCCACATACCGAGAAGGCCAAGCGACTCACCT
Consensus(1651)   GACATGTCCAT TACTTCCC TATACCGAGACGGACAAGAGACTCACCT
                 1701                                          1750
Sh1     (1690)   CCTTCCATCCTGAAATCGAGGAGCTCATCTACAGCGACGTCGAGAACTCC
Sus1    (1670)   CCCTTCACCCGGAGATTGAGGAGCTCCTGTACAGCCAAACCGAGAACACG
Sus3    (1608)   CTCTTCATGGTTCAATCGAAAATTTGATTTATGACCCGGAGCAAAACGAT
Consensus(1701)  CCCTTCATCCTGAAATCGAGGAGCTCAT TACAGCCA G CGAGAAC C
                 1751                                          1800
Sh1     (1740)   GAGCACAAGTTCGTGCTGAAGGACAAGAAGAAGCCGATCATCTTCTCGAT
Sus1    (1720)   GAGCACAAGTTCGTTCTGAACGACAGGAACAAGCCAATCATCTTCTCCAT
Sus3    (1658)   GAACACATTGGGCATCTGGATGACCGGTCAAAGCCCATCCTCTTCTCCAT
Consensus(1751)  GAGCACAAGTTCGTTCTGAA GACAGGAA AAGCC ATCATCTTCTCCAT
                 1801                                          1850
Sh1     (1790)   GGCGCGTCTCGACCGCGTGAAGAACATGACAGGCCTGGTCGAGATGTACG
Sus1    (1770)   GGCTCGTCTCGACCGTGTGAAGAACTTGACTGGGCTGGTGGAGCTGTACG
Sus3    (1708)   GGCAAGACTCGACAGGGTGAAGAACATAACAGGGCTGGTCGAAGCTTTTG
Consensus(1801)  GGC CGTCTCGACCG GTGAAGAACATGACAGGGCTGGTCGAG TGTACG
                 1851                                          1900
Sh1     (1840)   GCAAGAACGCGCGCCTGAGGGAGCTGGCGAACCTCGTGATCGTTGCCGGT
Sus1    (1820)   GCCGGAACAAGCGGCTGCAGGAGCTGGTGAACCTCGTGGTCGTCTGCGGC
Sus3    (1758)   CTAAGTGCGCTAAGCTGAGGGAGCTGGTAAACCTTGTCGTCGTTGCCGGG
Consensus(1851)  GCAAGAACGCGCGGCTGAGGGAGCTGGTGAACCTCGTGGTCGTTGCCGG
                 1901                                          1950
Sh1     (1890)   GACCACGG---CAAGGAGTCCAAGGACAGGGAGGAGCAGGCGGAGTTCAA
Sus1    (1870)   GACCATGG---CAACCCTTCCAAGGACAAGGAGGAGCAGGCCGAGTTCAA
Sus3    (1808)   TACAATGATGTCAACAAGTCCAAGGACAGGGAAGAGATCGCGGAGATAGA
Consensus(1901)  GACCATGG   CAAC AGTCCAAGGACAGGGAGGAGCAGGCGGAGTTCAA
                 1951                                          2000
Sh1     (1937)   GAAGATGTACAGCCTCATCGACGAGTACAAGTTGAAGGGCCATATCCGGT
Sus1    (1917)   GAAGATGTTTGACCTCATCGAGCAGTACAACCTGAACGGGCACATCCGCT
Sus3    (1858)   GAAGATGCATGAACTCATCAAGACCCACAACTTGTTCGGGCAGTTCCGCT
Consensus(1951)  GAAGATGTATGACCTCATCGAG AGTACAACTTGAACGGGCA ATCCGCT
                 2001                                          2050
Sh1     (1987)   GGATCTCGGCGCAGATGAACCGTGTCCGCAACGGGGAGCTGTACCGCTAC
Sus1    (1967)   GGATCTCCGCCCAGATGAACCGCGTCCGCAACGGCGAGCTGTACCGCTAC
Sus3    (1908)   GGATCTCTGCCCAGACAAACAGGGCCCGTAACGGCGAGCTCTATCGCTAC
Consensus(2001)  GGATCTC GCCCAGATGAACCG GTCCGCAACGGCGAGCTGTACCGCTAC
                 2051                                          2100
Sh1     (2037)   ATTTGCGATACCAAGGGCGCATTCGTGCAGCCTGCGTTCTACGAAGCGTT
Sus1    (2017)   ATCTGCGACACCAAGGGCGCCTTCGTGCAGCCTGCTTTCTACGAGGCTTT
Sus3    (1958)   ATCGCTGATACCCATGGTGCTTTCGTACAGCCGGCCTTGTATGAAGCGTT
Consensus(2051)  ATCTGCGATACCAAGGGCGC TTCGTGCAGCCTGC TTCTACGAAGCGTT
```

Figure 9d

```
              2101                                              2150
Sh1    (2087) CGGCCTGACTGTGATCGAGTCCATGACGTGCGGTCTGCCAACGATCGCGA
Sus1   (2067) CGGGCTGACGGTGGTTGAGGCCATGACCTGCGGCCTGCCCACGTTCGCCA
Sus3   (2008) CGGTCTCACCGTCGTTGAGGCCATGACCTGTGGGCTTCCTACTTTCGCGA
Consensus (2101) CGG CTGAC GTGGTTGAGGCCATGACCTGCGG CTGCC ACGTTCGCGA
              2151                                              2200
Sh1    (2137) CCTGCCATGGCGGCCCTGCTGAGATCATCGTGGACGGGGTATCTGGCCTG
Sus1   (2117) CCGCCTACGGCGGTCCGGCCGAGATCATCGTGCACGGCGTGTCTGGCTAC
Sus3   (2058) CGCTCCATGGAGGTCCAGCTGAGATCATAGAGCATGGCGTCTCGGGCTTC
Consensus (2151) CC  CCATGGCGGTCC GCTGAGATCATCGTGCACGGCGT TCTGGCTTC
              2201                                              2250
Sh1    (2187) CACATTGACCCTTACCACAGCGACAAGGCCGCGGATATCCTGGTCAACTT
Sus1   (2167) CACATCGACCCTTACCAGGGCGACAAGGCGTCGGCCCTGCTCGTGGACTT
Sus3   (2108) CACATTGACCCGTACCACCCCGAACAGGCTGTTAATCTGATGGCCGACTT
Consensus (2201) CACATTGACCCTTACCAC GCGACAAGGC GCGGATCTGCTGGTCGACTT
              2251                                              2300
Sh1    (2237) CTTTGACAAATGCAAGGCAGATCCGAGCTACTGGGACGAGATCTCACAGG
Sus1   (2217) CTTCGACAAGTGCAGGCGGAGCCGAGCCACTGGAGCAAGATCTCCCAGG
Sus3   (2158) CTTCGACCGGTGCAAGCAAGACCCAGATCACTGGGTGAATATATCTGGAG
Consensus (2251) CTTCGACAAGTGCAAGGCAGA CCGAGCCACTGGG CAAGATCTC CAGG
              2301                                              2350
Sh1    (2287) GCGGCCTGCAGAGAATTTATGAGAAGTACACCTGGAAGCTCTACTCCGAG
Sus1   (2267) GCGGGCTCCAGCGTATCGAGGAGAAGTACACCTGGAAGCTGTACTCGGAG
Sus3   (2208) CAGGGCTGCAGCGCATATACGAGAAGTACACATGGAAGATATACTCAGAG
Consensus (2301) GCGGGCTGCAGCG AT TA GAGAAGTACACCTGGAAGCT TACTC GAG
              2351                                              2400
Sh1    (2337) AGGCTGATGACCCTGACCGGCGTGTACGGGTTCTGGAAGTACGTGAGCAA
Sus1   (2317) AGGCTGATGACCCTCACCGGCGTGTACGGGTTCTGGAAGTACGTGTCCAA
Sus3   (2258) AGGTTGATGACACTGGCCGGGGTCTACGGTTTCTGGAAGTACGTGTCGAA
Consensus (2351) AGGCTGATGACCCTGACCGGCGTGTACGGGTTCTGGAAGTACGTGTCCAA
              2401                                              2450
Sh1    (2387) CCTGGAGAGGCGCGAGACCCGCCGCTACATCGAGATGTTCTACGCCCTGA
Sus1   (2367) CCTGGAGAGGCGCGAGACCCGGCGGTACCTGGAGATGCTGTACGCGCTCA
Sus3   (2308) GCTCGAGAGGCTGGAGACGAGGCGCTACCTTGAGATGTTCTACATACTGA
Consensus (2401) CCTGGAGAGGCGCGAGACCCGGCGCTACCT GAGATGTTCTACGC CTGA
              2451                                              2500
Sh1    (2437) AGTACCGTAGCCTGGCAAGCCAGGTTCCGCTGTCCTTCGA------TTAG
Sus1   (2417) AGTACCGCACCATGGCGAGCACCGTGCCGCTGGCCGTGGA------GGGA
Sus3   (2358) AGTTCCGCGAGCTGGCGAAGACCGTGCCGCTTGCAATTGACCAACCGCAG
Consensus (2451) AGTACCGCA CCTGGCGAGCACCGTGCCGCTGGCC T GA       G AG
              2501                                              2550
Sh1    (2481) TACGGGAAAGAAGGAGA-AGAAGAAGAAGAAGCCCAGGCCGGA-----G
Sus1   (2461) GAGCCCTCCAGCAAGTGA-TGCGTGACGGCGGCCACAGACCTGATC---G
Sus3   (2408) TAGCTTGCGCAACTGCGACTGCGTAGCACTTGGTACAAGACTGAAACCTG
Consensus (2501) TAGC  GC AGAA G GA TGCGTAACA   GGCACAGGCCTGA     G
              2551                                              2600
Sh1    (2525) AACCATCGCCTGCATTTCGATCT--------GT-TTCACCGCAATTCGC
Sus1   (2507) ATCGATGAGCGAGAGGGAGCACTCGGA-----GT-GTCGTGTCTTTTCCC
Sus3   (2458) AAGGACCTTCAGTAATTTAGGCGCGGCAGACGGTAGCCAATAAAATGTGC
Consensus (2551) AACGATC  C G A TT G CTCGG       GT GTCA    CAATTCGC
```

Figure 9e

```
                  2601                                          2650
       Sh1 (2565) ATTGTTAGTCGTGTATTGGAGTTATGTG--TACTTGGTTTCCAAGAACTT
       Sus1 (2551) TTGCCATTTCTTTCTTTCTTCTTTTTCC--TTCCCGGAGGCGAAAAAAAA
       Sus3 (2508) CGGAGCTGAACTGGTTTTTTATTATGTACATAATGGCAGTATAACAAAAT
  Consensus (2601)    TG   TGTC TG TTT TT TTATGT   TACT GGAGTC AA AAAAT
                  2651                                          2700
       Sh1 (2613) TGGTTCCTTCTCGTTTTTTTCCTTGTTTGAGCGTTTTTGGGCAGCGCTG
       Sus1 (2599) AGAGTC-TGCTT-TTGCTAGGCGGCGGGCGTTCGTTGCTGCTCTTTGCTT
       Sus3 (2558) TACTGAAGGCAGGTGGGTTGCAGTTGTGTGTTCGTTACTG--------TT
  Consensus (2651) TG TTC TGCT GTTG TTG CGTTGTGTGTTCGTT CTG  C    GCT
                  2701                                          2750
       Sh1 (2663) GCCTGGTTCCTAGTATGGTGGGAATTGGCTGCACCTTTTGCTTCGAATAA
       Sus1 (2647) CAAGAGTTAAAATTTACCTACC--TTGTCAAGGTCTTGTTCCATCATTGA
       Sus3 (2600) TACTGTATTATGTCAAGCTGTC----GGCTGCAATTTCTTTGCTGG--CA
  Consensus (2701)    ACTGGTT ATATTAAGCTG C   TTGGCTGCA CTT TTC  TGA T A
                  2751                                          2800
       Sh1 (2713) AAATGCCTGCTCGTTCACCTGTCTTCCAGAGTGC----------------
       Sus1 (2695) TCCGGGTGTCGCTTGTAGTAGTCTGATGGACTGTTAGTAGTTTGCGTTGC
       Sus3 (2644) AGCCGCAGGCACTGGTGAAGTGCTGATAAATACATCATATTCTGTTGACC
  Consensus (2751) A C GC GGC CTTGTA    GTCTGATAGA TG T   TA T TG     C
                  2801                                          2850
       Sh1 (2747) --------------------------------------------------
       Sus1 (2745) GTCGGTTGAGAGGGAACGTTGGTGGTGGTGGTGTGTGTGCAGTCAGGCGT
       Sus3 (2694) TGTGAAAAAAAAAAAAAAAAAAAAAAAAAAAAAAAGGGCGGCCGC-----
  Consensus (2801)       G   A A   AA                      G GG   C
                  2851                                          2900
       Sh1 (2747) --------------------------------------------------
       Sus1 (2795) GGTGCTCCCTTTGTTTCCTGGATGGGATGTTGCTCCTTGAATAATAATCG
       Sus3 (2738) --------------------------------------------------
  Consensus (2851)
                  2901                                          2950
       Sh1 (2747) --------------------------------------------------
       Sus1 (2845) TAGTGGCCTTGGAGCCCTTTTCCTGAAATAAGAGCAGCATCCTAGTGCTT
       Sus3 (2738) --------------------------------------------------
  Consensus (2901)
                  2951      2964
       Sh1 (2747) --------------
       Sus1 (2895) ACCTTTGCAGCTGT
       Sus3 (2738) --------------
  Consensus (2951)
```

Figure 9f

CGCCAGTCGCCAGTCGCCACAGCCACACCACACCACACTAGCCGCGGCCGCGGGTAGGAG

CGCGCGCGGCGCGGCGGAACGACCCACCGGTGGCGGCAGCC<u>ATGTCTGCCCCGAAGCTGA</u>

<u>ACCGCAACGCGAGCATCCGG</u>GACCGCGTCGAGGACACCCTCCACGCGCACCGCAACGAGC

TCGTCGCCCTCCTCTCCAAGTACGTGAACAAGGGGAAGGGCATCCTGCAGCCGCACCACA

TCCTCGACGCGCTCGACGAGGTCCAGGGCTCCGGGGTCCGCGCGCTCGCCGAGGGACCCT

TCCTCGACGTCCTCCGCTCCGCGCAGGAGGCGATCGTGCTGCCGCCG

Figure 10

Sorghum sequence from SEQ ID NO: 13 in SEQ ID NO: 11
ATGTCTGCCCCGAAGCTGAACCGCAACGCGAGCATCCGG Maize sequence from SEQ ID NO: 1 in SEQ ID NO: 11

```
gtcgaccgac ggtccggcg accgcgtcga ggacaccctc cacgcgcacc gcaacgagct    60
cgtcgccctc ctgtccaagt acgtgaacaa ggggaagggc atcctgcagc cgcaccacat   120
cctcgacgcg ctcgacgagg tccagggctc cggggccgc gcgctagccg agggaccctt   180
cctcgacgtc ctccgctccg cgcaggaggc gatcgtgctg ccgccgttcg tggccatcgc   240
ggtgcgcccg cgcccgggag tttgggagta cgtccgcgtc aacgttcacg agctcagcgt   300
cgagcagctc acagtctcgg agtacctccg cttcaaggag gagcttgtcg acggccagca   360
caatgatccc tacgttctcg agcttgactt cgagccgttc aatgtctcag tcccacgccc   420
aaatcggtca tcatctattg gaaacggtgt gcagttcctc aaccgacact tgtcctcaat   480
catgttccgc aacagggatt gcttggagcc cctgttggat ttcctccgtg gccaccggca   540
caagggggcat gttatgatgc ttaatgatag aatacaaagc ttggggaggc ttcagtctgt   600
gctgaccaaa gctgaggagc acttgtcaaa gctccctgct gacacaccat actcacaatt   660
tgcttataaa tttcaagagt ggggcctgga gaaaggttgg ggtgatacag caggacatgt   720
tttggaaatg atccatctcc ttctagacat cattcaggcg ccagaccat ctacccctaga   780
gaaattcttg gggaggatcc ccatgatttt taacgttgtt gtggtatccc ctcatggata   840
cttttggtcaa gctaatgtat taggcttgcc agacacagga ggacagatcg tctatatact   900
ggaccaagtc cgtgcactag aaaatgagat ggttctccgt ttaaagaaac aagggcttga   960
tgtttccca aagattctca ttgttactcg gctgatacca gatgcaaaag gaacatcatg  1020
caatcagcgg cttgagagaa ttagtggaac acagcatact tacatattac gagttcccct  1080
cagaaatgaa atggggatac ttaagaaatg gatatcaaga tttgatgtgt ggccatatct  1140
ggaaacattt gctgaggatg ctgctggtga aattgctgct gaattacaag gtactccaga  1200
cttcataatt ggaaactaca gtgatggaaa tcttgtggcg tcattgctat cttacaagat  1260
gggaattacc cagtgcaaca ttgctcatgc tctggaaaag actaagtatc cagattcaga  1320
catatttggg aagaatttcg atgagaagta ccattctcc tgccagttca ctgctgatat  1380
aattgctatg aacaatgctg attttatcat caccagcaca taccaagaaa ttgctggaag  1440
caaaaatact gttggacagt atgagagtca tactgccttt actctgcctg gtctgtaccg  1500
agttgtccat gggatcgatg tcttcgatcc aaagttcaat atagtctctc ctggagctga  1560
catgtccata tactttccac ataccgagaa ggccaagcga ctcacctctc ttcatggttc  1620
aatcgaaaat ttgatttatg acccggagca aaacgatgaa cacattgggc atctggatga  1680
ccggtcaaag cccatcctct tctccatggc aagactcgac agggtgaaga ataacagg   1740
gctggtcgaa gcttttgcta agtgcgctaa gctgagggag ctggtaaacc ttgtcgtcgt  1800
tgccgggtac aatgatgtca acaagtccaa ggacagggaa gagatcgcgg agatagagaa  1860
gatgcatgaa ctcatcaaga cccacaactt gttcgggcag ttccgctgga tctctgccca  1920
gacaaacagg gcccgtaacg gcgagctcta tcgctacatc gctgataccc atggtgcttt  1980
cgtacagccg gccttgtatg aagcgttcgg tctcaccgtc gttgaggcca tgacctgtgg  2040
gcttcctact ttcgcgacgc tccatggagg tccagctgag atcatagagc atggcgtctc  2100
gggcttccac attgacccgt accaccccga acaggctgtt aatctgatgg ccgacttctt  2160
cgaccggtgc aagcaagacc cagatcactg ggtgaatata tctggagcag ggctgcagcg  2220
catatacgag aagtacacat ggaagatata ctcagagagg ttgatgacac tggccggggt  2280
ctacggtttc tggaagtacg tgtcgaagct cgagaggctg gagacgaggc gctaccttga  2340
gatgttctac atactgaagt tccgcgagct ggcgaagacc gtgccgcttg caattgacca  2400
accgcagtag cttgcgcaac tgcgactgcg tagcacttgg tacaagactg aaacctgaag  2460
gaccttcagt aatttaggcg cggcagacgg tagccaataa aatgtgccgg agctgaactg  2520
gtttttatt atgtacataa tggcagtata acaaaattac tgaaggcagg tgggttgcag  2580
ttgtgtgttc gttactgttt actgtattat gtcaagctgt cggctgcaat ttctttgctg  2640
gcaagccgca ggcactggtg aagtgctgat aaatacatca tattctgttg acctgtgaaa  2700
aaaaaaaaa aaaaaaaaa aaaaaagggg cggccgc
```

Figure 11

SEQUENCE LISTING

<160> NUMBER OF SEQ ID NOS: 13

<210> SEQ ID NO 1
<211> LENGTH: 2737
<212> TYPE: DNA
<213> ORGANISM: Zea mays

<400> SEQUENCE: 1

| | | | | | | |
|---|---|---|---|---|---|---|
| gtcgacccac | gcgtccggcg | accgcgtcga | ggacaccctc | cacgcgcacc | gcaacgagct | 60 |
| cgtcgccctc | ctgtccaagt | acgtgaacaa | ggggaaggge | atcctgcagc | cgcaccacat | 120 |
| cctcgacgcg | ctcgacgagg | tccagggctc | cggggggccgc | gcgctagccg | agggacccctt | 180 |
| cctcgacgtc | ctccgctccg | cgcaggaggc | gatcgtgctg | ccgccgttcg | tggccatcgc | 240 |
| ggtgcgcccg | cgcccgggag | tttggagta | cgtccgcgtc | aacgttcacg | agctcagcgt | 300 |
| cgagcagctc | acagtctcgg | agtacctccg | cttcaaggag | gagcttgtcg | acggccagca | 360 |
| caatgatccc | tacgttctcg | agcttgactt | cgagccgttc | aatgtctcag | tcccacgccc | 420 |
| aaatcggtca | tcatctattg | gaaacggtgt | gcagttcctc | aaccgacact | tgtcctcaat | 480 |
| catgttccgc | aacagggatt | gcttggagcc | cctgttggat | ttcctccgtg | gccaccggca | 540 |
| caagggggcat | gttatgatgc | ttaatgatag | aatacaaagc | ttggggaggc | ttcagtctgt | 600 |
| gctgaccaaa | gctgaggagc | acttgtcaaa | gctccctgct | gacacaccat | actcacaatt | 660 |
| tgcttataaa | tttcaagagt | ggggcctgga | gaaaggttgg | ggtgatacag | caggacatgt | 720 |
| tttggaaatg | atccatctcc | ttctagacat | cattcaggcg | ccagacccat | ctaccctaga | 780 |
| gaaattcttg | gggaggatcc | ccatgatttt | taacgttgtt | gtggtatccc | ctcatggata | 840 |
| cttttggtcaa | gctaatgtat | taggcttgcc | agacacagga | ggacagatcg | tctatatact | 900 |
| ggaccaagtc | cgtgcactag | aaaatgagat | ggttctccgt | ttaaagaaac | aagggcttga | 960 |
| tgtttcccca | aagattctca | ttgttactcg | gctgatacca | gatgcaaaag | gaacatcatg | 1020 |
| caatcagcgg | cttgagagaa | ttagtggaac | acagcatact | tacatattac | gagttccctt | 1080 |
| cagaaatgaa | aatgggatac | ttaagaaatg | gatatcaaga | tttgatgtgt | ggccatatct | 1140 |
| ggaaacattt | gctgaggatg | ctgctggtga | aattgctgct | gaattacaag | gtactccaga | 1200 |
| cttcataatt | ggaaactaca | gtgatggaaa | tcttgtggcg | tcattgctat | cttacaagat | 1260 |
| gggaattacc | cagtgcaaca | ttgctcatgc | tctggaaaag | actaagtatc | cagattcaga | 1320 |
| catattttgg | aagaatttcg | atgagaagta | ccatttctcc | tgccagttca | ctgctgatat | 1380 |
| aattgctatg | aacaatgctg | attttatcat | caccagcaca | taccaagaaa | ttgctggaag | 1440 |
| caaaaatact | gttggacagt | atgagagtca | tactgccttt | actctgcctg | gtctgtaccg | 1500 |
| agttgtccat | gggatcgatg | tcttcgatcc | aaagttcaat | atagtctctc | ctggagctga | 1560 |
| catgtccata | tactttccac | ataccgagaa | ggccaagcga | ctcacctctc | ttcatggttc | 1620 |
| aatcgaaaat | ttgatttatg | acccgagca | aaacgatgaa | cacattgggc | atctggatga | 1680 |

-continued

```
ccggtcaaag cccatcctct tctccatggc aagactcgac agggtgaaga acataacagg    1740
gctggtcgaa gcttttgcta agtgcgctaa gctgagggag ctggtaaacc ttgtcgtcgt    1800
tgccgggtac aatgatgtca acaagtccaa ggacagggaa gagatcgcgg agatagagaa    1860
gatgcatgaa ctcatcaaga cccacaactt gttcgggcag ttccgctgga tctctgccca    1920
gacaaacagg gcccgtaacg gcgagctcta tcgctacatc gctgataccc atggtgcttt    1980
cgtacagccg gccttgtatg aagcgttcgg tctcaccgtc gttgaggcca tgacctgtgg    2040
gcttcctact ttcgcgacgc tccatggagg tccagctgag atcatagagc atggcgtctc    2100
gggcttccac attgacccgt accaccccga acaggctgtt aatctgatgg ccgacttctt    2160
cgaccggtgc aagcaagacc cagatcactg ggtgaatata tctggagcag gctgcagcg    2220 catatacgag aagtacacat ggaagatata ctcagagagg ttgatgacac tggccggggt    2280
ctacggtttc tggaagtacg tgtcgaagct cgagaggctg gagacgaggc gctaccttga    2340
gatgttctac atactgaagt ccgcgagct ggcgaagacc gtgccgcttg caattgacca    2400
accgcagtag cttgcgcaac tgcgactgcg tagcacttgg tacaagactg aaacctgaag    2460
gaccttcagt aatttaggcg cggcagacgg tagccaataa aatgtgccgg agctgaactg    2520
gttttttatt atgtacataa tggcagtata acaaaattac tgaaggcagg tgggttgcag    2580
ttgtgtgttc gttactgttt actgtattat gtcaagctgt cggctgcaat ttctttgctg    2640
gcaagccgca ggcactggtg aagtgctgat aaatacatca tattctgttg acctgtgaaa    2700 aaaaaaaaa aaaaaaaaa aaaaaaggg cggccgc                                2737
```

<210> SEQ ID NO 2
<211> LENGTH: 802
<212> TYPE: PRT
<213> ORGANISM: Zea mays

<400> SEQUENCE: 2

```
Ser Thr His Ala Ser Gly Asp Arg Val Glu Asp Thr Leu His Ala His
 1               5                  10                  15

Arg Asn Glu Leu Val Ala Leu Leu Ser Lys Tyr Val Asn Lys Gly Lys
            20                  25                  30

Gly Ile Leu Gln Pro His His Ile Leu Asp Ala Leu Asp Glu Val Gln
        35                  40                  45

Gly Ser Gly Gly Arg Ala Leu Ala Glu Gly Pro Phe Leu Asp Val Leu
    50                  55                  60

Arg Ser Ala Gln Glu Ala Ile Val Leu Pro Pro Phe Val Ala Ile Ala
65                  70                  75                  80

Val Arg Pro Arg Pro Gly Val Trp Glu Tyr Val Arg Val Asn Val His
                85                  90                  95

Glu Leu Ser Val Glu Gln Leu Thr Val Ser Glu Tyr Leu Arg Phe Lys
            100                 105                 110

Glu Glu Leu Val Asp Gly Gln His Asn Asp Pro Tyr Val Leu Glu Leu
        115                 120                 125

Asp Phe Glu Pro Phe Asn Val Ser Val Pro Arg Pro Asn Arg Ser Ser
    130                 135                 140

Ser Ile Gly Asn Gly Val Gln Phe Leu Asn Arg His Leu Ser Ser Ile
145                 150                 155                 160

Met Phe Arg Asn Arg Asp Cys Leu Glu Pro Leu Leu Asp Phe Leu Arg
                165                 170                 175

Gly His Arg His Lys Gly His Val Met Met Leu Asn Asp Arg Ile Gln
```

-continued

```
                180                 185                 190
Ser Leu Gly Arg Leu Gln Ser Val Leu Thr Lys Ala Glu Glu His Leu
                    195                 200                 205
Ser Lys Leu Pro Ala Asp Thr Pro Tyr Ser Gln Phe Ala Tyr Lys Phe
        210                 215                 220
Gln Glu Trp Gly Leu Glu Lys Gly Trp Gly Asp Thr Ala Gly His Val
225                 230                 235                 240
Leu Glu Met Ile His Leu Leu Leu Asp Ile Gln Ala Pro Asp Pro
                245                 250                 255
Ser Thr Leu Glu Lys Phe Leu Gly Arg Ile Pro Met Ile Phe Asn Val
        260                 265                 270
Val Val Val Ser Pro His Gly Tyr Phe Gly Gln Ala Asn Val Leu Gly
            275                 280                 285
Leu Pro Asp Thr Gly Gly Gln Ile Val Tyr Ile Leu Asp Gln Val Arg
        290                 295                 300
Ala Leu Glu Asn Glu Met Val Leu Arg Leu Lys Lys Gln Gly Leu Asp
305                 310                 315                 320
Val Ser Pro Lys Ile Leu Ile Val Thr Arg Leu Ile Pro Asp Ala Lys
                325                 330                 335
Gly Thr Ser Cys Asn Gln Arg Leu Glu Arg Ile Ser Gly Thr Gln His
                340                 345                 350
Thr Tyr Ile Leu Arg Val Pro Phe Arg Asn Glu Asn Gly Ile Leu Lys
        355                 360                 365
Lys Trp Ile Ser Arg Phe Asp Val Trp Pro Tyr Leu Glu Thr Phe Ala
    370                 375                 380
Glu Asp Ala Ala Gly Glu Ile Ala Ala Glu Leu Gln Gly Thr Pro Asp
385                 390                 395                 400
Phe Ile Ile Gly Asn Tyr Ser Asp Gly Asn Leu Val Ala Ser Leu Leu
                405                 410                 415
Ser Tyr Lys Met Gly Ile Thr Gln Cys Asn Ile Ala His Ala Leu Glu
                420                 425                 430
Lys Thr Lys Tyr Pro Asp Ser Asp Ile Phe Trp Lys Asn Phe Asp Glu
        435                 440                 445
Lys Tyr His Phe Ser Cys Gln Phe Thr Ala Asp Ile Ala Met Asn
    450                 455                 460
Asn Ala Asp Phe Ile Ile Thr Ser Thr Tyr Gln Glu Ile Ala Gly Ser
465                 470                 475                 480
Lys Asn Thr Val Gly Gln Tyr Glu Ser His Thr Ala Phe Thr Leu Pro
                485                 490                 495
Gly Leu Tyr Arg Val Val His Gly Ile Asp Val Phe Asp Pro Lys Phe
            500                 505                 510
Asn Ile Val Ser Pro Gly Ala Asp Met Ser Ile Tyr Phe Pro His Thr
        515                 520                 525
Glu Lys Ala Lys Arg Leu Thr Ser Leu His Gly Ser Ile Glu Asn Leu
    530                 535                 540
Ile Tyr Asp Pro Glu Gln Asn Asp Glu His Ile Gly His Leu Asp Asp
545                 550                 555                 560
Arg Ser Lys Pro Ile Leu Phe Ser Met Ala Arg Leu Asp Arg Val Lys
                565                 570                 575
Asn Ile Thr Gly Leu Val Glu Ala Phe Ala Lys Cys Ala Lys Leu Arg
            580                 585                 590
Glu Leu Val Asn Leu Val Val Val Ala Gly Tyr Asn Asp Val Asn Lys
        595                 600                 605
```

```
Ser Lys Asp Arg Glu Glu Ile Ala Glu Ile Glu Lys Met His Glu Leu
    610                 615                 620
Ile Lys Thr His Asn Leu Phe Gly Gln Phe Arg Trp Ile Ser Ala Gln
625                 630                 635                 640
Thr Asn Arg Ala Arg Asn Gly Glu Leu Tyr Arg Tyr Ile Ala Asp Thr
                645                 650                 655
His Gly Ala Phe Val Gln Pro Ala Leu Tyr Glu Ala Phe Gly Leu Thr
            660                 665                 670
Val Val Glu Ala Met Thr Cys Gly Leu Pro Thr Phe Ala Thr Leu His
        675                 680                 685
Gly Gly Pro Ala Glu Ile Ile Glu His Gly Val Ser Gly Phe His Ile
    690                 695                 700
Asp Pro Tyr His Pro Glu Gln Ala Val Asn Leu Met Ala Asp Phe Phe
705                 710                 715                 720
Asp Arg Cys Lys Gln Asp Pro Asp His Trp Val Asn Ile Ser Gly Ala
                725                 730                 735
Gly Leu Gln Arg Ile Tyr Glu Lys Tyr Thr Trp Lys Ile Tyr Ser Glu
            740                 745                 750
Arg Leu Met Thr Leu Ala Gly Val Tyr Gly Phe Trp Lys Tyr Val Ser
        755                 760                 765
Lys Leu Glu Arg Leu Glu Thr Arg Arg Tyr Leu Glu Met Phe Tyr Ile
    770                 775                 780
Leu Lys Phe Arg Glu Leu Ala Lys Thr Val Pro Leu Ala Ile Asp Gln
785                 790                 795                 800

Pro Gln

<210> SEQ ID NO 3
<211> LENGTH: 36
<212> TYPE: DNA
<213> ORGANISM: Artificial Sequence
<220> FEATURE:
<223> OTHER INFORMATION: Designed oligonucleotide based upon the adapter
      sequence and poly T to remove clones which have a poly A tail but
      no cDNA.

<400> SEQUENCE: 3
tcgacccacg cgtccgaaaa aaaaaaaaaa aaaaaa                              36

<210> SEQ ID NO 4
<211> LENGTH: 2746
<212> TYPE: DNA
<213> ORGANISM: Zea mays
<220> FEATURE:
<221> NAME/KEY: CDS
<222> LOCATION: (72)...(2480)

<400> SEQUENCE: 4
aaaccctccc tccctcctcc attggactgc ttgctccctg ttgaccattg ggtattctga    60
accatcgagc c atg gct gcc aag ctg act cgc ctt cac agt ctt cgc gaa   110
            Met Ala Ala Lys Leu Thr Arg Leu His Ser Leu Arg Glu
              1               5                  10 cgc ctt ggt gcc acc ttc tcc tcc cat ccc aat gaa ctg ata gca ctc   158
Arg Leu Gly Ala Thr Phe Ser Ser His Pro Asn Glu Leu Ile Ala Leu
 15                  20                  25 ttt tcc agg tat gtt cac cag ggc aag gga atg ctt cag cgc cat cag   206
Phe Ser Arg Tyr Val His Gln Gly Lys Gly Met Leu Gln Arg His Gln
 30                  35                  40                  45 ctg ctt gcg gag ttt gat gcc ctg ttt gat agt gac aag gag aag tat   254
```

-continued

| | | |
|---|---|---|
| Leu Leu Ala Glu Phe Asp Ala Leu Phe Asp Ser Asp Lys Glu Lys Tyr<br>                50                    55              60 | | |
| gca cca ttt gaa gac att ctt cgt gct gct cag gaa gca att gtg ctc<br>Ala Pro Phe Glu Asp Ile Leu Arg Ala Ala Gln Glu Ala Ile Val Leu<br>                65                    70                    75 | 302 | |
| ccc cca tgg gtt gca ctt gct atc agg cca agg cct ggt gtc tgg gat<br>Pro Pro Trp Val Ala Leu Ala Ile Arg Pro Arg Pro Gly Val Trp Asp<br>        80                    85                    90 | 350 | |
| tac att cgg gtg aat gta agt gag ctg gct gtg gag gag ctg agt gtt<br>Tyr Ile Arg Val Asn Val Ser Glu Leu Ala Val Glu Glu Leu Ser Val<br>        95                  100               105 | 398 | |
| tct gag tac ttg gca ttc aag gaa cag ctg gtg gat gga caa tcc aac<br>Ser Glu Tyr Leu Ala Phe Lys Glu Gln Leu Val Asp Gly Gln Ser Asn<br>110                  115                 120              125 | 446 | |
| agc aac ttt gtg ctt gag ctt gat ttt gag ccc ttc aat gcc tcc ttt<br>Ser Asn Phe Val Leu Glu Leu Asp Phe Glu Pro Phe Asn Ala Ser Phe<br>                130                  135              140 | 494 | |
| cct cgt cct tcc atg tcg aag tcc atc gga aat gga gtg caa ttc ctt<br>Pro Arg Pro Ser Met Ser Lys Ser Ile Gly Asn Gly Val Gln Phe Leu<br>                145                  150              155 | 542 | |
| aac cga cac ctg tcg tcc aag ttg ttc cag gac aag gag agt ttg tac<br>Asn Arg His Leu Ser Ser Lys Leu Phe Gln Asp Lys Glu Ser Leu Tyr<br>                160                  165              170 | 590 | |
| ccc ttg ctg aac ttc ctc aag gct cat aac tac aag ggc acg acg atg<br>Pro Leu Leu Asn Phe Leu Lys Ala His Asn Tyr Lys Gly Thr Thr Met<br>175                  180                 185 | 638 | |
| atg ttg aat gac aga atc caa agc ctt cgt ggt ctc caa tca tcc ctg<br>Met Leu Asn Asp Arg Ile Gln Ser Leu Arg Gly Leu Gln Ser Ser Leu<br>190                  195                 200              205 | 686 | |
| aga aag gca gag gag tat cta ctg agt gtt cct caa gac act ccc tac<br>Arg Lys Ala Glu Glu Tyr Leu Leu Ser Val Pro Gln Asp Thr Pro Tyr<br>                    210                  215              220 | 734 | |
| tcg gag ttc aac cat agg ttc caa gag ctt ggc ttg gag aag ggt tgg<br>Ser Glu Phe Asn His Arg Phe Gln Glu Leu Gly Leu Glu Lys Gly Trp<br>                225                  230              235 | 782 | |
| ggt gac act gcg aag cgt gtt ctc gac aca ctc cac ttg ctt ctc gac<br>Gly Asp Thr Ala Lys Arg Val Leu Asp Thr Leu His Leu Leu Leu Asp<br>                  240                  245              250 | 830 | |
| ctt ctt gag gcc cct gat cct gcc aac ttg gag aag ttc ctt gga act<br>Leu Leu Glu Ala Pro Asp Pro Ala Asn Leu Glu Lys Phe Leu Gly Thr<br>255                  260                 265 | 878 | |
| ata cca atg atg ttc aac gtt gtt atc ctg tct cct cat ggc tac ttc<br>Ile Pro Met Met Phe Asn Val Val Ile Leu Ser Pro His Gly Tyr Phe<br>270                  275                 280              285 | 926 | |
| gcc cag tcc aat gtg ctt gga tac cct gac act ggc ggt cag gtt gtg<br>Ala Gln Ser Asn Val Leu Gly Tyr Pro Asp Thr Gly Gly Gln Val Val<br>                    290                  295              300 | 974 | |
| tac att ctg gat caa gtc cgt gct ttg gag aat gag atg ctt ctg agg<br>Tyr Ile Leu Asp Gln Val Arg Ala Leu Glu Asn Glu Met Leu Leu Arg<br>                    305                  310              315 | 1022 | |
| att aag cag caa ggc ctt gat atc act ccg aag atc ctc att gtt acc<br>Ile Lys Gln Gln Gly Leu Asp Ile Thr Pro Lys Ile Leu Ile Val Thr<br>                  320                  325              330 | 1070 | |
| agg ctg ttg cct gat gct gct ggg act acg tgc ggt cag cgg ctg gag<br>Arg Leu Leu Pro Asp Ala Ala Gly Thr Thr Cys Gly Gln Arg Leu Glu<br>335                  340                 345 | 1118 | |
| aag gtc att ggt act gag cac aca gac atc att cgc gtt ccc ttc aga<br>Lys Val Ile Gly Thr Glu His Thr Asp Ile Ile Arg Val Pro Phe Arg<br>350                  355                 360              365 | 1166 | |

```
aat gag aat ggc atc ctc cgc aag tgg atc tct cgt ttt gat gtc tgg        1214
Asn Glu Asn Gly Ile Leu Arg Lys Trp Ile Ser Arg Phe Asp Val Trp
                370                 375                 380 cca tac ctg gag aca tac act gag gat gtt tcc agt gaa ata atg aaa        1262
Pro Tyr Leu Glu Thr Tyr Thr Glu Asp Val Ser Ser Glu Ile Met Lys
        385                 390                 395 gaa atg cag gcc aag cct gac ctt atc att ggc aac tac agc gat ggc        1310
Glu Met Gln Ala Lys Pro Asp Leu Ile Ile Gly Asn Tyr Ser Asp Gly
    400                 405                 410 aac cta gtc gcc act ctg ctc gcg cac aag ttg gga gtc act cag tgt        1358
Asn Leu Val Ala Thr Leu Leu Ala His Lys Leu Gly Val Thr Gln Cys
415                 420                 425 acc atc gct cat gcc ttg gag aaa acc aaa tac ccc aac tcg gac atc        1406
Thr Ile Ala His Ala Leu Glu Lys Thr Lys Tyr Pro Asn Ser Asp Ile
430                 435                 440                 445 tac ttg gac aaa ttc gac agc cag tac cac ttc tct tgc cag ttc aca        1454
Tyr Leu Asp Lys Phe Asp Ser Gln Tyr His Phe Ser Cys Gln Phe Thr
                450                 455                 460 gct gac ctt att gcc atg aac cac acc gat ttc atc atc acc agc aca        1502
Ala Asp Leu Ile Ala Met Asn His Thr Asp Phe Ile Ile Thr Ser Thr
            465                 470                 475 ttc caa gaa atc gcg gga agc aag gac acc gtg ggg cag tac gag tcc        1550
Phe Gln Glu Ile Ala Gly Ser Lys Asp Thr Val Gly Gln Tyr Glu Ser
        480                 485                 490 cat atc gcg ttc act ctt cct ggg ctc tac cgt gtc gtc cat ggc atc        1598
His Ile Ala Phe Thr Leu Pro Gly Leu Tyr Arg Val Val His Gly Ile
    495                 500                 505 gat gtt ttc gat ccc aag ttc aac att gtc tct cct gga gca gac atg        1646
Asp Val Phe Asp Pro Lys Phe Asn Ile Val Ser Pro Gly Ala Asp Met
510                 515                 520                 525 agt gtt tac tac cct tat acg gaa acc gac aag aga ctc act gcc ttc        1694
Ser Val Tyr Tyr Pro Tyr Thr Glu Thr Asp Lys Arg Leu Thr Ala Phe
                530                 535                 540 cat cct gaa atc gag gag ctc atc tac agc gac gtc gag aac tcc gag        1742
His Pro Glu Ile Glu Glu Leu Ile Tyr Ser Asp Val Glu Asn Ser Glu
            545                 550                 555 cac aag ttc gtg ctg aag gac aag aag aag ccg atc atc ttc tcg atg        1790
His Lys Phe Val Leu Lys Asp Lys Lys Lys Pro Ile Ile Phe Ser Met
        560                 565                 570 gcg cgt ctc gac cgc gtg aag aac atg aca ggc ctg gtc gag atg tac        1838
Ala Arg Leu Asp Arg Val Lys Asn Met Thr Gly Leu Val Glu Met Tyr
    575                 580                 585 ggc aag aac gcg cgc ctg agg gag ctg gcg aac ctc gtg atc gtt gcc        1886
Gly Lys Asn Ala Arg Leu Arg Glu Leu Ala Asn Leu Val Ile Val Ala
590                 595                 600                 605 ggt gac cac ggc aag gag tcc aag gac agg gag gag cag gcg gag ttc        1934
Gly Asp His Gly Lys Glu Ser Lys Asp Arg Glu Glu Gln Ala Glu Phe
                610                 615                 620 aag aag atg tac agc ctc atc gac gag tac aag ttg aag ggc cat atc        1982
Lys Lys Met Tyr Ser Leu Ile Asp Glu Tyr Lys Leu Lys Gly His Ile
            625                 630                 635 cgg tgg atc tcg gcg cag atg aac cgt gtc cgc aac ggg gag ctg tac        2030
Arg Trp Ile Ser Ala Gln Met Asn Arg Val Arg Asn Gly Glu Leu Tyr
        640                 645                 650 cgc tac att tgc gat acc aag ggc gca ttc gtg cag cct gcg ttc tac        2078
Arg Tyr Ile Cys Asp Thr Lys Gly Ala Phe Val Gln Pro Ala Phe Tyr
    655                 660                 665 gaa gcg ttc ggc ctg act gtg atc gag tcc atg acg tgc ggt ctg cca        2126
Glu Ala Phe Gly Leu Thr Val Ile Glu Ser Met Thr Cys Gly Leu Pro
670                 675                 680                 685
```

```
acg atc gcg acc tgc cat ggc ggc cct gct gag atc atc gtg gac ggg     2174
Thr Ile Ala Thr Cys His Gly Gly Pro Ala Glu Ile Ile Val Asp Gly
                690                 695                 700 gta tct ggc ctg cac att gac cct tac cac agc gac aag gcc gcg gat     2222
Val Ser Gly Leu His Ile Asp Pro Tyr His Ser Asp Lys Ala Ala Asp
            705                 710                 715 atc ctg gtc aac ttc ttt gac aaa tgc aag gca gat ccg agc tac tgg     2270
Ile Leu Val Asn Phe Phe Asp Lys Cys Lys Ala Asp Pro Ser Tyr Trp
        720                 725                 730 gac gag atc tca cag ggc ggc ctg cag aga att tat gag aag tac acc     2318
Asp Glu Ile Ser Gln Gly Gly Leu Gln Arg Ile Tyr Glu Lys Tyr Thr
    735                 740                 745 tgg aag ctc tac tcc gag agg ctg atg acc ctg acc ggc gtg tac ggg     2366
Trp Lys Leu Tyr Ser Glu Arg Leu Met Thr Leu Thr Gly Val Tyr Gly
750                 755                 760                 765 ttc tgg aag tac gtg agc aac ctg gag agg cgc gag acc cgc cgc tac     2414
Phe Trp Lys Tyr Val Ser Asn Leu Glu Arg Arg Glu Thr Arg Arg Tyr
                770                 775                 780 atc gag atg ttc tac gcc ctg aag tac cgt agc ctg gca agc cag gtt     2462
Ile Glu Met Phe Tyr Ala Leu Lys Tyr Arg Ser Leu Ala Ser Gln Val
            785                 790                 795 ccg ctg tcc ttc gat tag tacggggaaa gaaggagaag aagaagaaga            2510
Pro Leu Ser Phe Asp *
        800 agcccaggcc ggagaaccat cgcctgcatt tcgatctgtt tcaccgcaat tcgcattgtt   2570 agtcgtgtat tggagttatg tgtacttggt ttccaagaac tttggttcct tctcgttttt   2630 tttccttgtt tgagcgtttt tgggcagcgc tggcctggtt cctagtatgg tgggaattgg   2690 ctgcaccttt tgcttcgaat aaaaatgcct gctcgttcac ctgtcttcca gagtgc       2746

<210> SEQ ID NO 5
<211> LENGTH: 802
<212> TYPE: PRT
<213> ORGANISM: Zea mays

<400> SEQUENCE: 5

Met Ala Ala Lys Leu Thr Arg Leu His Ser Leu Arg Glu Arg Leu Gly
 1               5                  10                  15

Ala Thr Phe Ser Ser His Pro Asn Glu Leu Ile Ala Leu Phe Ser Arg
            20                  25                  30

Tyr Val His Gln Gly Lys Gly Met Leu Gln Arg His Gln Leu Leu Ala
        35                  40                  45

Glu Phe Asp Ala Leu Phe Asp Ser Asp Lys Glu Lys Tyr Ala Pro Phe
    50                  55                  60

Glu Asp Ile Leu Arg Ala Ala Gln Glu Ala Ile Val Leu Pro Pro Trp
65                  70                  75                  80

Val Ala Leu Ala Ile Arg Pro Arg Pro Gly Val Trp Asp Tyr Ile Arg
                85                  90                  95

Val Asn Val Ser Glu Leu Ala Val Glu Glu Leu Ser Val Ser Glu Tyr
            100                 105                 110

Leu Ala Phe Lys Glu Gln Leu Val Asp Gly Gln Ser Asn Ser Asn Phe
        115                 120                 125

Val Leu Glu Leu Asp Phe Glu Pro Phe Asn Ala Ser Phe Pro Arg Pro
    130                 135                 140

Ser Met Ser Lys Ser Ile Gly Asn Gly Val Gln Phe Leu Asn Arg His
145                 150                 155                 160
```

-continued

Leu Ser Ser Lys Leu Phe Gln Asp Lys Glu Ser Leu Tyr Pro Leu Leu
            165                 170                 175

Asn Phe Leu Lys Ala His Asn Tyr Lys Gly Thr Thr Met Met Leu Asn
            180                 185                 190

Asp Arg Ile Gln Ser Leu Arg Gly Leu Gln Ser Ser Leu Arg Lys Ala
            195                 200                 205

Glu Glu Tyr Leu Leu Ser Val Pro Gln Asp Thr Pro Tyr Ser Glu Phe
210                 215                 220

Asn His Arg Phe Gln Glu Leu Gly Leu Glu Lys Gly Trp Gly Asp Thr
225                 230                 235                 240

Ala Lys Arg Val Leu Asp Thr Leu His Leu Leu Asp Leu Leu Glu
            245                 250                 255

Ala Pro Asp Pro Ala Asn Leu Glu Lys Phe Leu Gly Thr Ile Pro Met
            260                 265                 270

Met Phe Asn Val Val Ile Leu Ser Pro His Gly Tyr Phe Ala Gln Ser
            275                 280                 285

Asn Val Leu Gly Tyr Pro Asp Thr Gly Gly Gln Val Val Tyr Ile Leu
290                 295                 300

Asp Gln Val Arg Ala Leu Glu Asn Glu Met Leu Leu Arg Ile Lys Gln
305                 310                 315                 320

Gln Gly Leu Asp Ile Thr Pro Lys Ile Leu Ile Val Thr Arg Leu Leu
            325                 330                 335

Pro Asp Ala Ala Gly Thr Thr Cys Gly Gln Arg Leu Glu Lys Val Ile
            340                 345                 350

Gly Thr Glu His Thr Asp Ile Ile Arg Val Pro Phe Arg Asn Glu Asn
            355                 360                 365

Gly Ile Leu Arg Lys Trp Ile Ser Arg Phe Asp Val Trp Pro Tyr Leu
            370                 375                 380

Glu Thr Tyr Thr Glu Asp Val Ser Ser Glu Ile Met Lys Glu Met Gln
385                 390                 395                 400

Ala Lys Pro Asp Leu Ile Ile Gly Asn Tyr Ser Asp Gly Asn Leu Val
            405                 410                 415

Ala Thr Leu Leu Ala His Lys Leu Gly Val Thr Gln Cys Thr Ile Ala
            420                 425                 430

His Ala Leu Glu Lys Thr Lys Tyr Pro Asn Ser Asp Ile Tyr Leu Asp
            435                 440                 445

Lys Phe Asp Ser Gln Tyr His Phe Ser Cys Gln Phe Thr Ala Asp Leu
450                 455                 460

Ile Ala Met Asn His Thr Asp Phe Ile Ile Thr Ser Thr Phe Gln Glu
465                 470                 475                 480

Ile Ala Gly Ser Lys Asp Thr Val Gly Gln Tyr Glu Ser His Ile Ala
            485                 490                 495

Phe Thr Leu Pro Gly Leu Tyr Arg Val Val His Gly Ile Asp Val Phe
            500                 505                 510

Asp Pro Lys Phe Asn Ile Val Ser Pro Gly Ala Asp Met Ser Val Tyr
            515                 520                 525

Tyr Pro Tyr Thr Glu Thr Asp Lys Arg Leu Thr Ala Phe His Pro Glu
            530                 535                 540

Ile Glu Glu Leu Ile Tyr Ser Asp Val Glu Asn Ser Glu His Lys Phe
545                 550                 555                 560

Val Leu Lys Asp Lys Lys Pro Ile Ile Phe Ser Met Ala Arg Leu
            565                 570                 575

Asp Arg Val Lys Asn Met Thr Gly Leu Val Glu Met Tyr Gly Lys Asn

```
                    580             585             590
Ala Arg Leu Arg Glu Leu Ala Asn Leu Val Ile Val Ala Gly Asp His
        595                 600                 605

Gly Lys Glu Ser Lys Asp Arg Glu Glu Gln Ala Glu Phe Lys Lys Met
        610                 615                 620

Tyr Ser Leu Ile Asp Glu Tyr Lys Leu Lys Gly His Ile Arg Trp Ile
625                 630                 635                 640

Ser Ala Gln Met Asn Arg Val Arg Asn Gly Glu Leu Tyr Arg Tyr Ile
                645                 650                 655

Cys Asp Thr Lys Gly Ala Phe Val Gln Pro Ala Phe Tyr Glu Ala Phe
        660                 665                 670

Gly Leu Thr Val Ile Glu Ser Met Thr Cys Gly Leu Pro Thr Ile Ala
        675                 680                 685

Thr Cys His Gly Gly Pro Ala Glu Ile Ile Val Asp Gly Val Ser Gly
        690                 695                 700

Leu His Ile Asp Pro Tyr His Ser Asp Lys Ala Asp Ile Leu Val
705                 710                 715                 720

Asn Phe Phe Asp Lys Cys Lys Ala Asp Pro Ser Tyr Trp Asp Glu Ile
                725                 730                 735

Ser Gln Gly Gly Leu Gln Arg Ile Tyr Glu Lys Tyr Thr Trp Lys Leu
        740                 745                 750

Tyr Ser Glu Arg Leu Met Thr Leu Thr Gly Val Tyr Gly Phe Trp Lys
        755                 760                 765

Tyr Val Ser Asn Leu Glu Arg Arg Glu Thr Arg Tyr Ile Glu Met
770                 775                 780

Phe Tyr Ala Leu Lys Tyr Arg Ser Leu Ala Ser Gln Val Pro Leu Ser
785                 790                 795                 800

Phe Asp

<210> SEQ ID NO 6
<211> LENGTH: 2908
<212> TYPE: DNA
<213> ORGANISM: Zea mays
<220> FEATURE:
<221> NAME/KEY: CDS
<222> LOCATION: (28)...(2478)

<400> SEQUENCE: 6
gcctgaggat ccaggaagag gacagca atg ggg gaa ggt gca ggt gac cgt gtc    54
                               Met Gly Glu Gly Ala Gly Asp Arg Val
                                 1               5 ctg agc cgc ctc cac agc gtc agg gag cgc att ggc gac tca ctc tct    102
Leu Ser Arg Leu His Ser Val Arg Glu Arg Ile Gly Asp Ser Leu Ser
 10                  15                  20                  25 gcc cac ccc aat gag ctt gtc gcc gtc ttc acc agg ctg aaa aac ctt    150
Ala His Pro Asn Glu Leu Val Ala Val Phe Thr Arg Leu Lys Asn Leu
                 30                  35                  40 gga aag ggt atg ctg cag ccc cac cag atc att gcc gag tac aac aat    198
Gly Lys Gly Met Leu Gln Pro His Gln Ile Ile Ala Glu Tyr Asn Asn
             45                  50                  55 gcg atc cct gag gct gag cgc gag aag ctc aag gat ggt gct ttt gag    246
Ala Ile Pro Glu Ala Glu Arg Glu Lys Leu Lys Asp Gly Ala Phe Glu
         60                  65                  70 gat gtc ctg agg gca gct cag gag gcg att gtc atc ccc cca tgg gtt    294
Asp Val Leu Arg Ala Ala Gln Glu Ala Ile Val Ile Pro Pro Trp Val
     75                  80                  85 gca ctt gcc atc cgc cct agg cct ggt gtc tgg gag tat gtg agg gtc    342
```

|   |   |   |   |   |   |   |   |   |   |   |   |   |   |   |   |
|---|---|---|---|---|---|---|---|---|---|---|---|---|---|---|---|
| Ala | Leu | Ala | Ile | Arg | Pro | Arg | Pro | Gly | Val | Trp | Glu | Tyr | Val | Arg | Val |
| 90 |   |   |   | 95 |   |   |   |   | 100 |   |   |   |   | 105 |   |

```
aac gtc agt gag ctc gct gtt gag gag ctg aga gtt cct gag tac ctg        390
Asn Val Ser Glu Leu Ala Val Glu Glu Leu Arg Val Pro Glu Tyr Leu
            110                 115                 120 cag ttc aag gaa cag ctt gtg gaa gaa ggc ccc aac aac aac ttt gtt        438
Gln Phe Lys Glu Gln Leu Val Glu Glu Gly Pro Asn Asn Asn Phe Val
        125                 130                 135 ctt gag ctg gac ttt gag cca ttc aat gcc tcc ttc ccc cgt cct tct        486
Leu Glu Leu Asp Phe Glu Pro Phe Asn Ala Ser Phe Pro Arg Pro Ser
        140                 145                 150 ctg tca aag tcc att ggc aat ggc gtg cag ttc ctc aac agg cac ctg        534
Leu Ser Lys Ser Ile Gly Asn Gly Val Gln Phe Leu Asn Arg His Leu
    155                 160                 165 tca tca aag ctc ttc cat gac aag gag agc atg tac ccc ttg ctc aac        582
Ser Ser Lys Leu Phe His Asp Lys Glu Ser Met Tyr Pro Leu Leu Asn
170             175                 180                 185 ttc ctt cgc gcc cac aac tac aag ggg atg acc atg atg ttg aac gac        630
Phe Leu Arg Ala His Asn Tyr Lys Gly Met Thr Met Met Leu Asn Asp
                190                 195                 200 aga atc cgc agt ctc agt gct ctg caa ggt gcg ctg agg aag gct gag        678
Arg Ile Arg Ser Leu Ser Ala Leu Gln Gly Ala Leu Arg Lys Ala Glu
            205                 210                 215 gag cac ctg tcc acc cta caa gct gat acc cca tac tct gaa ttt cac        726
Glu His Leu Ser Thr Leu Gln Ala Asp Thr Pro Tyr Ser Glu Phe His
        220                 225                 230 cac agg ttc cag gaa ctt ggt ctg gag aag ggt tgg ggt gat tgc gct        774
His Arg Phe Gln Glu Leu Gly Leu Glu Lys Gly Trp Gly Asp Cys Ala
    235                 240                 245 aag cgt gca cag gag act atc cac ctc ctc ttg gac ctc ctg gag gcc        822
Lys Arg Ala Gln Glu Thr Ile His Leu Leu Leu Asp Leu Leu Glu Ala
250             255                 260                 265 cca gat ccg tcc acc ctg gag aag ttc ctt gga acg atc ccc atg gtg        870
Pro Asp Pro Ser Thr Leu Glu Lys Phe Leu Gly Thr Ile Pro Met Val
                270                 275                 280 ttc aat gtc gtt atc ctc tcc cct cat ggt tac ttc gct caa gct aat        918
Phe Asn Val Val Ile Leu Ser Pro His Gly Tyr Phe Ala Gln Ala Asn
            285                 290                 295 gtc ttg ggt tac cct gac acc gga ggc cag gtt gtc tac atc ttg gat        966
Val Leu Gly Tyr Pro Asp Thr Gly Gly Gln Val Val Tyr Ile Leu Asp
        300                 305                 310 caa gtg cgc gct atg gag aac gaa atg ctg ctg agg atc aag cag tgt       1014
Gln Val Arg Ala Met Glu Asn Glu Met Leu Leu Arg Ile Lys Gln Cys
    315                 320                 325 ggt ctt gac atc acg ccg aag atc ctt att gtc acc agg ttg ctc cct       1062
Gly Leu Asp Ile Thr Pro Lys Ile Leu Ile Val Thr Arg Leu Leu Pro
330             335                 340                 345 gat gca act ggc acc acc tgt ggc cag cgc ctt gag aag gtc ctt ggc       1110
Asp Ala Thr Gly Thr Thr Cys Gly Gln Arg Leu Glu Lys Val Leu Gly
                350                 355                 360 acc gag cac tgc cat atc ctt cgc gtg cca ttc aga aca gaa aac gga       1158
Thr Glu His Cys His Ile Leu Arg Val Pro Phe Arg Thr Glu Asn Gly
            365                 370                 375 atc gtt cgc aag tgg atc tcg cga ttt gaa gtc tgg ccg tac ctg gag       1206
Ile Val Arg Lys Trp Ile Ser Arg Phe Glu Val Trp Pro Tyr Leu Glu
        380                 385                 390 act tac act gat gac gtg gcg cat gag att gct gga gag ctt cag gcc       1254
Thr Tyr Thr Asp Asp Val Ala His Glu Ile Ala Gly Glu Leu Gln Ala
    395                 400                 405
```

```
aat cct gac ctg atc atc gga aac tac agt gac gga aac ctt gtt gcg    1302
Asn Pro Asp Leu Ile Ile Gly Asn Tyr Ser Asp Gly Asn Leu Val Ala
410             415                 420                 425 tgt ttg ctc gcc cac aag atg ggt gtt act cac tgt acc att gcc cat    1350
Cys Leu Leu Ala His Lys Met Gly Val Thr His Cys Thr Ile Ala His
                430                 435                 440 gcg ctt gag aaa act aag tac cct aac tcc gac ctc tac tgg aag aag    1398
Ala Leu Glu Lys Thr Lys Tyr Pro Asn Ser Asp Leu Tyr Trp Lys Lys
            445                 450                 455 ttt gag gat cac tac cac ttc tcg tgc cag ttc acc act gac ttg att    1446
Phe Glu Asp His Tyr His Phe Ser Cys Gln Phe Thr Thr Asp Leu Ile
        460                 465                 470 gca atg aac cat gcc gac ttc atc atc acc agt acc ttc caa gag atc    1494
Ala Met Asn His Ala Asp Phe Ile Ile Thr Ser Thr Phe Gln Glu Ile
475                 480                 485 gcc gga aac aag gac acc gtc ggc cag tac gag tca cac atg gcg ttc    1542
Ala Gly Asn Lys Asp Thr Val Gly Gln Tyr Glu Ser His Met Ala Phe
490                 495                 500                 505 aca atg cct ggc ctg tac cgc gtt gtc cac ggc att gat gtg ttc gac    1590
Thr Met Pro Gly Leu Tyr Arg Val Val His Gly Ile Asp Val Phe Asp
                510                 515                 520 ccc aag ttc aac atc gtg tct cct ggc gcg gac ctg tcc atc tac ttc    1638
Pro Lys Phe Asn Ile Val Ser Pro Gly Ala Asp Leu Ser Ile Tyr Phe
            525                 530                 535 ccg tac acc gag tcg cac aag agg ctg acc tcc ctt cac ccg gag att    1686
Pro Tyr Thr Glu Ser His Lys Arg Leu Thr Ser Leu His Pro Glu Ile
        540                 545                 550 gag gag ctc ctg tac agc caa acc gag aac acg gag cac aag ttc gtt    1734
Glu Glu Leu Leu Tyr Ser Gln Thr Glu Asn Thr Glu His Lys Phe Val
555                 560                 565 ctg aac gac agg aac aag cca atc atc ttc tcc atg gct cgt ctc gac    1782
Leu Asn Asp Arg Asn Lys Pro Ile Ile Phe Ser Met Ala Arg Leu Asp
570                 575                 580                 585 cgt gtg aag aac ttg act ggg ctg gtg gag ctg tac ggc cgg aac aag    1830
Arg Val Lys Asn Leu Thr Gly Leu Val Glu Leu Tyr Gly Arg Asn Lys
                590                 595                 600 cgg ctg cag gag ctg gtg aac ctc gtg gtc gtc tgc ggc gac cat ggc    1878
Arg Leu Gln Glu Leu Val Asn Leu Val Val Val Cys Gly Asp His Gly
            605                 610                 615 aac cct tcc aag gac aag gag gag cag gcc gag ttc aag aag atg ttt    1926
Asn Pro Ser Lys Asp Lys Glu Glu Gln Ala Glu Phe Lys Lys Met Phe
        620                 625                 630 gac ctc atc gag cag tac aac ctg aac ggg cac atc cgc tgg atc tcc    1974
Asp Leu Ile Glu Gln Tyr Asn Leu Asn Gly His Ile Arg Trp Ile Ser
635                 640                 645 gcc cag atg aac cgc gtc cgc aac ggc gag ctg tac cgc tac atc tgc    2022
Ala Gln Met Asn Arg Val Arg Asn Gly Glu Leu Tyr Arg Tyr Ile Cys
650                 655                 660                 665 gac acc aag ggc gcc ttc gtg cag cct gct ttc tac gag gct ttc ggg    2070
Asp Thr Lys Gly Ala Phe Val Gln Pro Ala Phe Tyr Glu Ala Phe Gly
                670                 675                 680 ctg acg gtg gtt gag gcc atg acc tgc ggc ctg ccc acg ttc gcc acc    2118
Leu Thr Val Val Glu Ala Met Thr Cys Gly Leu Pro Thr Phe Ala Thr
            685                 690                 695 gcc tac ggc ggt ccg gcc gag atc atc gtg cac ggc gtg tct ggc tac    2166
Ala Tyr Gly Gly Pro Ala Glu Ile Ile Val His Gly Val Ser Gly Tyr
        700                 705                 710 cac atc gac cct tac cag ggc gac aag gcg tcg gcc ctg ctc gtg gac    2214
His Ile Asp Pro Tyr Gln Gly Asp Lys Ala Ser Ala Leu Leu Val Asp
715                 720                 725
```

```
ttc ttc gac aag tgc cag gcg gag ccg agc cac tgg agc aag atc tcc      2262
Phe Phe Asp Lys Cys Gln Ala Glu Pro Ser His Trp Ser Lys Ile Ser
730                 735                 740                 745 cag ggc ggg ctc cag cgt atc gag gag aag tac acc tgg aag ctg tac      2310
Gln Gly Gly Leu Gln Arg Ile Glu Glu Lys Tyr Thr Trp Lys Leu Tyr
                750                 755                 760 tcg gag agg ctg atg acc ctc acc ggc gtg tac ggg ttc tgg aag tac      2358
Ser Glu Arg Leu Met Thr Leu Thr Gly Val Tyr Gly Phe Trp Lys Tyr
            765                 770                 775 gtg tcc aac ctg gag agg cgc gag acc cgg cgg tac ctg gag atg ctg      2406
Val Ser Asn Leu Glu Arg Arg Glu Thr Arg Arg Tyr Leu Glu Met Leu
        780                 785                 790 tac gcg ctc aag tac cgc acc atg gcg agc acc gtg ccg ctg gcc gtg      2454
Tyr Ala Leu Lys Tyr Arg Thr Met Ala Ser Thr Val Pro Leu Ala Val
    795                 800                 805 gag gga gag ccc tcc agc aag tga tgcgtgacgg cggccacaga cctgatcgat    2508
Glu Gly Glu Pro Ser Ser Lys *
810                 815 cgatgagcga gagggagcac tcggagtgtc gtgtcttttc ccttgccatt tctttctttc    2568 ttcttttttcc ttcccggagg cgaaaaaaaa agagtctgct tttgctaggc ggcgggcgtt   2628
cgttgctgct ctttgcttca agagttaaaa tttacctacc ttgtcaaggt cttgttccat    2688
cattgatccg ggtgtcgctt gtagtagtct gatggactgt tagtagtttg cgttgcgtcg    2748
gttgagaggg aacgttggtg gtggtggtgt gtgtgcagtc aggcgtggtg ctcccttttgt   2808 ttcctggatg ggatgttgct ccttgaataa taatcgtagt ggccttggag ccctttttcct   2868 gaaataagag cagcatccta gtgcttacct ttgcagctgt                          2908

<210> SEQ ID NO 7
<211> LENGTH: 816
<212> TYPE: PRT
<213> ORGANISM: Zea mays

<400> SEQUENCE: 7

Met Gly Glu Gly Ala Gly Asp Arg Val Leu Ser Arg Leu His Ser Val
1               5                   10                  15

Arg Glu Arg Ile Gly Asp Ser Leu Ser Ala His Pro Asn Glu Leu Val
            20                  25                  30

Ala Val Phe Thr Arg Leu Lys Asn Leu Gly Lys Gly Met Leu Gln Pro
        35                  40                  45

His Gln Ile Ile Ala Glu Tyr Asn Asn Ala Ile Pro Glu Ala Glu Arg
    50                  55                  60

Glu Lys Leu Lys Asp Gly Ala Phe Glu Asp Val Leu Arg Ala Ala Gln
65                  70                  75                  80

Glu Ala Ile Val Ile Pro Pro Trp Val Ala Leu Ala Ile Arg Pro Arg
                85                  90                  95

Pro Gly Val Trp Glu Tyr Val Arg Val Asn Val Ser Glu Leu Ala Val
            100                 105                 110

Glu Glu Leu Arg Val Pro Glu Tyr Leu Gln Phe Lys Glu Gln Leu Val
        115                 120                 125

Glu Glu Gly Pro Asn Asn Phe Val Leu Glu Leu Asp Phe Glu Pro
    130                 135                 140

Phe Asn Ala Ser Phe Pro Arg Pro Ser Leu Ser Lys Ser Ile Gly Asn
145                 150                 155                 160

Gly Val Gln Phe Leu Asn Arg His Leu Ser Ser Lys Leu Phe His Asp
                165                 170                 175
```

```
Lys Glu Ser Met Tyr Pro Leu Leu Asn Phe Leu Arg Ala His Asn Tyr
            180                 185                 190

Lys Gly Met Thr Met Met Leu Asn Asp Arg Ile Arg Ser Leu Ser Ala
            195                 200                 205

Leu Gln Gly Ala Leu Arg Lys Ala Glu Glu His Leu Ser Thr Leu Gln
            210                 215                 220

Ala Asp Thr Pro Tyr Ser Glu Phe His His Arg Phe Gln Glu Leu Gly
225                 230                 235                 240

Leu Glu Lys Gly Trp Gly Asp Cys Ala Lys Arg Ala Gln Glu Thr Ile
            245                 250                 255

His Leu Leu Leu Asp Leu Leu Glu Ala Pro Asp Pro Ser Thr Leu Glu
            260                 265                 270

Lys Phe Leu Gly Thr Ile Pro Met Val Phe Asn Val Ile Leu Ser
            275                 280                 285

Pro His Gly Tyr Phe Ala Gln Ala Asn Val Leu Gly Tyr Pro Asp Thr
            290                 295                 300

Gly Gly Gln Val Val Tyr Ile Leu Asp Gln Val Arg Ala Met Glu Asn
305                 310                 315                 320

Glu Met Leu Leu Arg Ile Lys Gln Cys Gly Leu Asp Ile Thr Pro Lys
            325                 330                 335

Ile Leu Ile Val Thr Arg Leu Leu Pro Asp Ala Thr Gly Thr Thr Cys
            340                 345                 350

Gly Gln Arg Leu Glu Lys Val Leu Gly Thr Glu His Cys His Ile Leu
            355                 360                 365

Arg Val Pro Phe Arg Thr Glu Asn Gly Ile Val Arg Lys Trp Ile Ser
            370                 375                 380

Arg Phe Glu Val Trp Pro Tyr Leu Glu Thr Tyr Thr Asp Asp Val Ala
385                 390                 395                 400

His Glu Ile Ala Gly Glu Leu Gln Ala Asn Pro Asp Leu Ile Ile Gly
            405                 410                 415

Asn Tyr Ser Asp Gly Asn Leu Val Ala Cys Leu Leu Ala His Lys Met
            420                 425                 430

Gly Val Thr His Cys Thr Ile Ala His Ala Leu Glu Lys Thr Lys Tyr
            435                 440                 445

Pro Asn Ser Asp Leu Tyr Trp Lys Lys Phe Glu Asp His Tyr His Phe
            450                 455                 460

Ser Cys Gln Phe Thr Thr Asp Leu Ile Ala Met Asn His Ala Asp Phe
465                 470                 475                 480

Ile Ile Thr Ser Thr Phe Gln Glu Ile Ala Gly Asn Lys Asp Thr Val
            485                 490                 495

Gly Gln Tyr Glu Ser His Met Ala Phe Thr Met Pro Gly Leu Tyr Arg
            500                 505                 510

Val Val His Gly Ile Asp Val Phe Asp Pro Lys Phe Asn Ile Val Ser
            515                 520                 525

Pro Gly Ala Asp Leu Ser Ile Tyr Phe Pro Tyr Thr Glu Ser His Lys
            530                 535                 540

Arg Leu Thr Ser Leu His Pro Glu Ile Glu Glu Leu Leu Tyr Ser Gln
545                 550                 555                 560

Thr Glu Asn Thr Glu His Lys Phe Val Leu Asn Asp Arg Asn Lys Pro
            565                 570                 575

Ile Ile Phe Ser Met Ala Arg Leu Asp Arg Val Lys Asn Leu Thr Gly
            580                 585                 590
```

```
Leu Val Glu Leu Tyr Gly Arg Asn Lys Arg Leu Gln Glu Leu Val Asn
    595                 600                 605

Leu Val Val Cys Gly Asp His Gly Asn Pro Ser Lys Asp Lys Glu
610                 615                 620

Glu Gln Ala Glu Phe Lys Lys Met Phe Asp Leu Ile Glu Gln Tyr Asn
625                 630                 635                 640

Leu Asn Gly His Ile Arg Trp Ile Ser Ala Gln Met Asn Arg Val Arg
                645                 650                 655

Asn Gly Glu Leu Tyr Arg Tyr Ile Cys Asp Thr Lys Gly Ala Phe Val
            660                 665                 670

Gln Pro Ala Phe Tyr Glu Ala Phe Gly Leu Thr Val Glu Ala Met
    675                 680                 685

Thr Cys Gly Leu Pro Thr Phe Ala Thr Ala Tyr Gly Gly Pro Ala Glu
690                 695                 700

Ile Ile Val His Gly Val Ser Gly Tyr His Ile Asp Pro Tyr Gln Gly
705                 710                 715                 720

Asp Lys Ala Ser Ala Leu Leu Val Asp Phe Phe Asp Lys Cys Gln Ala
                725                 730                 735

Glu Pro Ser His Trp Ser Lys Ile Ser Gln Gly Gly Leu Gln Arg Ile
            740                 745                 750

Glu Glu Lys Tyr Thr Trp Lys Leu Tyr Ser Glu Arg Leu Met Thr Leu
        755                 760                 765

Thr Gly Val Tyr Gly Phe Trp Lys Tyr Val Ser Asn Leu Glu Arg Arg
770                 775                 780

Glu Thr Arg Arg Tyr Leu Glu Met Leu Tyr Ala Leu Lys Tyr Arg Thr
785                 790                 795                 800

Met Ala Ser Thr Val Pro Leu Ala Val Glu Gly Glu Pro Ser Ser Lys
                805                 810                 815

<210> SEQ ID NO 8
<211> LENGTH: 25
<212> TYPE: DNA
<213> ORGANISM: Zea mays

<400> SEQUENCE: 8
acggaatcgt tcgcaagtgg atctc                                        25

<210> SEQ ID NO 9
<211> LENGTH: 25
<212> TYPE: DNA
<213> ORGANISM: Zea mays

<400> SEQUENCE: 9
gatgattggc ttgttcctgt cgttc                                        25

<210> SEQ ID NO 10
<211> LENGTH: 32
<212> TYPE: DNA
<213> ORGANISM: Zea mays

<400> SEQUENCE: 10
agagaagcca acgccawcgc ctcyatttcg tc                                32

<210> SEQ ID NO 11
<211> LENGTH: 2757
<212> TYPE: DNA
<213> ORGANISM: Zea mays
<220> FEATURE:
<221> NAME/KEY: CDS
```

```
<222> LOCATION: (1)...(2430)
<220> FEATURE:
<221> NAME/KEY: source
<222> LOCATION: (1)...(39)
<223> OTHER INFORMATION: Sorghum pronpinquum
<220> FEATURE:
<221> NAME/KEY: source
<222> LOCATION: (40)...(2757)
<223> OTHER INFORMATION: Zea mays

<400> SEQUENCE: 11 atg tct gcc ccg aag ctg aac cgc aac gcg agc atc cgg gac cgc gtc      48
Met Ser Ala Pro Lys Leu Asn Arg Asn Ala Ser Ile Arg Asp Arg Val
 1               5                  10                  15 gag gac acc ctc cac gcg cac cgc aac gag ctc gtc gcc ctc ctc tcc      96
Glu Asp Thr Leu His Ala His Arg Asn Glu Leu Val Ala Leu Leu Ser
             20                  25                  30 aag tac gtg aac aag ggg aag ggc atc ctg cag ccg cac cac atc ctc     144
Lys Tyr Val Asn Lys Gly Lys Gly Ile Leu Gln Pro His His Ile Leu
         35                  40                  45 gac gcg ctc gac gag gtc cag ggc tcc ggg gtc cgc gcg ctc gcc gag     192
Asp Ala Leu Asp Glu Val Gln Gly Ser Gly Val Arg Ala Leu Ala Glu
     50                  55                  60 gga ccc ttc ctc gac gtc ctc cgc tcc gcg cag gag gcg atc gtg ctg     240
Gly Pro Phe Leu Asp Val Leu Arg Ser Ala Gln Glu Ala Ile Val Leu
 65                  70                  75                  80 ccg ccg ttc gtg gcc atc gcg gtg cgc ccg cgc ccg gga gtt tgg gag     288
Pro Pro Phe Val Ala Ile Ala Val Arg Pro Arg Pro Gly Val Trp Glu
                 85                  90                  95 tac gtc cgc gtc aac gtt cac gag ctc agc gtc gag cag ctc aca gtc     336
Tyr Val Arg Val Asn Val His Glu Leu Ser Val Glu Gln Leu Thr Val
            100                 105                 110 tcg gag tac ctc cgc ttc aag gag gag ctt gtc gac ggc cag cac aat     384
Ser Glu Tyr Leu Arg Phe Lys Glu Glu Leu Val Asp Gly Gln His Asn
        115                 120                 125 gat ccc tac gtt ctc gag ctt gac ttc gag ccg ttc aat gtc tca gtc     432
Asp Pro Tyr Val Leu Glu Leu Asp Phe Glu Pro Phe Asn Val Ser Val
    130                 135                 140 cca cgc cca aat cgg tca tca tct att gga aac ggt gtg cag ttc ctc     480
Pro Arg Pro Asn Arg Ser Ser Ser Ile Gly Asn Gly Val Gln Phe Leu
145                 150                 155                 160 aac cga cac ttg tcc tca atc atg ttc cgc aac agg gat tgc ttg gag     528
Asn Arg His Leu Ser Ser Ile Met Phe Arg Asn Arg Asp Cys Leu Glu
                165                 170                 175 ccc ctg ttg gat ttc ctc cgt ggc cac cgg cac aag ggg cat gtt atg     576
Pro Leu Leu Asp Phe Leu Arg Gly His Arg His Lys Gly His Val Met
            180                 185                 190 atg ctt aat gat aga ata caa agc ttg ggg agg ctt cag tct gtg ctg     624
Met Leu Asn Asp Arg Ile Gln Ser Leu Gly Arg Leu Gln Ser Val Leu
        195                 200                 205 acc aaa gct gag gag cac ttg tca aag ctc cct gct gac aca cca tac     672
Thr Lys Ala Glu Glu His Leu Ser Lys Leu Pro Ala Asp Thr Pro Tyr
    210                 215                 220 tca caa ttt gct tat aaa ttt caa gag tgg ggc ctg gag aaa ggt tgg     720
Ser Gln Phe Ala Tyr Lys Phe Gln Glu Trp Gly Leu Glu Lys Gly Trp
225                 230                 235                 240 ggt gat aca gca gga cat gtt ttg gaa atg atc cat ctc ctt cta gac     768
Gly Asp Thr Ala Gly His Val Leu Glu Met Ile His Leu Leu Leu Asp
                245                 250                 255 atc att cag gcg cca gac cca tct acc cta gag aaa ttc ttg ggg agg     816
Ile Ile Gln Ala Pro Asp Pro Ser Thr Leu Glu Lys Phe Leu Gly Arg
            260                 265                 270
```

```
atc ccc atg att ttt aac gtt gtt gtg gta tcc cct cat gga tac ttt     864
Ile Pro Met Ile Phe Asn Val Val Val Val Ser Pro His Gly Tyr Phe
        275                 280                 285 ggt caa gct aat gta tta ggc ttg cca gac aca gga gga cag atc gtc     912
Gly Gln Ala Asn Val Leu Gly Leu Pro Asp Thr Gly Gly Gln Ile Val
    290                 295                 300 tat ata ctg gac caa gtc cgt gca cta gaa aat gag atg gtt ctc cgt     960
Tyr Ile Leu Asp Gln Val Arg Ala Leu Glu Asn Glu Met Val Leu Arg
305                 310                 315                 320 tta aag aaa caa ggg ctt gat gtt tcc cca aag att ctc att gtt act    1008
Leu Lys Lys Gln Gly Leu Asp Val Ser Pro Lys Ile Leu Ile Val Thr
                325                 330                 335 cgg ctg ata cca gat gca aaa gga aca tca tgc aat cag cgg ctt gag    1056
Arg Leu Ile Pro Asp Ala Lys Gly Thr Ser Cys Asn Gln Arg Leu Glu
            340                 345                 350 aga att agt gga aca cag cat act tac ata tta cga gtt ccc ttc aga    1104
Arg Ile Ser Gly Thr Gln His Thr Tyr Ile Leu Arg Val Pro Phe Arg
        355                 360                 365 aat gaa aat ggg ata ctt aag aaa tgg ata tca aga ttt gat gtg tgg    1152
Asn Glu Asn Gly Ile Leu Lys Lys Trp Ile Ser Arg Phe Asp Val Trp
    370                 375                 380 cca tat ctg gaa aca ttt gct gag gat gct gct ggt gaa att gct gct    1200
Pro Tyr Leu Glu Thr Phe Ala Glu Asp Ala Ala Gly Glu Ile Ala Ala
385                 390                 395                 400 gaa tta caa ggt act cca gac ttc ata att gga aac tac agt gat gga    1248
Glu Leu Gln Gly Thr Pro Asp Phe Ile Ile Gly Asn Tyr Ser Asp Gly
                405                 410                 415 aat ctt gtg gcg tca ttg cta tct tac aag atg gga att acc cag tgc    1296
Asn Leu Val Ala Ser Leu Leu Ser Tyr Lys Met Gly Ile Thr Gln Cys
            420                 425                 430 aac att gct cat gct ctg gaa aag act aag tat cca gat tca gac ata    1344
Asn Ile Ala His Ala Leu Glu Lys Thr Lys Tyr Pro Asp Ser Asp Ile
        435                 440                 445 ttt tgg aag aat ttc gat gag aag tac cat ttc tcc tgc cag ttc act    1392
Phe Trp Lys Asn Phe Asp Glu Lys Tyr His Phe Ser Cys Gln Phe Thr
    450                 455                 460 gct gat ata att gct atg aac aat gct gat ttt atc atc acc agc aca    1440
Ala Asp Ile Ile Ala Met Asn Asn Ala Asp Phe Ile Ile Thr Ser Thr
465                 470                 475                 480 tac caa gaa att gct gga agc aaa aat act gtt gga cag tat gag agt    1488
Tyr Gln Glu Ile Ala Gly Ser Lys Asn Thr Val Gly Gln Tyr Glu Ser
                485                 490                 495 cat act gcc ttt act ctg cct ggt ctg tac cga gtt gtc cat ggg atc    1536
His Thr Ala Phe Thr Leu Pro Gly Leu Tyr Arg Val Val His Gly Ile
            500                 505                 510 gat gtc ttc gat cca aag ttc aat ata gtc tct cct gga gct gac atg    1584
Asp Val Phe Asp Pro Lys Phe Asn Ile Val Ser Pro Gly Ala Asp Met
        515                 520                 525 tcc ata tac ttt cca cat acc gag aag gcc aag cga ctc acc tct ctt    1632
Ser Ile Tyr Phe Pro His Thr Glu Lys Ala Lys Arg Leu Thr Ser Leu
    530                 535                 540 cat ggt tca atc gaa aat ttg att tat gac ccg gag caa aac gat gaa    1680
His Gly Ser Ile Glu Asn Leu Ile Tyr Asp Pro Glu Gln Asn Asp Glu
545                 550                 555                 560 cac att ggg cat ctg gat gac cgg tca aag ccc atc ctc ttc tcc atg    1728
His Ile Gly His Leu Asp Asp Arg Ser Lys Pro Ile Leu Phe Ser Met
                565                 570                 575 gca aga ctc gac agg gtg aag aac ata aca ggg ctg gtc gaa gct ttt    1776
Ala Arg Leu Asp Arg Val Lys Asn Ile Thr Gly Leu Val Glu Ala Phe
```

```
                        580             585             590
gct aag tgc gct aag ctg agg gag ctg gta aac ctt gtc gtc gtt gcc    1824
Ala Lys Cys Ala Lys Leu Arg Glu Leu Val Asn Leu Val Val Val Ala
        595             600             605 ggg tac aat gat gtc aac aag tcc aag gac agg gaa gag atc gcg gag    1872
Gly Tyr Asn Asp Val Asn Lys Ser Lys Asp Arg Glu Glu Ile Ala Glu
610             615             620 ata gag aag atg cat gaa ctc atc aag acc cac aac ttg ttc ggg cag    1920
Ile Glu Lys Met His Glu Leu Ile Lys Thr His Asn Leu Phe Gly Gln
625             630             635             640 ttc cgc tgg atc tct gcc cag aca aac agg gcc cgt aac ggc gag ctc    1968
Phe Arg Trp Ile Ser Ala Gln Thr Asn Arg Ala Arg Asn Gly Glu Leu
            645             650             655 tat cgc tac atc gct gat acc cat ggt gct ttc gta cag ccg gcc ttg    2016
Tyr Arg Tyr Ile Ala Asp Thr His Gly Ala Phe Val Gln Pro Ala Leu
        660             665             670 tat gaa gcg ttc ggt ctc acc gtc gtt gag gcc atg acc tgt ggg ctt    2064
Tyr Glu Ala Phe Gly Leu Thr Val Val Glu Ala Met Thr Cys Gly Leu
    675             680             685 cct act ttc gcg acg ctc cat gga ggt cca gct gag atc ata gag cat    2112
Pro Thr Phe Ala Thr Leu His Gly Gly Pro Ala Glu Ile Ile Glu His
    690             695             700 ggc gtc tcg ggc ttc cac att gac ccg tac cac ccc gaa cag gct gtt    2160
Gly Val Ser Gly Phe His Ile Asp Pro Tyr His Pro Glu Gln Ala Val
705             710             715             720 aat ctg atg gcc gac ttc ttc gac cgg tgc aag caa gac cca gat cac    2208
Asn Leu Met Ala Asp Phe Phe Asp Arg Cys Lys Gln Asp Pro Asp His
            725             730             735 tgg gtg aat ata tct gga gca ggg ctg cag cgc ata tac gag aag tac    2256
Trp Val Asn Ile Ser Gly Ala Gly Leu Gln Arg Ile Tyr Glu Lys Tyr
        740             745             750 aca tgg aag ata tac tca gag agg ttg atg aca ctg gcc ggg gtc tac    2304
Thr Trp Lys Ile Tyr Ser Glu Arg Leu Met Thr Leu Ala Gly Val Tyr
    755             760             765 ggt ttc tgg aag tac gtg tcg aag ctc gag agg ctg gag acg agg cgc    2352
Gly Phe Trp Lys Tyr Val Ser Lys Leu Glu Arg Leu Glu Thr Arg Arg
770             775             780 tac ctt gag atg ttc tac ata ctg aag ttc cgc gag ctg gcg aag acc    2400
Tyr Leu Glu Met Phe Tyr Ile Leu Lys Phe Arg Glu Leu Ala Lys Thr
785             790             795             800 gtg ccg ctt gca att gac caa ccg cag tag cttgcgcaac tgcgactgcg      2450
Val Pro Leu Ala Ile Asp Gln Pro Gln *
            805 tagcacttgg tacaagactg aaacctgaag gaccttcagt aatttaggcg cggcagacgg  2510 tagccaataa aatgtccgg agctgaactg gttttttatt atgtacataa tggcagtata   2570 acaaaattac tgaaggcagg tgggttgcag ttgtgtgttc gttactgttt actgtattat  2630 gtcaagctgt cggctgcaat ttctttgctg gcaagccgca ggcactggtg aagtgctgat  2690 aaatacatca tattctgttg acctgtgaaa aaaaaaaaa aaaaaaaaa aaaaaaggg     2750 cggccgc                                                            2757

<210> SEQ ID NO 12
<211> LENGTH: 809
<212> TYPE: PRT
<213> ORGANISM: Zea mays

<400> SEQUENCE: 12

Met Ser Ala Pro Lys Leu Asn Arg Asn Ala Ser Ile Arg Asp Arg Val
```

-continued

```
  1               5               10              15
Glu Asp Thr Leu His Ala His Arg Asn Glu Leu Val Ala Leu Leu Ser
                20              25              30
Lys Tyr Val Asn Lys Gly Lys Gly Ile Leu Gln Pro His His Ile Leu
                35              40              45
Asp Ala Leu Asp Glu Val Gln Gly Ser Gly Val Arg Ala Leu Ala Glu
              50              55              60
Gly Pro Phe Leu Asp Val Leu Arg Ser Ala Gln Ala Ile Val Leu
 65             70              75              80
Pro Pro Phe Val Ala Ile Ala Val Arg Pro Arg Pro Gly Val Trp Glu
                85              90              95
Tyr Val Arg Val Asn Val His Glu Leu Ser Val Glu Gln Leu Thr Val
              100             105             110
Ser Glu Tyr Leu Arg Phe Lys Glu Glu Leu Val Asp Gly Gln His Asn
              115             120             125
Asp Pro Tyr Val Leu Glu Leu Asp Phe Glu Pro Phe Asn Val Ser Val
              130             135             140
Pro Arg Pro Asn Arg Ser Ser Ile Gly Asn Gly Val Gln Phe Leu
145             150             155             160
Asn Arg His Leu Ser Ser Ile Met Phe Arg Asn Arg Asp Cys Leu Glu
                165             170             175
Pro Leu Leu Asp Phe Leu Arg Gly His Arg His Lys Gly His Val Met
                180             185             190
Met Leu Asn Asp Arg Ile Gln Ser Leu Gly Arg Leu Gln Ser Val Leu
                195             200             205
Thr Lys Ala Glu Glu His Leu Ser Lys Leu Pro Ala Asp Thr Pro Tyr
              210             215             220
Ser Gln Phe Ala Tyr Lys Phe Gln Glu Trp Gly Leu Glu Lys Gly Trp
225             230             235             240
Gly Asp Thr Ala Gly His Val Leu Glu Met Ile His Leu Leu Leu Asp
                245             250             255
Ile Ile Gln Ala Pro Asp Pro Ser Thr Leu Glu Lys Phe Leu Gly Arg
                260             265             270
Ile Pro Met Ile Phe Asn Val Val Val Ser Pro His Gly Tyr Phe
                275             280             285
Gly Gln Ala Asn Val Leu Gly Leu Pro Asp Thr Gly Gly Gln Ile Val
              290             295             300
Tyr Ile Leu Asp Gln Val Arg Ala Leu Glu Asn Glu Met Val Leu Arg
305             310             315             320
Leu Lys Lys Gln Gly Leu Asp Val Ser Pro Lys Ile Leu Ile Val Thr
                325             330             335
Arg Leu Ile Pro Asp Ala Lys Gly Thr Ser Cys Asn Gln Arg Leu Glu
                340             345             350
Arg Ile Ser Gly Thr Gln His Thr Tyr Ile Leu Arg Val Pro Phe Arg
                355             360             365
Asn Glu Asn Gly Ile Leu Lys Lys Trp Ile Ser Arg Phe Asp Val Trp
              370             375             380
Pro Tyr Leu Glu Thr Phe Ala Glu Asp Ala Ala Gly Glu Ile Ala Ala
385             390             395             400
Glu Leu Gln Gly Thr Pro Asp Phe Ile Ile Gly Asn Tyr Ser Asp Gly
                405             410             415
Asn Leu Val Ala Ser Leu Leu Ser Tyr Lys Met Gly Ile Thr Gln Cys
              420             425             430
```

```
Asn Ile Ala His Ala Leu Glu Lys Thr Lys Tyr Pro Asp Ser Asp Ile
        435                 440                 445

Phe Trp Lys Asn Phe Asp Glu Lys Tyr His Phe Ser Cys Gln Phe Thr
    450                 455                 460

Ala Asp Ile Ile Ala Met Asn Asn Ala Asp Phe Ile Ile Thr Ser Thr
465                 470                 475                 480

Tyr Gln Glu Ile Ala Gly Ser Lys Asn Thr Val Gly Gln Tyr Glu Ser
                485                 490                 495

His Thr Ala Phe Thr Leu Pro Gly Leu Tyr Arg Val Val His Gly Ile
            500                 505                 510

Asp Val Phe Asp Pro Lys Phe Asn Ile Val Ser Pro Gly Ala Asp Met
        515                 520                 525

Ser Ile Tyr Phe Pro His Thr Glu Lys Ala Lys Arg Leu Thr Ser Leu
    530                 535                 540

His Gly Ser Ile Glu Asn Leu Ile Tyr Asp Pro Glu Gln Asn Asp Glu
545                 550                 555                 560

His Ile Gly His Leu Asp Asp Arg Ser Lys Pro Ile Leu Phe Ser Met
                565                 570                 575

Ala Arg Leu Asp Arg Val Lys Asn Ile Thr Gly Leu Val Glu Ala Phe
            580                 585                 590

Ala Lys Cys Ala Lys Leu Arg Glu Leu Val Asn Leu Val Val Val Ala
        595                 600                 605

Gly Tyr Asn Asp Val Asn Lys Ser Lys Asp Arg Glu Glu Ile Ala Glu
    610                 615                 620

Ile Glu Lys Met His Glu Leu Ile Lys Thr His Asn Leu Phe Gly Gln
625                 630                 635                 640

Phe Arg Trp Ile Ser Ala Gln Thr Asn Arg Ala Arg Asn Gly Glu Leu
                645                 650                 655

Tyr Arg Tyr Ile Ala Asp Thr His Gly Ala Phe Val Gln Pro Ala Leu
            660                 665                 670

Tyr Glu Ala Phe Gly Leu Thr Val Val Glu Ala Met Thr Cys Gly Leu
        675                 680                 685

Pro Thr Phe Ala Thr Leu His Gly Gly Pro Ala Glu Ile Ile Glu His
    690                 695                 700

Gly Val Ser Gly Phe His Ile Asp Pro Tyr His Pro Glu Gln Ala Val
705                 710                 715                 720

Asn Leu Met Ala Asp Phe Phe Asp Arg Cys Lys Gln Asp Pro Asp His
                725                 730                 735

Trp Val Asn Ile Ser Gly Ala Gly Leu Gln Arg Ile Tyr Glu Lys Tyr
            740                 745                 750

Thr Trp Lys Ile Tyr Ser Glu Arg Leu Met Thr Leu Ala Gly Val Tyr
        755                 760                 765

Gly Phe Trp Lys Tyr Val Ser Lys Leu Glu Arg Leu Glu Thr Arg Arg
    770                 775                 780

Tyr Leu Glu Met Phe Tyr Ile Leu Lys Phe Arg Glu Leu Ala Lys Thr
785                 790                 795                 800

Val Pro Leu Ala Ile Asp Gln Pro Gln
                805

<210> SEQ ID NO 13
<211> LENGTH: 347
<212> TYPE: DNA
<213> ORGANISM: Sorghum propinquum
```

-continued

```
<400> SEQUENCE: 13
cgccagtcgc cagtcgccac agccacacca caccacacta gccgcggccg cgggtaggag      60
cgcgcgcggc gcggcggaac gacccaccgg tggcggcagc catgtctgcc ccgaagctga     120
accgcaacgc gagcatccgg gaccgcgtcg aggacaccct ccacgcgcac cgcaacgagc     180
tcgtcgccct cctctccaag tacgtgaaca aggggaaggg catcctgcag ccgcaccaca     240
tcctcgacgc gctcgacgag gtccagggct ccggggtccg cgcgctcgcc gagggaccct     300
tcctcgacgt cctccgctcc gcgcaggagg cgatcgtgct gccgccg                  347
```

ISOLATED SUCROSE SYTHASE POLYNUCLEOTIDES AND USES THEREOF

CROSS-REFERENCE TO RELATED APPLICATIONS

This application claims the benefit of and incorporates by reference U.S. Provisional Application No. 60/270,777, filed Feb. 22, 2001.

FIELD OF THE INVENTION

The present invention relates generally to plant molecular biology. More specifically, it relates to nucleic acids and methods for modulating their expression in plants.

BACKGROUND OF THE INVENTION

Chemical composition and mechanical properties of plant materials determine to a major extent how those plant materials are utilized. Cell wall content and composition account for most of the variation in mechanical strength of plant tissues. Also, cell wall composition is a major determinant of silage quality. Cell walls constitute a major sink in the vegetative parts of plants, accounting, for example, for approximately 80% of the corn stalk (FIG. 1). For the whole corn plant, including grain, cell wall accounts for approximately 35–40% of the dry mass.

Cellulose, the most abundant organic molecule on Earth, is made at the plasma membrane and directly deposited into the cell wall [Ray, et al., (1976), Ber. Deutsch. Bot. Ges. Bd. 89:121–146]. By inter- and intra-chain hydrogen bonding, β-1,4-glucan chains form para-crystalline microfibrils which eventually form ribbons and fibers, giving cellulose a very high tensile strength [Niklas (1992), "Plant biomechanics: An engineering approach to plant form and function," The University of Chicago Press, p. 607]. Because of its paracrystalline nature, cellulose makes a disproportionately greater contribution toward tensile strength of plant tissues than it would if it were amorphous in nature.

Cell wall of a maize stalk consists mostly of cellulose and hemicellulose, with lignin constituting a minor proportion, i.e., ~10% (FIG. 1). In a study conducted on three contrasting pairs of hybrids, we have determined that cellulose concentration in a unit length of stalk below the ear is correlated with tensile strength of the stalk (FIG. 2). Stalk lodging is a major problem in maize, accounting for significant yield losses. Increasing cellulose concentration in the wall will result in a mechanically stronger tissue, reducing the problem of stalk lodging.

The rate of cellulose synthesis exerts major control on the formation of the rest of the wall, as cellulose is its dominant constituent (FIG. 1). Formation of UDP-glucose, the substrate for cellulose synthase (CesA), occurs through two pathways in plants: one through UDP-glucose pyrophosphorylase (UGPase) and the other through sucrose synthase (FIG. 3). Sucrose synthase (SuSy) catalyzes the reversible reaction:

Sucrose+UDP⇌UDP–Glucose+Fructose

Thus, the cleavage reaction provides the precursor for synthesis of starch and cellulose. SuSy uses the energy of the glycosidic bond from sucrose to make UDP-glucose from UDP, releasing fructose in the process; fructose can then be channeled into UDP-glucose by the UGPase pathway (FIG. 3). While sucrose synthase has historically been considered active in the cytoplasm of plant cells, Amor et al. found tight association of about half of the total cellular SuSy with the plasma membrane in cotton and suggested that SuSy might channel substrate directly from sucrose to CesA [Amor, et al., (1995), "A membrane-associated form of sucrose synthase and its potential role in synthesis of cellulose and callose in plants," *Proc. Natl. Acad. Sci. USA* 92:9353–9357]. Therefore, in a sink tissue, such as growing corn stalk, sucrose synthase provides an economical route for the formation of UDP-glucose from sucrose. In contrast, the UGPase pathway utilizes more energy in the form of nucleotide triphosphates to produce UDP-glucose from hexose sugars.

Until the present invention, only two sucrose synthase genes have been known in maize, shrunken-1 (Sh1) and constitutive sucrose synthase (Sus1), both of which map to chromosome 9 [Huang, et al. (1994), "Complete nucleotide sequence of the maize (*Zea mays* L.) sucrose synthase 2 cDNA," *Plant Physiology Rockville* 104:293–294; McCarty, et al. (1986), "The cloning, genetic mapping and expression of the constitutive sucrose synthase locus of maize," *Proc. Natl. Acad. Sci. USA* 83:9099–9103; Werr, et al. (1985), "Structure of the sucrose synthase (EC 2.4.1.13) gene on chromosome 9 of *Zea mays*," *EMBO J.* 4:1373–1380]. These paralogs encode the sucrose synthase isozymes SS1 and SS2, respectively.

Membrane-associated SuSy has also been found in carrot and maize [Carlson, et al. (1996), "Evidence for plasma membrane-associated forms of sucrose synthase in maize," *Molecular and General Genetics* 252:303–310; Sturm, et al. (1999), "Tissue-specific expression of two genes for sucrose synthase in carrot (daucus carota L.)," *Plant Molecular Biology* 39:349–360]. Both the known forms of SuSy in maize were found to be associated with the plasma membrane fraction from developing endosperm. Interestingly, Sh1 was suggested to play a greater role in cell wall formation than the constitutive sucrose synthase (Sus1), which was purported to contribute more toward starch formation [Chourey, et al. (1998), "Genetic evidence that the two isozymes of sucrose synthase present in developing maize endosperm are critical, one for cell integrity and the other for starch biosyntheses," *Molecular and General Genetics* 259:88–96]. SuSy is known to become reversibly phosphorylated at a unique seryl residue [Huber, et al. (1996), "Phosphorylation of serine-15 of maize leaf sucrose synthase," *Plant Physiology Rockville* 112:793–802]. The unphosphorylated form, because of its relatively greater surface hydrophobicity, is favored to bind the membrane [Winter, et al. (1997), "Membrane association of sucrose synthase: Changes during the graviresponse and possible control by protein phosphorylation," *FEBS Letters* 420: 151–155].

Sucrose synthase has been suggested to channel substrate to the matrix polysaccharide synthases, based on association with Golgi and a previous report of its involvement in cellulose synthesis [Buckeridge, et al., (1999), "The mechanism of synthesis of a mixed-linkage (1fwdarw3), (1fwdarw4) beta-D-glucan in maize. Evidence for multiple sites of glucosyl transfer in the synthase complex," *Plant-Physiology-Rockville* 120:1105–1116 ]. Direct evidence for the contribution of SuSy toward substrate generation for cellulose synthesis was provided by Nakai et al [Nakai, et al. (1999), "Enhancement of cellulose production by expression of sucrose synthase in *Acetobacter xylinum*," *Proc. Natl. Acad. Sci. USA* 96:14–18]. They obtained a higher level of cellulose production in *Acetobacter xylinum* upon expression of mung bean sucrose synthase. This bacterium lacks sucrose synthase so is limited to only the UGPase branch of the pathway for making UDP-glucose (FIG. 3). Expression of sucrose synthase also led to a higher level of UDP-glucose and a lower level of UDP in the bacterium, as would be expected based on the pathway in FIG. 3.

Down-regulation of SuSy by antisense approach in carrot reduced the growth rate [Tang, et al. (1999), "Antisense repression of sucrose synthase in carrot (Daucus carota L.) affects growth rather than sucrose partitioning," *Plant-Molecular-Biology* 41:465–479]. Levels of UDP-glucose and cellulose were reduced in the sink tissues in comparison to the wild type plants, again implying a role for SuSy in substrate production for cellulose synthesis. In work with the TUSC (Trait Utility System for Corn; see U.S. Pat. No. 5,962,764, incorporated herein by reference) SuSy mutant, knocking out the constitutive sucrose synthase led to a reduced cellulose concentration in the walls, as well as reduced amount of total cell wall (Example 8).

Formation of UDP-glucose from sucrose requires half as much energy as if it were to be made from hexose sugars (FIG. 3). Not even accounting for the channeling effect, as suggested by Amor et al. [1995, supra], involvement of sucrose synthase in providing substrate to cellulose synthase would lead to improved productivity, particularly under stressful conditions, as the energy conserved by this pathway could be used for other cellular processes. Over expression of sucrose synthase under the control of a stalk-preferred promoter in plants could lead to a greater synthesis of cellulose, thereby strengthening the stalk. Therefore, there is a need in the art for sucrose synthases that can be over-expressed under these conditions.

Sucrose phosphate synthase may participate in UDP-glucose metabolism, but its role appears to be more to dissipate energy in the sink tissues than to economize the use of sugars (FIG. 3). For example, assuming that all the fructose-6-phosphate and UDP-glucose are derived from the SuSy pathway, at least one ATP is consumed to make sucrose from these two substrates only for the former to be cycled through SuSy again. On the other extreme, i.e., when all the UDP-glucose and fructose-6-phosphate are derived from hexose sugars, formation of sucrose by sucrose phosphate synthase utilizes 3 NTP per sucrose molecule produced, two to form UDP-glucose from a hexose sugar and 1 to phosphorylate fructose. In other words, involvement of sucrose phosphate synthase would consume an extra 1–3 NTP per molecule of sucrose to be incorporated into cellulose, which means a consumption of 3–5 net NTP for this process.

Four NTP would be needed per sucrose molecule for its complete conversion to UDP-glucose even if all the sucrose were first to be cleaved by invertases, and hexoses were the only sugars available. Even invertases dissipate (waste) the energy of the glycosidic bond which is otherwise used by sucrose synthase to form UDP-glucose from UDP. Sucrose phosphate synthase may, however, be important in mediating the formation of sucrose from excess hexoses for transport to other sinks, such as developing ear. This could be important after the deposition of cellulose into the walls of stalk tissue has slowed down.

Each hexose sugar molecule, upon complete breakdown by glycolysis, citric acid cycle, and oxidative phosphorylation, produces 36 ATP equivalents of energy. As discussed above, each hexose upon activation into UDP-glucose uses 1 ATP if carried through the SuSy pathway and 2 ATP if through the UGPase pathway (FIG. 3). The fraction of sugar utilized, assuming all other processes to be constant, in supporting this conversion is:

$$\frac{p + 2q}{36}$$

where p is the proportion of substrates produced by the action of SuSy; q represents substrates produced from hexose sugars; and p+q=1. If all the UDP-glucose were to be derived from the SuSy-mediated pathway, then 2.8% of the sugar would be utilized in producing energy to support this reaction. If, on the other hand, hexose was the starting point for all the UDP-glucose produced, then 5.6% of the sugar would be utilized in generating energy for this series of reactions.

Routing of any proportion, n, of the sugars through the sucrose phosphate synthase pathway would reduce the efficiency further still as the NTP utilized for this cycling would be in addition to the ones used in making UDP-glucose from sucrose or hexose. The following expression provides an estimate of the reduction in efficiency:

$$\frac{(p + 2q) + n(p + 3q)}{36}$$

If 50% of the sugar is cycled through the sucrose phosphate synthase pathway and the substrates for this enzyme are derived in equal proportion (i.e., p=q=0.5) from the SuSy and UGPase pathways then, without including the energy needed for the sucrose phosphate synthase pathway to operate, this would translate into 4.2% of the sugar converted into cellulose being utilized for energy generation to support this process. If, however, the energy utilized by the sucrose phosphate synthase pathway, based on above assumptions, is taken into account, then this number increases to ~7%, a full 70% extra energy than if no sugar were cycled through this pathway. That is equivalent to burning nearly 3 extra bushels of sugar for every 100 bushels converted into polysaccharides.

Thus, the production of cellulose through the sucrose synthase pathway is the most economical means available to plants. One of skill in the art would know of the involvement of sucrose synthase in cellulose formation in plants. However, the present invention teaches that this enzyme is important in supplying substrate for cellulose synthesis (Example 8).

As stalk composition contributes to numerous quality factors important in maize breeding, what is needed in the art are products and methods for manipulating cellulose concentration in the cell wall and thereby altering plant stalk quality to provide, for example, increased standability. It would be desirable to over-express sucrose synthase, preferably under the control of a stalk-preferred promoter, to improve stalk strength in maize.

Another attribute of importance is grain handling ability, i.e., reducing grain breakage during combining, transport, and movement into storage. Grain strength in cereals such as wheat and barley is mainly derived from the pericarp, which allows for a softer endosperm. It would be desirable to increase cellulose in the pericarp by over-expressing sucrose synthase under the control of a pericarp-specific promoter.

The present invention provides these and other advantages.

SUMMARY OF THE INVENTION

We have identified a heretofore unknown cDNA for a third sucrose synthase gene, Sus3, from a proprietary genome database (see ZmSus3, Examples 9 and 10). Sus3 maps to the short arm of chromosome 1 (bin 1.04). The ESTs for this gene are found in a variety of tissues, albeit at a much lower frequency than those for Sus1, indicating that this gene, like Sus1, is expressed constitutively.

Generally, it is the object of the present invention to provide nucleic acids and proteins relating to sucrose synthase 3 (Sus3). It is an object of the present invention to provide transgenic plants comprising the nucleic acids of the present invention, and methods for modulating, in a transgenic plant, expression of the nucleic acids of the present invention. More specifically, it is also an object of the present invention to manipulate cellulose concentration in the cell wall and to alter grain quality and/or plant stalk quality. It is another object of the present invention to alter expression of sucrose synthase in a plant to improve stalk quality and/or stalk strength. It is another object of this invention to alter expression of sucrose synthase in a plant to improve grain quality and/or grain strength.

Therefore, in one aspect the present invention relates to an isolated nucleic acid comprising a member selected from the group consisting of (a) a polynucleotide having a specified sequence identity to a polynucleotide of the present invention; (b) a polynucleotide which is complementary to the polynucleotide of (a); and, (c) a polynucleotide comprising a specified number of contiguous nucleotides from a polynucleotide of (a) or (b). The isolated nucleic acid can be DNA.

In other aspects the present invention relates to: 1) recombinant expression cassettes, comprising a nucleic acid of the present invention operably linked to a promoter, 2) a host cell into which has been introduced the recombinant expression cassette, and 3) a transgenic plant comprising the recombinant expression cassette. The host cell and plant are optionally from maize, wheat, rice, or soybean.

BRIEF DESCRIPTION OF THE DRAWINGS

FIG. 7. Table of data from analysis of cellulose and cell wall content in Sus1 mutants.

FIGS. 8a and 8b. Multiple alignment of maize sucrose synthase amino acid sequences. SEQ ID NOs: 2,5, and 7.

FIGS. 9a–9f. Multiple alignment of maize sucrose synthase polynucleotides. SEQ ID NOs: 1,4, and 6.

FIG. 10. Sequence of SEQ ID NO: 13, Sorghum EST having GenBank Accession No. BF481989. The ATG encoding the first methionine in the open reading frame of SEQ ID NO: 11 is shown in bold. The sequence utilized to provide the deduced full length Sus3 sequence is underlined.

FIG. 11. The combination of maize and sorghum Sus3 sequences used to create SEQ ID NO: 11. The portions of sorghum sequence selected from SEQ ID NO: 13 and the selected maize sequence selected from SEQ ID NO: 1 are shown separately. Before combining the sequence from SEQ ID NO: 1 with the shown sorghum sequence from SEQ ID NO: 13 to create SEQ ID NO: 11, the nucleotides in SEQ ID NO 1 shown as highlighted with strikethrough should be removed removed.

DETAILED DESCRIPTION OF THE INVENTION

Overview

A. Nucleic Acids and Protein of the Present Invention

The polynucleotide sequences of SEQ ID. NOS. 1 and 11, and polypeptide sequences of SEQ ID. NOS. 2 and 12, represent a polynucleotide and polypeptide of the present invention. A nucleic acid of the present invention comprises a polynucleotide of the present invention. A protein of the present invention comprises a polypeptide of the present invention.

B. Exemplary Utilities of the Present Invention

The present invention provides utility in such exemplary applications as manipulating cellulose concentration in the cell wall and thereby altering plant stalk quality to provide, for example, increased standability. It would be desirable to over-express sucrose synthase, preferably under the control of a stalk-preferred promoter, to improve plant strength in maize.

Another attribute of importance is grain handling ability, i.e., reducing grain breakage during combining, transport, and movement into storage. Grain strength in cereals such as wheat and barley is mainly derived from the pericarp, which allows for a softer endosperm. It would be desirable to increase cellulose in the pericarp by over-expressing sucrose synthase, preferably under the control of a pericarp-preferred promoter.

C. Exemplary Preferable Embodiments

Figure 1:
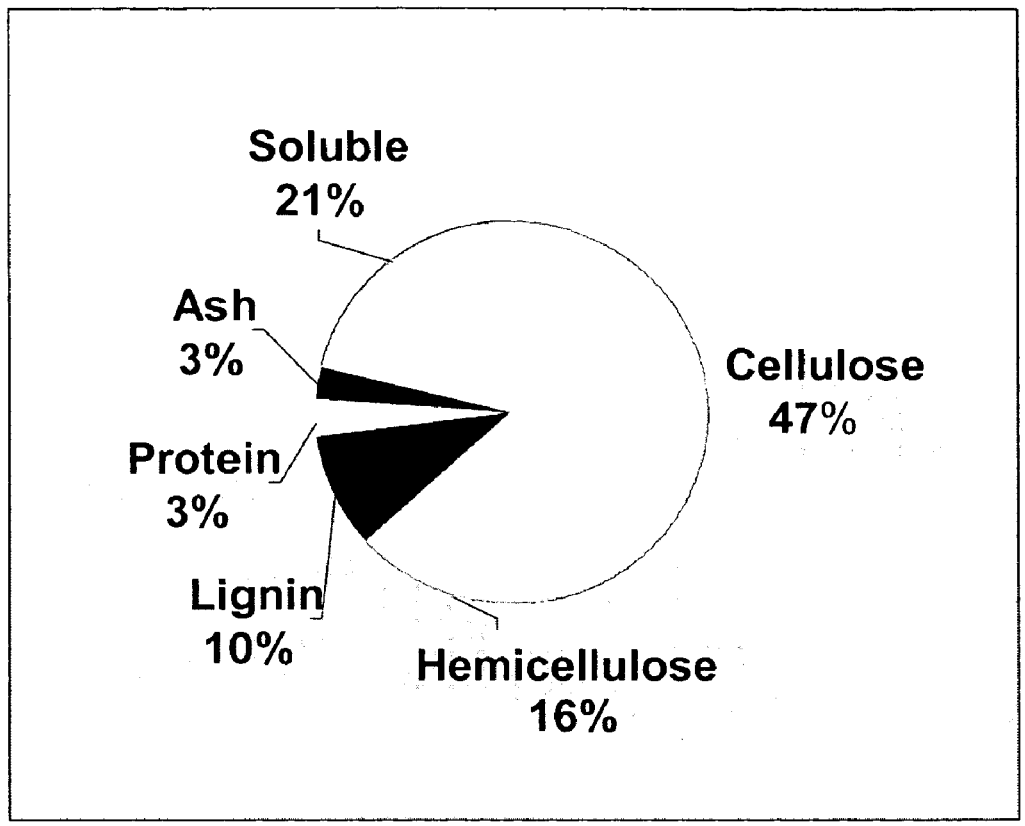
FIG. 1. Circle graph depicting chemical composition of corn stalk. Two internodes, 2nd and 3rd below the ear, were harvested 60 days after flowering, dried and ground. Structural dry matter was determined by washing the powdered material with buffer followed by methanol:chloroform. Cellulose was determined gravimetrically by Updegraff's method by boiling the ground material or structural dry matter in acetic acid-nitric acid mix, and lignin by Klason method. Ash was determined by incinerating the samples in a 600° C. oven for 4 hours. Protein was assumed to be around 3%. Soluble component was derived by subtracting structural dry matter from total dry matter. Hemicellulose concentration was estimated by subtracting cellulose, lignin, protein, and ash from structural dry matter. Mature monocot walls are known to have very little pectin.
Figure 2:
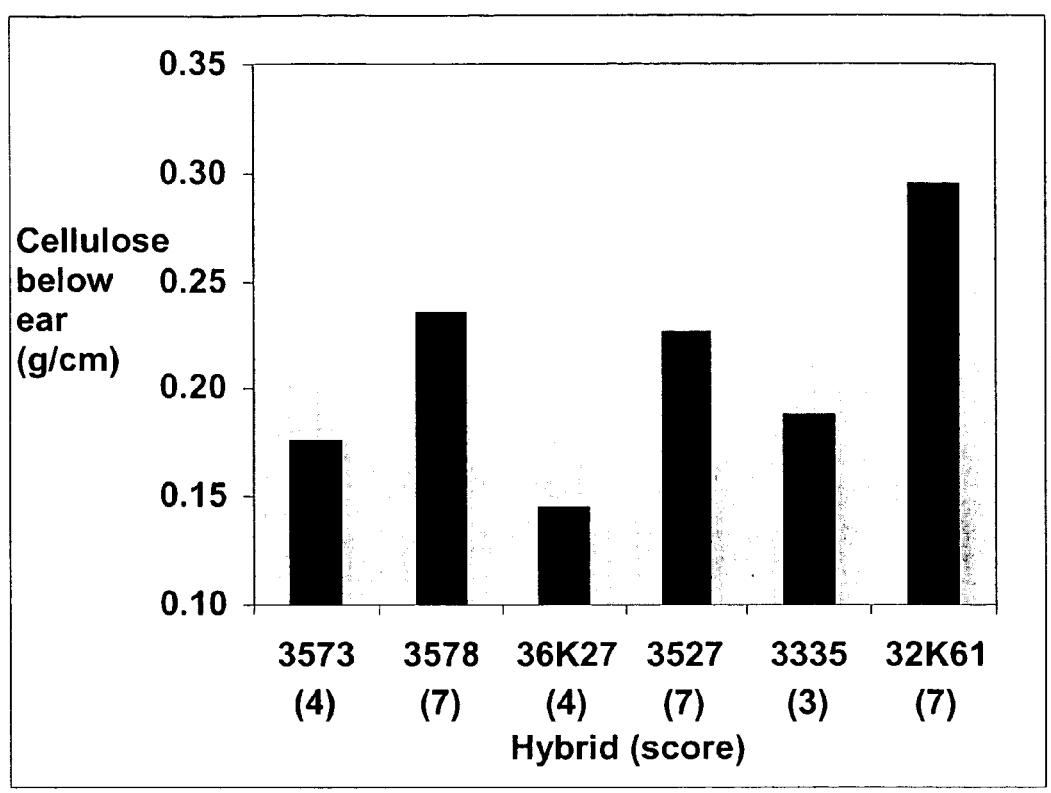
FIG. 2. Bar graph depicting amount of cellulose in corn hybrids. Two internodes, 2nd and 3rd below the ear, were harvested 60 days after flowering, dried and ground. Structural dry matter was determined by washing the powdered material with buffer followed by methanol:chloroform. Cellulose was determined gravimetrically by Updegraff's method by boiling the ground material or structural dry matter in acetic acid-nitric acid mix, and lignin by Klason method. Ash was determined by incinerating the samples in a 600° C. oven for 4 hours. Protein was assumed to be around 3%. Soluble component was derived by subtracting structural dry matter from total dry matter. Hemicellulose concentration was estimated by subtracting cellulose, lignin, protein, and ash from structural dry matter. Mature monocot walls are known to have very little pectin.
Figure 3:
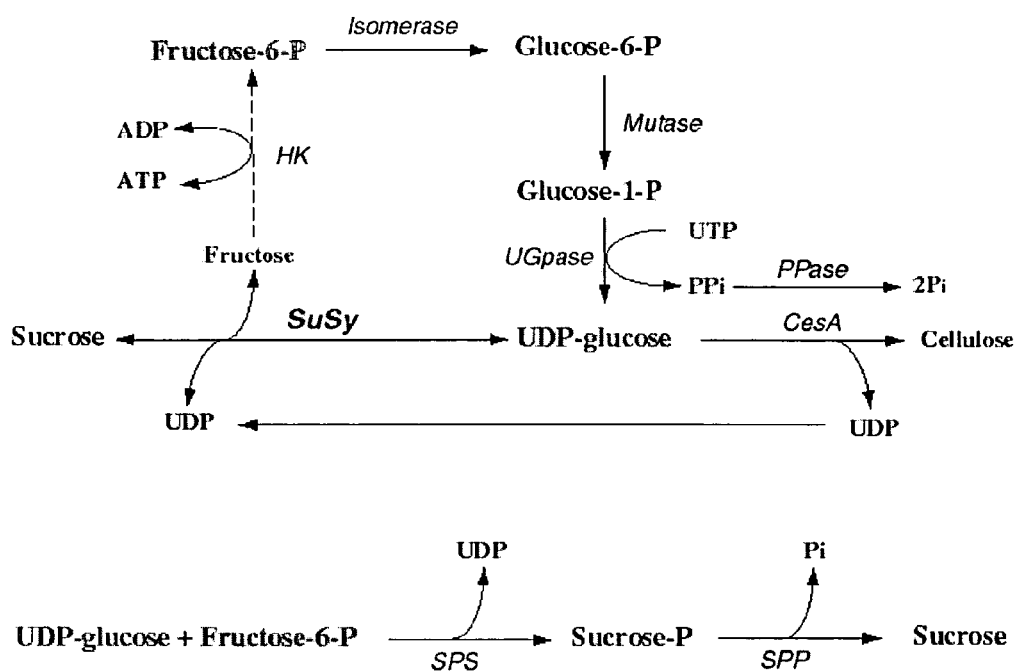
FIG. 3. Schematic representation of partial pathways for synthesis of UDP-glucose. Abbreviations: ATP, adenosine triphosphate; CesA, cellulose synthase; HK, hexokinase; PPase, pyrophosphatase; PPi, pyrophosphate; SPP, sucrose phosphate phosphatase; SPS, sucrose phosphate synthase; SuSy, sucrose synthase; UDPG or UDP-Glucose, uridine diphosphate glucose; UGPase, UDPG pyrophosphorylase; UTP, uridine triphosphate.
Figure 4:
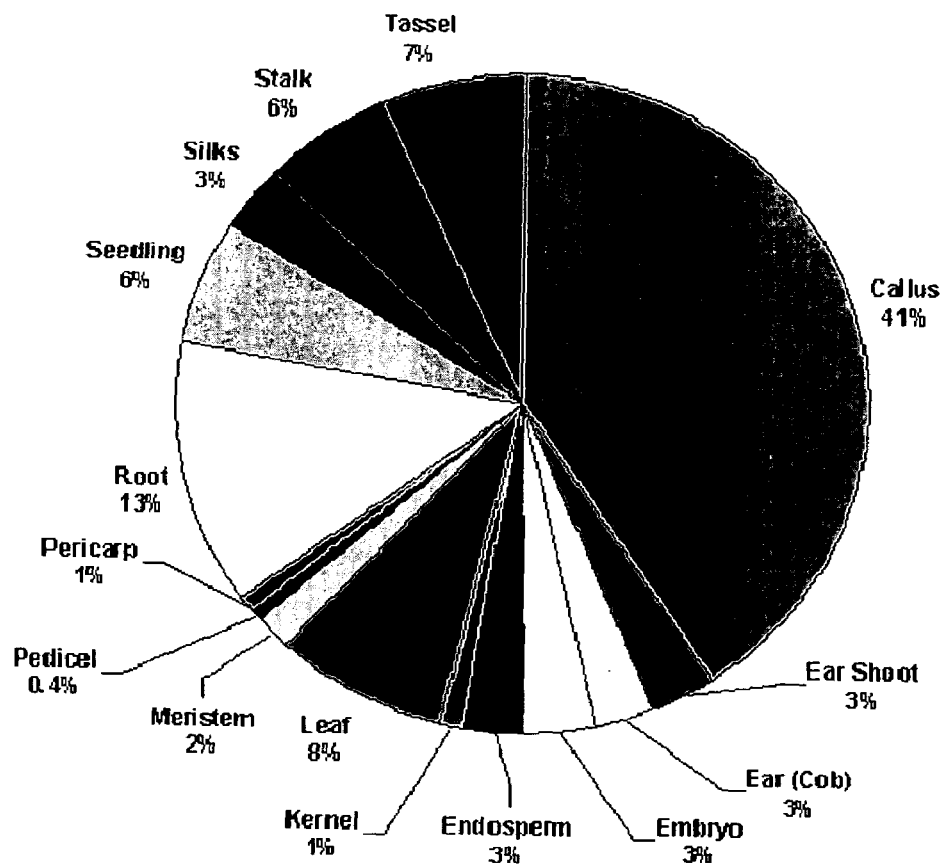
FIG. 4. Circle graph depicting distribution of Sus1 ESTs in maize tissues. For Sus1, 230 ESTs were found in the genome database consisting of approximately 400,000 total ESTs.
Figure 5:
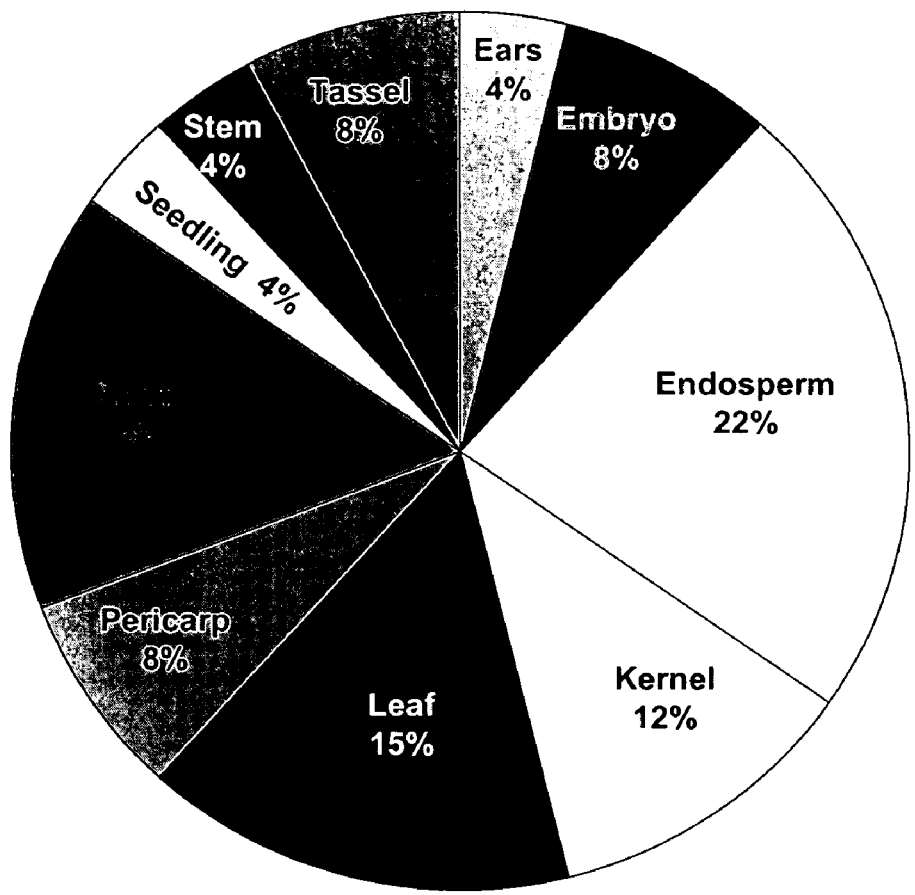
FIG. 5. Circle graph depicting distribution of Sus3 ESTs in maize tissues. Out of approximately 400,000 ESTs in the genome database, 26 ESTs were found for Sus3.

While the various preferred embodiments are disclosed throughout the specification, exemplary preferable embodiments include the following:

(i) Expression pattern of sucrose synthase genes. Sus1 is represented by approximately 230 and Sus3 by about 26 ESTs found in Pioneer Hi-Bred International, Inc. proprietary genome databases, which include data from numerous proprietary nucleic acid libraries representing plant tissues at a variety of developmental stages. These EST findings act as a sort of electronic Northern and provide evidence that Sus3 is expressed at a much lower level than Sus1 (FIGS. 4 and 5). Both Sus1 and Sus3 are expressed in a variety of tissues and therefore can be classified as constitutive sucrose synthases. However, Sus3 appears to be somewhat preferentially expressed in the kernel, where 50% of its ESTs are found. In comparison, only about 10% of ESTs (15% when the callus tissue is excluded) for Sus1 are found in the kernel tissue. One striking difference is that Sus3 does not seem to be expressed in the callus tissue at all, whereas about half of the ESTs for Sus1 are found in libraries derived from this tissue.

(ii) Promoters. Preferred promoters include but are not limited to: the Actin-1 promoter from rice (McElroy et al. 1990, Plant Cell 2:163–171); the rice tungro baciliform virus promoter (Yin et al. 1995, Plant Journal 7(6): 969–980); the *Agrobacterium rhizogenes* ROlC promoter and the maize Sh promoter (Graham et al. 1997, Plant Molecular Biology 33:729–735); the tissue-preferred promoter described in U.S. Pat. No. 5,986,174, herein incorporated by reference; S2A promoter from maize or alfalfa (Abrahams et al. 1995, Plant Molecular Biology 27(3): 513–528); maize Adh2 promoter elements (Paul et al. 1994, Plant Journal 5(4):523–533); CoYMV promoter (Medberry et al. 1992, Plant Cell 4(2): 185–192); bean grp 1.8 promoter and regulatory elements therein (Keller et al. 1994, Plant Molecular Biology 26(2):747–756); tomato prosystemin promoter (Jacinto et al. 1997, Planta 203(4):406–412); maize gene Hrgp promoter (Menossi et al. 1997, Plant Science 125 (2):189–200); maize Sus1 promoter (Huang, X. et al. (1998) Euphytica 103(1):17–21); promoter of maize gene P-rr (Sidorenko et al. 1999, Plant Molecular Biology, 39:11–19), and maize promoter mZE40-2 described in U.S. patent application Ser. No. 09/666,179.

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges recited within the specification are inclusive of the numbers defining the range and include each integer within the defined range. Amino acids may be referred to herein by either their commonly known three letter symbols or by the one-letter symbols recommended by the IUPAC-IUBMB Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5$^{th}$ edition, 1993). The terms defined below are more fully defined by reference to the specification as a whole. Section headings provided throughout the specification are not limitations to the various objects and embodiments of the present invention.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

The terms "alter" or "modify" or "modulate", with respect to expression of nucleic acids or proteins, include reference to methods of up-regulation and down-regulation. Up-regulation may be achieved, for example, through increased transcription and/or translation of a gene of interest, through means such as operably linking the gene of interest to a promoter sequence which favors increased transcription; through adding or over-expressing a necessary substrate in a metabolic pathway; through the blocking of antagonistic molecules; or by other means known to one of skill in the art. Down-regulation may be achieved, for example, through antisense technology (see, e.g., Sheehy et al., *Proc. Nat'l. Acad. Sci.* (USA) 85: 8805–8809 (1988); and Shewmaker, Hiatt, et al., U.S. Pat. No. 5,759,829); through RNA interference (see Napoli et al., *The Plant Cell* 2: 279–289 (1990); U.S. Pat. No. 5,034,323; Sharp, *Genes & Development* 13:139–141(1999); Zamore et al., *Cell* 101:25–33 (2000); Montgomery et al., *PNAS USA* 95:15502–15507 (1998); virus-induced gene silencing (Burton, et al., *The Plant Cell* 12:691–705 (2000); Baulcombe, *Curr. Opn. Plant Bio.* 2:109–113 (1999)); through the use of target-RNA-specific ribozymes (Haseloff et al., *Nature* 334: 585–591 (1988)); through hairpin-loop suppression (Smith et al., *Nature* 407: 319–320 (2000)); and through other methods known to those of skill in the art. Said up- or down-regulation may be directed preferentially, such as within certain tissues, under particular environmental conditions, and/or at certain stages of plant development.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate Macronucleus, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. *Nucl. Acids Res.* 17: 477–498 (1989)). Thus, the maize preferred codon for a particular amino acid may be derived from known gene sequences from maize. Maize codon usage for 28 genes from maize plants is listed in Table 4 of Murray et al., supra.

As used herein "full-length sequence" in reference to a specified polynucleotide or its encoded protein means having the entire amino acid sequence of, a native (non-synthetic), endogenous, biologically (e.g., structurally or catalytically) active form of the specified protein. Methods to determine whether a sequence is full-length are well known in the art including such exemplary techniques as northern or western blots, primer extension, S1 protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNNAUGG, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by human intervention.

By "host cell" is meant a cell which contains a vector and supports the replication and/or expression of the vector. Host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The term "introduced" includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA). The term includes such nucleic acid introduction means as "transfection", "transformation" and "transduction".

The term "isolated" refers to material, such as a nucleic acid or a protein, which is substantially free from components that normally accompany or interact with it as found in its naturally occurring environment. The isolated material optionally comprises material not found with the material in its natural environment, or if the material is in its natural environment, the material has been synthetically (non-naturally) altered by human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., WO 93/22443. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

As used herein, "nucleic acid" includes reference to a deoxyribonucleotide or ribonucleotide polymer, or chimeras thereof, in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism, tissue, or of a cell type from that organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning-A Laboratory Manual*, 2nd ed., Vol. 1–3 (1989); and *Current Protocols in Molecular Biology*, F. M. Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants and their progeny; plant cells; plant parts or organs, such as embryos, pollen, ovules, seeds, flowers, kernels, ears, cobs, leaves, husks, stalks, stems, roots, root tips, anthers, silk and the like. Plant cell, as used herein, further includes, without limitation, cells obtained from or found in: seeds, suspension cultures, embryos, meristematic regions, callus tissue, leaves, roots, shoots, gametophytes, sporophytes, pollen, and microspores. Plant cells can also be understood to include modified cells, such as protoplasts, obtained from the aforementioned tissues. The class of plants which can be used in the methods of the invention is generally as broad as the class of higher plants amenable to transformation techniques, including both monocotyledonous and dicotyledonous plants. A particularly preferred plant is Zea mays.

As used herein, "polynucleotide" includes reference to a deoxyribopolynucleotide, ribopolynucleotide, or chimeras or analogs thereof that have the essential nature of a natural deoxy- or ribo-nucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. Further, this invention contemplates the use of both the methionine-containing and the methionine-less amino terminal variants of the protein of the invention.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria, which comprise genes expressed in plant cells such as Agrobacterium or Rhizobium. Examples of promoters under developmental control include promoters that preferentially initiate transcription in certain tissues, such as leaves, roots, or seeds. Such promoters are referred to as "tissue preferred". Promoters which initiate transcription only, or almost only, in certain tissue are referred to as "tissue specific". A "cell type" specific promoter primarily drives expression in certain cell types in one or more organs, for example, vascular cells in roots or leaves. A promoter may have spatial or temporal specificity, capable of initiating transcription preferentially with respect to conditions of space or time. An "inducible" or "repressible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of human intervention. The term "recombinant" as used herein does not encompass the alteration of the cell or vector by naturally occurring events (e.g., spontaneous mutation, natural transformation/transduction/transposition) such as those occurring without human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "stringent conditions" or "stringent hybridization conditions" includes reference to conditions under which a probe will selectively hybridize to its target sequence, to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1 % SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267–284 (1984): $T_m$=81.5° C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. Hybridization and/or wash conditions can be applied for at least 10, 30, 60, 90, 120, or 240 minutes. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and Current Protocols in Molecular Biology, Chapter 2, Ausubel, et al., Eds., Greene Publishing and Wiley-Interscience, New York (1995).

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in introduction of a polynucleotide of the present invention into a host cell. Vectors are often replicons. Expression vectors permit transcription of a nucleic acid inserted therein.

The following terms are used to describe the sequence relationships between a polynucleotide/polypeptide of the present invention and a reference polynucleotide/polypeptide: (a) "reference sequence", (b) "comparison window", (c) "sequence identity", and (d) "percentage of sequence identity".

(a) As used herein, "reference sequence" is a defined sequence used as a basis for sequence comparison with a polynucleotide/polypeptide of the present invention. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acid residues in length, and optionally can be 30, 40, 50, 100, or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well known in the art. Optimal alignment of sequences for comparison may be conducted by the local homology algorithm of Smith and Waterman, *Adv. Appl. Math.* 2: 482 (1981); by the homology alignment algorithm of Needleman and Wunsch, *J. Mol. Biol.* 48: 443 (1970); by the search for similarity method of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237–244 (1988); Higgins and Sharp, *CABIOS* 5: 151–153 (1989); Corpet, et al., *Nucleic Acids Research* 16: 10881–90 (1988); Huang, et al., *Computer Applications in*

*the Biosciences* 8: 155–65 (1992), and Pearson, et al., *Methods in Molecular Biology* 24: 307–331 (1994).

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995); Altschul et al., *J. Mol. Biol.*, 215:403–410 (1990); and, Altschul et al., *Nucleic Acids Res.* 25:3389–3402 (1997).

Software for performing BLAST analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5877 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149–163 (1993)) and XNU (Claverie and States, *Comput Chem.*, 17:191–201 (1993)) low-complexity filters can be employed alone or in combination.

Unless otherwise stated, nucleotide and protein identity/similarity values provided herein are calculated using GAP (GCG Version 10) under default values.

GAP (Global Alignment Program) can also be used to compare a polynucleotide or polypeptide of the present invention with a reference sequence. GAP uses the algorithm of Needleman and Wunsch (*J. Mol. Biol.* 48: 443–453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 100. Thus, for example, the gap creation and gap extension penalties can each independently be: 0, 1, 2, 3, 4, 5, 6, 7, 8, 9, 10, 15, 20, 30, 40, 50, 60 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) *Proc. Natl. Acad. Sci. USA* 89:10915).

Multiple alignment of the sequences can be performed using the CLUSTAL method of alignment (Higgins and Sharp (1989) CABIOS. 5:151–153) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4:11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Utilities

The present invention provides, among other things, compositions and methods for altering or modulating the level of polynucleotides and polypeptides of the present invention in plants. In particular, the polynucleotides and polypeptides of the present invention can be expressed temporally or spatially, e.g., at developmental stages, in tissues, and/or in quantities, which are uncharacteristic of non-recombinantly engineered plants.

The present invention also provides isolated nucleic acids comprising polynucleotides of sufficient length and complementarity to a polynucleotide of the present invention to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring up-regulation of expression or changes in enzyme activity in screening assays of compounds, for detection of any number of allelic variants (polymorphisms), orthologs, or paralogs of the gene, or for site directed mutagenesis in eukaryotic cells (see, e.g., U.S. Pat. No. 5,565,350). The isolated nucleic acids of the present invention can also be used for recombinant expression of their encoded polypeptides, or for use as immunogens in the preparation and/or screening of antibodies. The isolated nucleic acids of the present invention can also be employed for use in sense or antisense suppression of one or more genes of the present invention in a host cell, tissue, or plant. Attachment of chemical agents which bind, intercalate, cleave and/or cross-link to the isolated nucleic acids of the present invention can also be used to modulate transcription or translation.

The present invention also provides isolated proteins comprising a polypeptide of the present invention (e.g., preproenzyme, proenzyme, or enzymes). The present invention also provides proteins comprising at least one epitope from a polypeptide of the present invention. The proteins of the present invention can be employed in assays for enzyme agonists or antagonists of enzyme function, or for use as immunogens or antigens to obtain antibodies specifically immunoreactive with a protein of the present invention. Such antibodies can be used in assays for expression levels, for identifying and/or isolating nucleic acids of the present invention from expression libraries, for identification of homologous polypeptides from other species, or for purification of polypeptides of the present invention.

The isolated nucleic acids and polypeptides of the present invention can be used over a broad range of plant types, particularly monocots such as the species of the family Gramineae including Hordeum, Secale, Oryza, Triticum, Sorghum (e.g., *S. bicolor*) and Zea (e.g., *Z. mays*), and dicots such as Glycine.

The isolated nucleic acid and proteins of the present invention can also be used in species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browallia, Pisum, Phaseolus, Lolium*, and *Avena*.

Nucleic Acids

The present invention provides, among other things, isolated nucleic acids of RNA, DNA, and analogs and/or chimeras thereof, comprising a polynucleotide of the present invention.

A polynucleotide of the present invention is inclusive of:

(a) an isolated polynucleotide encoding SEQ ID NO: 2 or SEQ ID NO:12, including exemplary polynucleotides of the present invention;

(b) an isolated polynucleotide which is the product of amplification from a plant nucleic acid library using primer pairs which selectively hybridize under stringent conditions to loci within a polynucleotide of the present invention;

(c) an isolated polynucleotide which selectively hybridizes to a polynucleotide of (a) or (b);

(d) an isolated polynucleotide having a specified sequence identity with polynucleotides of (a), (b), or (c);

(e) an isolated polynucleotide encoding a protein having a specified number of contiguous amino acids from a prototype polypeptide, wherein the protein is specifically recognized by antisera elicited by presentation of the protein and wherein the protein does not detectably immunoreact to antisera which have been fully immunosorbed with the protein;

(f) complementary sequences of polynucleotides of (a), (b), (d), or (e); and (g) an isolated polynucleotide comprising at least a specific number of contiguous nucleotides from a polynucleotide of (a), (b), (c), (d), (e), or (f);

(h) an isolated polynucleotide from a full-length enriched cDNA library having the physico-chemical property of selectively hybridizing to a polynucleotide of (a), (b), (c), (d), (e), (f), or (g);

(i) an isolated polynucleotide made by the process of: 1) providing a full-length enriched nucleic acid library, 2) selectively hybridizing the polynucleotide to a polynucleotide of (a), (b), (c), (d), (e), (f), (g), or (h), thereby isolating the polynucleotide from the nucleic acid library.

A. Polynucleotides Encoding A Polypeptide of the Present Invention

As indicated in (a), above, the present invention provides isolated nucleic acids comprising a polynucleotide of the present invention, wherein the polynucleotide encodes a polypeptide of the present invention. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Thus, each silent variation of a nucleic acid which encodes a polypeptide of the present invention is implicit in each described polypeptide sequence and is within the scope of the present invention. Accordingly, the present invention includes polynucleotides of the present invention and polynucleotides encoding a polypeptide of the present invention.

B. Polynucleotides Amplified from a Plant Nucleic Acid Library

As indicated in (b), above, the present invention provides an isolated nucleic acid comprising a polynucleotide of the present invention, wherein the polynucleotides are amplified, under nucleic acid amplification conditions, from a plant nucleic acid library. Nucleic acid amplification conditions for each of the variety of amplification methods are well known to those of ordinary skill in the art. The plant nucleic acid library can be constructed from a monocot such as a cereal crop. Exemplary cereals include corn, sorghum, alfalfa, canola, wheat, and rice. The plant nucleic acid library can also be constructed from a dicot such as soybean. Zea mays lines B73, A632, BMS, W23, and Mo17 are known and publicly available. Other publicly known and available maize lines can be obtained from the Maize Genetics Cooperation (Urbana, Ill.). Wheat lines are available from the Wheat Genetics Resource Center (Manhattan, Kans.).

The nucleic acid library may be a cDNA library, a genomic library, or a library generally constructed from nuclear transcripts at any stage of intron processing. cDNA libraries can be normalized to increase the representation of relatively rare cDNAs. In optional embodiments, the cDNA library is constructed using an enriched full-length cDNA synthesis method. Examples of such methods include Oligo-Capping (Maruyama, K. and Sugano, S. *Gene* 138: 171–174,1994), Biotinylated CAP Trapper (Carninci, et al. *Genomics* 37: 327–336,1996), and CAP Retention Procedure (Edery, E., Chu, L. L., et al. *Molecular and Cellular Biology* 15: 3363–3371, 1995). Rapidly growing tissues or rapidly dividing cells are preferred for use as an mRNA source for construction of a cDNA library. Growth stages of corn are described in "How a Corn Plant Develops," Special Report No. 48, Iowa State University of Science and Technology Cooperative Extension Service, Ames, Iowa, February 1993; http://www.ag.iastate.edu/departments/agronomy/comtitle.html.

A polynucleotide of this embodiment (or subsequences thereof) can be obtained, for example, by using amplification primers which are selectively hybridized and primer extended, under nucleic acid amplification conditions, to at least two sites within a polynucleotide of the present invention, or to two sites within the nucleic acid which flank and comprise a polynucleotide of the present invention, or to a site within a polynucleotide of the present invention and a site within the nucleic acid which comprises it. Methods for obtaining 5' and/or 3' ends of a vector insert are well known in the art. See, e.g., RACE (Rapid Amplification of Complementary Ends) as described in Frohman, M. A., in PCR Protocols: A Guide to Methods and Applications, M. A. Innis, D. H. Gelfand, J. J. Sninsky, T. J. White, Eds. (Academic Press, Inc., San Diego), pp. 28–38 (1990)); see also, U.S. Pat. No. 5,470,722, and *Current Protocols in Molecular Biology*, Unit 15.6, Ausubel, et al., Eds., Greene Publishing and Wiley-Interscience, New York (1995); Frohman and Martin, *Techniques* 1:165 (1989).

Optionally, the primers are complementary to a subsequence of the target nucleic acid which they amplify but may have a sequence identity ranging from about 85% to 99% relative to the polynucleotide sequence to which they are designed to anneal. As those skilled in the art will appreciate, the sites to which the primer pairs will selectively hybridize are chosen such that a single contiguous nucleic acid can be formed under the desired nucleic acid amplification conditions. The primer length in nucleotides is selected from the group of integers consisting of from at least 15 to 50. Thus, the primers can be at least 15, 18, 20, 25, 30, 40, or 50 nucleotides in length. Those of skill will recognize that a lengthened primer sequence can be employed to increase specificity of binding (i.e., annealing) to a target sequence. A non-annealing sequence at the 5'end of a primer (a "tail") can be added, for example, to introduce a cloning site at the terminal ends of the amplicon.

The amplification products can be translated using expression systems well known to those of skill in the art. The resulting translation products can be confirmed as polypeptides of the present invention by, for example, assaying for the appropriate catalytic activity (e.g., specific activity and/or substrate specificity), or verifying the presence of one or more epitopes which are specific to a polypeptide of the present invention. Methods for protein synthesis from PCR derived templates are known in the art and available commercially. See, e.g., Amersham Life Sciences, Inc, Catalog '97, p.354.

C. Polynucleotides Which Selectively Hybridize to a Polynucleotide of (A) or (B)

As indicated in (c), above, the present invention provides isolated nucleic acids comprising polynucleotides of the present invention, wherein the polynucleotides selectively hybridize, under selective hybridization conditions, to a polynucleotide of sections (A) or (B) as discussed above. Thus, the polynucleotides of this embodiment can be used for isolating, detecting, and/or quantifying nucleic acids comprising the polynucleotides of (A) or (B). For example, polynucleotides of the present invention can be used to identify, isolate, or amplify partial or full-length clones in a deposited library. In some embodiments, the polynucleotides are genomic or cDNA sequences isolated or otherwise complementary to a cDNA from a dicot or monocot nucleic acid library. Exemplary species of monocots and dicots include, but are not limited to: maize, canola, soybean, cotton, wheat, sorghum, sunflower, alfalfa, oats, sugar cane, millet, barley, and rice. The cDNA library comprises at least 50% to 95% full-length sequences (for example, at least 50%, 60%, 70%, 80%, 90%, or 95% full-length sequences). The cDNA libraries can be normalized to increase the representation of rare sequences. See, e.g., U.S. Pat. No. 5,482,845. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% to 80% sequence identity and can be employed to identify orthologous or paralogous sequences.

D. Polynucleotides Having a Specific Sequence Identity with the Polynucleotides of (A), (B) or (C)

As indicated in (d), above, the present invention provides isolated nucleic acids comprising polynucleotides of the present invention, wherein the polynucleotides have a specified identity at the nucleotide level to a polynucleotide as disclosed in sections (A), (B), or (C), above. Identity can be calculated using, for example, the BLAST, CLUSTALW, or GAP algorithms under default conditions. The percentage of identity to a reference sequence is at least 50% and, rounded upwards to the nearest integer, can be expressed as an integer selected from the group of integers consisting of from 50 to 99. Thus, for example, the percentage of identity to a reference sequence can be at least 60%, 70%, 75%, 80%, 85%, 90%, or 95%.

Optionally, the polynucleotides of this embodiment will encode a polypeptide that will share an epitope with a polypeptide encoded by the polynucleotides of sections (A), (B), or (C). Thus, these polynucleotides encode a first polypeptide which elicits production of antisera comprising antibodies which are specifically reactive to a second polypeptide encoded by a polynucleotide of (A), (B), or (C). However, the first polypeptide does not bind to antisera raised against itself when the antisera have been fully immunosorbed with the first polypeptide. Hence, the polynucleotides of this embodiment can be used to generate antibodies for use in, for example, the screening of expression libraries for nucleic acids comprising polynucleotides of (A), (B), or (C), or for purification of, or in immunoassays for, polypeptides encoded by the polynucleotides of (A), (B), or (C). The polynucleotides of this embodiment comprise nucleic acid sequences which can be employed for selective hybridization to a polynucleotide encoding a polypeptide of the present invention.

Screening polypeptides for specific binding to antisera can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5–100 amino acids long, and often from about 8 to 15 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT patent publication Nos. 91/17271, 91/18980, 91/19818, and 93/08278. Other systems for generating libraries of peptides have aspects of both in vitro chemical synthesis and recombinant methods. See, PCT Patent publication Nos. 92/05258, 92/14843, and 97/20078. See also, U.S. Pat. Nos. 5,658,754; and 5,643,768. Peptide display libraries, vectors, and screening kits are commercially available from such suppliers as Invitrogen (Carlsbad, Calif.).

E. Polynucleotides Encoding a Protein Having a Subsequence from a Prototype Polypeptide and Cross-Reactive to the Prototype Polypeptide As indicated in (e), above, the present invention provides isolated nucleic acids comprising polynucleotides of the present invention, wherein the polynucleotides encode a protein having a subsequence of contiguous amino acids from a prototype polypeptide of the present invention such as are provided in (a), above. The length of contiguous amino acids from the prototype polypeptide is selected from the group of integers consisting of from at least 10 to the number of amino acids within the prototype sequence. Thus, for example, the polynucleotide can encode a polypeptide having a subsequence having at least 10, 15, 20, 25, 30, 35, 40, 45, or 50, contiguous amino acids from the prototype polypeptide. Further, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The proteins encoded by polynucleotides of this embodiment, when presented as an immunogen, elicit the production of polyclonal antibodies which specifically bind to a prototype polypeptide such as but not limited to, a polypeptide encoded by the polynucleotide of (a) or (b), above. Generally, however, a protein encoded by a polynucleotide of this embodiment does not bind to antisera raised against the prototype polypeptide when the antisera have been fully immunosorbed with the prototype polypeptide. Methods of making and assaying for antibody binding specificity/affinity are well known in the art. Exemplary immunoassay formats include ELISA, competitive immunoassays, radioimmunoassays, Western blots, indirect immunofluorescent assays and the like.

In a preferred assay method, fully immunosorbed and pooled antisera which are elicited to the prototype polypeptide can be used in a competitive binding assay to test the protein. The concentration of the prototype polypeptide required to inhibit 50% of the binding of the antisera to the prototype polypeptide is determined. If the amount of the protein required to inhibit binding is less than twice the amount of the prototype protein, then the protein is said to specifically bind to the antisera elicited to the immunogen. Accordingly, the proteins of the present invention embrace allelic variants, conservatively modified variants, and minor recombinant modifications to a prototype polypeptide.

A polynucleotide of the present invention optionally encodes a protein having a molecular weight as the non-glycosylated protein within 20% of the molecular weight of the full-length non-glycosylated polypeptides of the present invention. Molecular weight can be readily determined by SDS-PAGE under reducing conditions. Optionally, the molecular weight is within 15% of a full-length polypeptide of the present invention, more preferably within 10% or 5%, and most preferably within 3%, 2%, or 1% of a full-length polypeptide of the present invention.

Optionally, the polynucleotides of this embodiment will encode a protein having a specific enzymatic activity at least 50%, 60%, 80%, or 90% of a cellular extract comprising the native, endogenous full-length polypeptide of the present invention. Further, the proteins encoded by polynucleotides of this embodiment will optionally have a substantially similar affinity constant ($K_m$) and/or catalytic activity (i.e., the microscopic rate constant, $k_{cat}$) as the native endogenous, full-length protein. Those of skill in the art will recognize that $k_{cat}/K_m$ value determines the specificity for competing substrates and is often referred to as the specificity constant. Proteins of this embodiment can have a $k_{cat}/K_m$ value at least 10% of a full-length polypeptide of the present invention as determined using the endogenous substrate of that polypeptide. Optionally, the $k_{cat}/K_m$ value will be at least 20%, 30%, 40%, 50%, and most preferably at least 60%, 70%, 80%, 90%, or 95% the $k_{cat}/K_m$ value of the full-length polypeptide of the present invention. Determination of $k_{cat}$, $K_m$, and $k_{cat}/K_m$ can be determined by any number of means well known to those of skill in the art. For example, the initial rates (i.e., the first 5% or less of the reaction) can be determined using rapid mixing and sampling techniques (e.g., continuous-flow, stopped-flow, or rapid quenching techniques), flash photolysis, or relaxation methods (e.g., temperature jumps) in conjunction with such exemplary methods of measuring as spectrophotometry, spectrofluorimetry, nuclear magnetic resonance, or radioactive procedures. Kinetic values are conveniently obtained using a Lineweaver-Burk or Eadie-Hofstee plot.

F. Polynucleotides Complementary to the Polynucleotides of (A)–(E)

As indicated in (f), above, the present invention provides isolated nucleic acids comprising polynucleotides complementary to the polynucleotides of paragraphs A-E, above. As those of skill in the art will recognize, complementary sequences base-pair throughout the entirety of their length with the polynucleotides of sections (A)–(E) (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

G. Polynucleotides Which are Subsequences of the Polynucleotides of (A)–(F)

As indicated in (g), above, the present invention provides isolated nucleic acids comprising polynucleotides which comprise at least 15 contiguous bases from the polynucleotides of sections (A) through (F) as discussed above. The length of the polynucleotide is given as an integer selected from the group consisting of from at least 15 to the length of the nucleic acid sequence from which the polynucleotide is a subsequence of. Thus, for example, polynucleotides of the present invention are inclusive of polynucleotides comprising at least 15, 20, 25, 30, 40, 50, 60, 75, or 100 contiguous nucleotides in length from the polynucleotides of (A)–(F). Optionally, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

Subsequences can be made by in vitro synthetic, in vitro biosynthetic, or in vivo recombinant methods. In optional embodiments, subsequences can be made by nucleic acid amplification. For example, nucleic acid primers will be constructed to selectively hybridize to a sequence (or its complement) within, or co-extensive with, the coding region.

The subsequences of the present invention can comprise structural characteristics of the sequence from which it is derived. Alternatively, the subsequences can lack certain structural characteristics of the larger sequence from which it is derived such as a poly (A) tail. Optionally, a subsequence from a polynucleotide encoding a polypeptide having at least one epitope in common with a prototype polypeptide sequence as provided in (a), above, may encode an epitope in common with the prototype sequence. Alternatively, the subsequence may not encode an epitope in common with the prototype sequence but can be used to isolate the larger sequence by, for example, nucleic acid hybridization with the sequence from which it is derived. Subsequences can be used to modulate or detect gene expression by introducing into the subsequences compounds which bind, intercalate, cleave and/or crosslink to nucleic acids. Exemplary compounds include acridine, psoralen, phenanthroline, naphthoquinone, daunomycin or chloroethylaminoaryl conjugates.

H. Polynucleotides From a Full-length Enriched cDNA Library Having the Physico-Chemical Property of Selectively Hybridizing to a Polynucleotide of (A)–(G)

As indicated in (h), above, the present invention provides an isolated polynucleotide from a full-length enriched cDNA library having the physico-chemical property of selectively hybridizing to a polynucleotide of paragraphs (A), (B), (C), (D), (E), (F), or (G) as discussed above. Methods of constructing full-length enriched cDNA libraries are known in the art and discussed briefly below. The cDNA library comprises at least 50% to 95% full-length sequences (for example, at least 50%, 60%, 70%, 80%, 90%, or 95% full-length sequences). The cDNA library can be constructed from a variety of tissues from a monocot or dicot at a variety of developmental stages. Exemplary species include maize, wheat, rice, canola, soybean, cotton, sorghum, sunflower, alfalfa, oats, sugar cane, millet, barley, and rice. Methods of selectively hybridizing, under selective hybridization conditions, a polynucleotide from a full-length enriched library to a polynucleotide of the present invention are known to those of ordinary skill in the art. Any number of stringency conditions can be employed to allow for selective hybridization. In optional embodiments, the stringency allows for selective hybridization of sequences having at least 70%, 75%, 80%, 85%, 90%, 95%, or 98% sequence identity over the length of the hybridized region. Full-length enriched cDNA libraries can be normalized to increase the representation of rare sequences.

I. Polynucleotide Products Made by a cDNA Isolation Process

As indicated in (I), above, the present invention provides an isolated polynucleotide made by the process of: 1) providing a full-length enriched nucleic acid library, 2) selectively hybridizing the polynucleotide to a polynucleotide of paragraphs (A), (B), (C), (D), (E), (F), (G, or (H) as discussed above, and thereby isolating the polynucleotide from the nucleic acid library. Full-length enriched nucleic acid libraries are constructed as discussed in paragraph (G) and below. Selective hybridization conditions are as discussed in paragraph (G). Nucleic acid purification procedures are well known in the art. Purification can be conveniently accomplished using solid-phase methods; such methods are well known to those of skill in the art and kits are available from commercial suppliers such as Advanced Biotechnologies (Surrey, UK). For example, a polynucleotide of paragraphs (A)–(H) can be immobilized to a solid support such as a membrane, bead, or particle. See, e.g., U.S. Pat. No. 5,667,976. The polynucleotide product of the present process is selectively hybridized to an immobilized polynucleotide and the solid support is subsequently isolated from non-hybridized polynucleotides by methods including, but not limited to, centrifugation, magnetic separation, filtration, electrophoresis, and the like.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot such as corn, rice, or wheat, or a dicot such as soybean.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. A polynucleotide of the present invention can be attached to a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known and extensively described in the art. For a description of various nucleic acids see, for example, Stratagene Cloning Systems, Catalogs 1999 (La Jolla, Calif.); and, Amersham Life Sciences, Inc, Catalog '99 (Arlington Heights, Ill.).

A. Recombinant Methods for Constructing Nucleic Acids

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library. Isolation of RNA, and construction of cDNA and genomic libraries is well known to those of ordinary skill in the art. See, e.g., *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995).

A1. Full-length Enriched cDNA Libraries

A number of cDNA synthesis protocols have been described which provide enriched full-length cDNA libraries. Enriched full-length cDNA libraries are constructed to comprise at least 60%, and more preferably at least 70%, 80%, 90% or 95% full-length inserts amongst clones containing inserts. The length of insert in such libraries can be at least 2, 3, 4, 5, 6, 7, 8, 9, 10 or more kilobase pairs. Vectors to accommodate inserts of these sizes are known in the art and available commercially. See, e.g., Stratagene's lambda ZAP Express (cDNA cloning vector with 0 to 12 kb cloning capacity). An exemplary method of constructing a greater than 95% pure full-length cDNA library is described by Carninci et al., *Genomics*, 37:327–336 (1996). Other methods for producing full-length libraries are known in the art. See, e.g., Edery et al., *Mol. Cell Biol.*,15 (6):3363–3371 (1995); and, PCT Application WO 96/34981.

A2. Normalized or Subtracted cDNA Libraries

A non-normalized cDNA library represents the mRNA population of the tissue it was made from. Since unique clones are out-numbered by clones derived from highly expressed genes their isolation can be laborious. Normalization of a cDNA library is the process of creating a library in which each clone is more equally represented. Construction of normalized libraries is described in Ko, *Nucl. Acids. Res.*, 18(19): 5705–5711 (1990); Patanjali et al., Proc. Natl. Acad. U.S.A., 88:1943–1947 (1991); U.S. Pat. Nos. 5,482, 685, 5,482,845, and 5,637,685. In an exemplary method described by Soares et al., normalization resulted in reduction of the abundance of clones from a range of four orders of magnitude to a narrow range of only 1 order of magnitude. *Proc. Natl. Acad. Sci. USA,* 91:9228–9232 (1994).

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining un-hybridized cDNA pool is enriched for sequences unique to that pool. See, Foote et al. in, *Plant Molecular Biology: A Laboratory Manual*, Clark, Ed., Springer-Verlag, Berlin (1997); Kho and Zarbl, *Technique,* 3(2):58–63 (1991); Sive and St. John, *Nucl. Acids Res.,* 16(22):10937 (1988); *Current Protocols in Molecular Biology*, Ausubel, et al., Eds., Greene Publishing and Wiley-Interscience, New York (1995); and, Swaroop et al., *Nucl. Acids Res.,* 19)8):1954 (1991). cDNA subtraction kits are commercially available. See, e.g., PCR-Select (Clontech, Palo Alto, Calif.).

To construct genomic libraries, large segments of genomic DNA are generated by fragmentation, e.g. using restriction endonucleases, and are ligated with vector DNA to form concatemers that can be packaged into the appropriate vector. Methodologies to accomplish these ends, and sequencing methods to verify the sequence of nucleic acids are well known in the art. Examples of appropriate molecular biological techniques and instructions sufficient to direct persons of skill through many construction, cloning, and screening methodologies are found in Sambrook, et al., *Molecular Cloning: A Laboratory Manual,* 2nd Ed., Cold Spring Harbor Laboratory Vols. 1–3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. The T4 gene 32 protein (Boehringer Mannheim) can be used to improve yield of long PCR products.

PCR-based screening methods have been described. Wilfinger et al. describe a PCR-based method in which the longest cDNA is identified in the first step so that incomplete clones can be eliminated from study. *BioTechniques,* 22(3): 481–486 (1997). Such methods are particularly effective in combination with a full-length cDNA construction methodology, above.

B. Synthetic Methods for Constructing Nucleic Acids

The isolated nucleic acids of the present invention can also be prepared by direct chemical synthesis by methods such as the phosphotriester method of Narang et al., *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.* 22: 1859–1862 (1981); the solid phase phosphoramidite triester method described by Beaucage and Caruthers, *Tetra. Letts.* 22(20): 1859–1862 (1981), e.g., using an automated synthesizer, e.g., as described in Needham-VanDevanter et al., *Nucleic Acids Res.,* 12: 6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is best employed for sequences of about 100 bases or less, longer sequences may be obtained by the ligation of shorter sequences.

Recombinant Expression Cassettes

The present invention further provides recombinant expression cassettes comprising a nucleic acid of the present invention. A nucleic acid sequence coding for the desired polypeptide of the present invention, for example a cDNA or a genomic sequence encoding a full length polypeptide of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'- promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, and the GRP1–8 promoter.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter which is inducible by hypoxia or cold stress, the Hsp70 promoter which is inducible by heat stress, and the PPDK promoter which is inducible by light.

Examples of promoters under developmental control include promoters that initiate transcription only, or preferentially, in certain tissues, such as leaves, roots, fruit, seeds, or flowers. Exemplary promoters include the anther specific promoter 5126 (U.S. Pat. Nos. 5,689,049 and 5,689,051), glob-1 promoter, and gamma-zein promoter. The operation of a promoter may also vary depending on its location in the genome. Thus, an inducible promoter may become fully or partially constitutive in certain locations.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter concentration and/or composition of the proteins of the present invention in a desired tissue. Thus, in some embodiments, the nucleic acid construct will comprise a promoter, functional in a plant cell, operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling et al., WO 93/22443), or isolated promoters can be introduced into a plant cell in the proper orientation and distance from a cognate gene of a polynucleotide of the present invention so as to control the expression of the gene. Gene expression can be modulated under conditions suitable for plant growth so as to alter the total concentration and/or alter the composition of the polypeptides of the present invention in plant cell. Thus, the present invention provides compositions, and methods for making, heterologous promoters and/or enhancers operably linked to a native, endogenous (i.e., non-heterologous) form of a polynucleotide of the present invention.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8: 4395–4405 (1988); Callis et al., *Genes Dev.* 1: 1183–1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, New York (1994). The vector comprising the sequences from a polynucleotide of the present invention will typically comprise a marker gene which confers a selectable phenotype on plant cells. Typical vectors useful for expression of genes in higher plants are well known in the art and include vectors derived from the tumor-inducing (Ti) plasmid of *Agrobacterium tumefaciens* described by Rogers et al., *Meth. in Enzymol.*, 153:253–277 (1987).

A polynucleotide of the present invention can be expressed in either sense or anti-sense orientation as desired. It will be appreciated that control of gene expression in either sense or anti-sense orientation can have a direct impact on the observable plant characteristics. Antisense technology can be conveniently used to inhibit gene expression in plants. To accomplish this, a nucleic acid segment from the desired gene is cloned and operably linked to a promoter such that the anti-sense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest, see, e.g., Sheehy et al., *Proc. Nat'l. Acad. Sci.* (*USA*) 85: 8805–8809 (1988); and Shewmaker, Hiatt, et al., U.S. Pat. No. 5,759,829.

Another method of suppression is sense suppression (i.e., co-supression). Introduction of nucleic acid configured in the sense orientation has been shown to be an effective means by which to block the transcription of target genes. For an example of the use of this method to modulate expression of endogenous genes see, Napoli et al., *The Plant Cell* 2: 279–289 (1990) and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., *Nature* 334: 585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985) 67:785–789. Iverson and Dervan also showed sequence-specific cleavage of single-stranded DNA mediated by incorporation of a modified nucleotide which was capable of activating cleavage (*J Am Chem Soc* (1987) 109:1241–1243). Meyer, R. B., et al., *J Am Chem Soc* (1989) 111:8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., *Biochemistry* (1988) 27:3197–3203. Use of crosslinking in triple-helix forming probes was also disclosed by Home, et al., *J Am Chem Soc* (1990) 112:2435–2437. Use of N4, N4-ethano-cytosine as an alkylating agent to crosslink to single-stranded oligonucleotides has also been described by Webb and Matteucci, *J Am Chem Soc* (1986) 108:2764–2765; *Nucleic Acids Res* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681,941.

Proteins

The isolated proteins of the present invention comprise a polypeptide having at least 10 amino acids from a polypeptide of the present invention (or conservative variants thereof) such as those encoded by any one of the polynucleotides of the present invention as discussed more fully above. The proteins of the present invention or variants thereof can comprise any number of contiguous amino acid residues from a polypeptide of the present invention, wherein that number is selected from the group of integers consisting of from 10 to the number of residues in a full-length polypeptide of the present invention. Optionally, this subsequence of contiguous amino acids is at least 15, 20, 25, 30, 35, or 40 amino acids in length, often at least 50, 60, 70, 80, or 90 amino acids in length. Further, the number of such subsequences can be any integer selected from the group consisting of from 1 to 20, such as 2, 3, 4, or 5.

The present invention further provides a protein comprising a polypeptide having a specified sequence identity/similarity with a polypeptide of the present invention. The percentage of sequence identity/similarity is an integer selected from the group consisting of from 50 to 99. Exemplary sequence identity/similarity values include 55%, 60%, 65%, 70%, 75%, 80%, 85%, 90%, and 95%. Sequence identity can be determined using, for example, the GAP, CLUSTALW, or BLAST algorithms.

As those of skill will appreciate, the present invention includes, but is not limited to, catalytically active polypeptides of the present invention (i.e., enzymes). Catalytically active polypeptides have a specific activity of at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art. Generally, the proteins of the present invention will, when presented as an immunogen, elicit production of an antibody specifically reactive to a polypeptide of the present invention. Further, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay. Thus, the proteins of the present invention can be employed as immunogens for constructing antibodies immunoreactive to a protein of the present invention for such exemplary utilities as immunoassays or protein purification techniques.

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or regulatable), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high-level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located purification sequences. Restriction sites or termination codons can also be introduced.

Synthesis of Proteins

The proteins of the present invention can be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in *The Peptides: Analysis, Synthesis, Biology. Vol. 2: Special Methods in Peptide Synthesis, Part A.*; Merrifield, et al., *J. Am. Chem. Soc.* 85: 2149–2156 (1963), and Stewart et al., *Solid Phase Peptide Synthesis,* 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide) are known to those of skill.

Purification of Proteins

The proteins of the present invention may be purified by standard techniques well known to those of skill in the art. Recombinantly produced proteins of the present invention can be directly expressed or expressed as a fusion protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice,* Springer-Verlag: New York (1982); Deutscher, *Guide to Protein Purification,* Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

Introduction of Nucleic Acids Into Host Cells

The method of introducing a nucleic acid of the present invention into a host cell is not critical to the instant invention. Transformation or transfection methods are conveniently used. Accordingly, a wide variety of methods have been developed to insert a DNA sequence into the genome of a host cell to obtain the transcription and/or translation of the sequence to effect phenotypic changes in the organism. Thus, any method which provides for effective introduction of a nucleic acid may be employed.

A. Plant Transformation

A nucleic acid comprising a polynucleotide of the present invention is optionally introduced into a plant. Generally, the polynucleotide will first be incorporated into a recombinant expression cassette or vector. Isolated nucleic acids of the present invention can be introduced into plants according to techniques known in the art. Techniques for transforming a wide variety of higher plant species are well known and described in the technical, scientific, and patent literature. See, for example, Weising et al., *Ann. Rev. Genet* 22: 421–477 (1988). For example, the DNA construct may be introduced directly into the genomic DNA of the plant cell using techniques such as electroporation, polyethylene glycol (PEG), poration, particle bombardment, silicon fiber delivery, or microinjection of plant cell protoplasts or embryogenic callus. See, e.g., Tomes, et al., Direct DNA Transfer into Intact Plant Cells Via Microprojectile Bombardment. pp.197–213 in Plant Cell, Tissue and Organ Culture, Fundamental Methods. eds. O. L. Gamborg and G. C. Phillips. Springer-Verlag Berlin Heidelberg New York, 1995; see, U.S. Pat. No. 5,990,387. The introduction of DNA constructs using PEG precipitation is described in Paszkowski et al., *Embo J.* 3: 2717–2722 (1984). Electroporation techniques are described in Fromm et al., *Proc. Natl. Acad. Sci. (USA)* 82: 5824 (1985). Ballistic transformation techniques are described in Klein et al., *Nature* 327: 70–73 (1987).

*Agrobacterium tumefaciens*-mediated transformation techniques are well described in the scientific literature. See, for example Horsch et al., *Science* 233: 496–498 (1984); Fraley et al., *Proc. Natl. Acad. Sci. (USA)* 80: 4803 (1983); and, *Plant Molecular Biology: A Laboratory Manual,* Chapter 8, Clark, Ed., Springer-Verlag, Berlin (1997). The DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616. Although Agrobacterium is useful primarily in dicots, certain monocots can be transformed by Agrobacterium. For instance, *Agrobacterium transformation* of maize is described in U.S. Pat. No. 5,550,318.

Other methods of transfection or transformation include (1) *Agrobacterium rhizogenes*-mediated transformation (see, e.g., Lichtenstein and Fuller In: Genetic Engineering, vol. 6, PWJ Rigby, Ed., London, Academic Press, 1987; and Lichtenstein, C. P., and Draper, J,. In: DNA Cloning, Vol. 11, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16 (2) liposome-mediated DNA uptake (see, e.g., Freeman et al., *Plant Cell Physiol.* 25: 1353 (1984)), (3) the vortexing method (see, e.g., Kindle, *Proc. Natl. Acad. Sci.*, (*USA*) 87:1228 (1990).

DNA can also be introduced into plants by direct DNA transfer into pollen as described by Zhou et al., Methods in Enzymology, 101:433 (1983); D. Hess, *Intern Rev. Cytol.*, 107:367 (1987); Luo et al., *Plant Mol. Biol. Reporter,* 6:165 (1988). Expression of polypeptide coding genes can be obtained by injection of the DNA into reproductive organs of a plant as described by Pena et al., *Nature,* 325.:274 (1987). DNA can also be injected directly into the cells of immature embryos and the rehydration of desiccated embryos as described by Neuhaus et al., *Theor. Appl. Genet.,* 75:30 (1987); and Benbrook et al., in *Proceedings Bio Expo* 1986, Butterworth, Stoneham, Mass., pp. 27–54 (1986). A variety of plant viruses that can be employed as vectors are known in the art and include cauliflower mosaic virus (CaMV), geminivirus, brome mosaic virus, and tobacco mosaic virus.

B. Transfection of Prokaryotes, Lower Eukaryotes, and Animal Cells

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology,* Dowden, Hutchinson and Ross, Inc. (1977).

Transgenic Plant Regeneration

Plant cells which directly result or are derived from the nucleic acid introduction techniques can be cultured to regenerate a whole plant which possesses the introduced genotype. Such regeneration techniques often rely on manipulation of certain phytohormones in a tissue culture growth medium. Plants cells can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture,* Macmillan Publishing Company, New York, pp.124–176 (1983); and Binding, *Regeneration of Plants, Plant Protoplasts,* CRC Press, Boca Raton, pp. 21–73 (1985).

The regeneration of plants from either single plant protoplasts or various explants is well known in the art. See, for example, *Methods for Plant Molecular Biology,* A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook,* Freeling and Walbot, Eds., Springer, New York (1994); *Corn and Corn Improvement,* $3^{rd}$ edition, Sprague and Dudley Eds., American Society of Agronomy, Madison, Wis. (1988). For transformation and regeneration of maize see, Gordon-Kamm et al., *The Plant Cell,* 2:603–618 (1990).

The regeneration of plants containing the polynucleotide of the present invention and introduced by Agrobacterium from leaf explants can be achieved as described by Horsch et al., *Science,* 227:1229–1231 (1985). In this procedure, transformants are grown in the presence of a selection agent and in a medium that induces the regeneration of shoots in the plant species being transformed as described by Fraley et al., *Proc. Natl. Acad. Sci. (U.S.A.),* 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype. Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences. Transgenic plants expressing a polynucleotide of the present invention can be screened for transmission of the nucleic acid of the present invention by, for example, standard immunoblot and DNA detection techniques. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated.

Modulating Polypeptide Levels and/or Composition

The present invention further provides a method for modulating or altering (i.e., increasing or decreasing) the concentration and/or ratio of the polypeptides of the present invention in a plant or part thereof. The method comprises introducing into a plant cell a recombinant expression cassette comprising a polynucleotide of the present invention as described above to obtain a transgenic plant cell, culturing the transgenic plant cell under transgenic plant cell growing conditions, and inducing or repressing expression of a polynucleotide of the present invention in the transgenic plant for a time sufficient to modulate concentration and/or the ratios of the polypeptides in the transgenic plant or plant part.

In some embodiments, the concentration and/or ratios of polypeptides of the present invention in a plant may be modulated by altering, in vivo or in vitro, the promoter of a gene to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., WO 93/22443. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or ratios of polypeptides of the present invention in the plant. Plant forming conditions are well known in the art and discussed briefly, supra.

In general, concentration or the ratios of the polypeptides is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In preferred embodiments, the polypeptides of the present invention are modulated in monocots, particularly maize.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, *Nucleic Acids Res.* 15:8125 (1987)) and the 7-methylguanosine cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)). Accordingly, the present invention provides 5' and/or 3' untranslated regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host such as to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12: 387–395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication No. WO 97/20078. See also, Zhang, J.-H., et al. *Proc. Natl. Acad. Sci. USA* 94:4504–4509 (1997). Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be a decreased $K_m$ and/or increased $K_{cat}$ over the wild-type protein as provided herein. In other embodiments, a protein or polynucleotide generated from sequence shuffling will have a ligand binding affinity greater than the non-shuffled wild-type polynucleotide. The increase in such properties can be at least 110%, 120%, 130%, 140% or at least 150% of the wild-type value.

Generic and Consensus Sequences

Polynucleotides and polypeptides of the present invention further include those having: (a) a generic sequence of at least two homologous polynucleotides or polypeptides, respectively, of the present invention; and, (b) a consensus sequence of at least three homologous polynucleotides or polypeptides, respectively, of the present invention. The generic sequence of the present invention comprises each species of polypeptide or polynucleotide embraced by the generic polypeptide or polynucleotide sequence, respectively. The individual species encompassed by a polynucleotide having an amino acid or nucleic acid consensus sequence can be used to generate antibodies or produce nucleic acid probes or primers to screen for homologs in other species, genera, families, orders, classes, phyla, or kingdoms. For example, a polynucleotide having a consensus sequence from a gene family of *Zea mays* can be used to generate antibody or nucleic acid probes or primers to other Gramineae species such as wheat, rice, or sorghum. Alternatively, a polynucleotide having a consensus sequence generated from orthologous genes can be used to identify or isolate orthologs of other taxa. Typically, a polynucleotide having a consensus sequence will be at least 9, 10, 15, 20, 25, 30, or 40 amino acids in length, or 20, 30, 40, 50, 100, or 150 nucleotides in length. As those of skill in the art are aware, a conservative amino acid substitution can be used for amino acids which differ amongst aligned sequence but are from the same conservative substitution group as discussed above. Optionally, no more than 1 or 2 conservative amino acids are substituted for each 10 amino acid length of consensus sequence.

Similar sequences used for generation of a consensus or generic sequence include any number and combination of allelic variants of the same gene, orthologous, or paralogous sequences as provided herein. Optionally, similar sequences used in generating a consensus or generic sequence are identified using the BLAST algorithm's smallest sum probability (P(N)). Various suppliers of sequence-analysis software are listed in chapter 7 of *Current Protocols in Molecular Biology*, F. M. Ausubel et al., Eds., Current Protocols, a joint venture between Greene Publishing Associates, Inc. and John Wiley & Sons, Inc. (Supplement 30). A polynucleotide sequence is considered similar to a reference sequence if the smallest sum probability in a comparison of the test nucleic acid to the reference nucleic acid is less than about 0.1, more preferably less than about 0.01, or 0.001, and most preferably less than about 0.0001, or 0.00001. Similar polynucleotides can be aligned and a consensus or generic sequence generated using multiple sequence alignment software available from a number of commercial suppliers such as the Genetics Computer Group's (Madison, Wis.) PILEUP software, Vector NTI's (North Bethesda, Md.) ALIGNX, or Genecode's (Ann Arbor, Mich.) SEQUENCHER. Conveniently, default parameters of such software can be used to generate consensus or generic sequences.

Machine Applications

The present invention provides processes for modeling or analyzing the polynucleotides and polypeptides of the present invention.

The present invention provides a process of identifying a candidate homologue (i.e., an ortholog or paralog) of a polynucleotide or polypeptide of the present invention. The process comprises entering sequence data of a polynucleotide or polypeptide of the present invention into a machine having a hardware or software sequence analysis system, developing data structures to facilitate access to the sequence data, manipulating the data to analyze the structure the polynucleotide or polypeptide, and displaying the results of the analysis. A candidate homologue has a statistically significant probability of having the same biological function (e.g., catalyzes the same reaction, binds to homologous proteins/nucleic acids, has a similar structural role) as the reference sequence to which it is compared. Accordingly, the polynucleotides and polypeptides of the present invention have utility in identifying homologs in animals or other plant species, particularly those in the family Gramineae such as, but not limited to, sorghum, wheat, or rice.

The process of the present invention comprises obtaining data representing a polynucleotide or polypeptide test sequence. Test sequences can be obtained from a nucleic acid of an animal or plant. Test sequences can be obtained directly or indirectly from sequence databases including, but not limited to, those such as: GenBank, EMBL, GenSeq, SWISS-PROT, or those available on-line via the UK Human Genome Mapping Project (HGMP) GenomeWeb. In some embodiments the test sequence is obtained from a plant species other than maize whose function is uncertain but will be compared to the test sequence to determine sequence similarity or sequence identity. The test sequence data is entered into a machine, such as a computer, containing: i) data representing a reference sequence and, ii) a hardware or software sequence comparison system to compare the reference and test sequence for sequence similarity or identity.

Exemplary sequence comparison systems are provided for in sequence analysis software such as those provided by the Genetics Computer Group (Madison, Wis.) or InforMax (Bethesda, Md.), or Intelligenetics (Mountain View, Calif.). Optionally, sequence comparison is established using the BLAST or GAP suite of programs. Generally, a smallest sum probability value (P(N)) of less than 0.1, or alternatively, less than 0.01, 0.001, 0.0001, or 0.00001 using the BLAST 2.0 suite of algorithms under default parameters identifies the test sequence as a candidate homologue (i.e., an allele, ortholog, or paralog) of the reference sequence. Those of skill in the art will recognize that a candidate homologue has an increased statistical probability of having the same or similar function as the gene/protein represented by the test sequence.

The reference sequence can be the sequence of a polypeptide or a polynucleotide of the present invention. The reference or test sequence is each optionally at least 25 amino acids or at least 100 nucleotides in length. The length of the reference or test sequences can be the length of the polynucleotide or polypeptide described, respectively, above in the sections entitled "Nucleic Acids" (particularly section (g)), and "Proteins". As those of skill in the art are aware, the greater the sequence identity/similarity between a reference sequence of known function and a test sequence, the greater the probability that the test sequence will have the same or similar function as the reference sequence. The results of the comparison between the test and reference sequences are outputted (e.g., displayed, printed, recorded) via any one of a number of output devices and/or media (e.g., computer monitor, hard copy, or computer readable medium).

Detection of Nucleic Acids

The present invention further provides methods for detecting a polynucleotide of the present invention in a nucleic acid sample suspected of containing a polynucleotide of the present invention, such as a plant cell lysate, particularly a lysate of maize. In some embodiments, a cognate gene of a polynucleotide of the present invention or portion thereof can be amplified prior to the step of contacting the nucleic acid sample with a polynucleotide of the present invention. The nucleic acid sample is contacted with the polynucleotide to form a hybridization complex. The polynucleotide hybridizes under stringent conditions to a gene encoding a polypeptide of the present invention. Formation of the hybridization complex is used to detect a gene encoding a polypeptide of the present invention in the nucleic acid sample. Those of skill will appreciate that an isolated nucleic acid comprising a polynucleotide of the present invention should lack cross-hybridizing sequences in common with non-target genes that would yield a false positive result. Detection of the hybridization complex can be achieved using any number of well-known methods. For example, the nucleic acid sample, or a portion thereof, may be assayed by hybridization formats including but not limited to, solution phase, solid phase, mixed phase, or in situ hybridization assays.

Detectable labels suitable for use in the present invention include any composition detectable by spectroscopic, radioisotopic, photochemical, biochemical, immunochemical, electrical, optical or chemical means. Useful labels in the present invention include biotin for staining with labeled streptavidin conjugate, magnetic beads, fluorescent dyes, radiolabels, enzymes, and colorimetric labels. Other labels include ligands which bind to antibodies labeled with fluorophores, chemiluminescent agents, and enzymes. Labeling the nucleic acids of the present invention is readily achieved such as by the use of labeled PCR primers.

Although the present invention has been described in some detail by way of illustration and example for purposes of clarity of understanding, it will be obvious that certain changes and modifications may be practiced within the scope of the appended claims.

EXAMPLE 1

This example describes the construction of a cDNA library.

Total RNA can be isolated from maize tissues with TRIzol Reagent (Life Technology Inc. Gaithersburg, Md.) using a modification of the guanidine isothiocyanate/acid-phenol procedure described by Chomczynski and Sacchi (Chomczynski, P., and Sacchi, N. *Anal. Biochem.* 162, 156 (1987)). In brief, plant tissue samples are pulverized in liquid nitrogen before the addition of the TRizol Reagent, and then further homogenized with a mortar and pestle. Addition of chloroform followed by centrifugation is conducted for separation of an aqueous phase and an organic phase. The total RNA is recovered by precipitation with isopropyl alcohol from the aqueous phase.

The selection of poly(A)+ RNA from total RNA can be performed using PolyATtract® system (Promega Corporation. Madison, Wis.). Biotinylated oligo(dT) primers are used to hybridize to the 3' poly(A) tails on mRNA. The hybrids are captured using streptavidin coupled to paramagnetic particles and a magnetic separation stand. The mRNA is then washed at high stringency conditions and eluted by RNase-free deionized water.

cDNA synthesis and construction of unidirectional cDNA libraries can be accomplished using the SuperScript Plasmid System (Life Technology Inc. Gaithersburg, Md.). The first strand of cDNA is synthesized by priming an oligo(dT) primer containing a Not I site. The reaction is catalyzed by SuperScript Reverse Transcriptase II at 45° C. The second strand of cDNA is labeled with alpha-$^{32}$P-dCTP and a portion of the reaction analyzed by agarose gel electrophoresis to determine cDNA sizes. cDNA molecules smaller than 500 base pairs and unligated adapters are removed by Sephacryl-S400 chromatography. The selected cDNA molecules are ligated into pSPORT1 vector in between of Not I and Sal I sites.

Alternatively, cDNA libraries can be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

EXAMPLE 2

This method describes construction of a full-length enriched cDNA library.

An enriched full-length cDNA library can be constructed using one of two variations of the method of Carninci et al. *Genomics* 37: 327–336, 1996. These variations are based on chemical introduction of a biotin group into the diol residue of the 5' cap structure of eukaryotic mRNA to select full-length first strand cDNA. The selection occurs by trapping the biotin residue at the cap sites using streptavidin-coated magnetic beads followed by RNase I treatment to eliminate incompletely synthesized cDNAs. Second strand cDNA is synthesized using established procedures such as those provided in Life Technologies' (Rockville, Md.) "SuperScript Plasmid System for cDNA Synthesis and Plasmid Cloning" kit. Libraries made by this method have been shown to contain 50% to 70% full-length cDNAs.

The first strand synthesis methods are detailed below. An asterisk denotes that the reagent was obtained from Life Technologies, Inc.

| A. First strand cDNA synthesis method 1 (with trehalose) | |
|---|---|
| mRNA (10 ug) | 25 µl |
| *Not I primer (5 ug) | 10 µl |
| *5 × 1$^{st}$ strand buffer | 43 µl |
| *0.1 m DTT | 20 µl |
| *dNTP mix 10 mm | 10 µl |
| BSA 10 ug/µl | 1 µl |
| Trehalose (saturated) | 59.2 µl |
| RNase inhibitor (Promega) | 1.8 µl |
| *Superscript II RT 200 u/µl | 20 µl |
| 100% glycerol | 18 µl |
| Water | 7 µl |

The mRNA and Not I primer are mixed and denatured at 65° C. for 10 min. They are then chilled on ice and other components added to the tube. Incubation is at 45° C. for 2 min. Twenty microliters of RT (reverse transcriptase) is added to the reaction and start program on the thermocycler (MJ Research, Waltham, Mass.):

| Step 1 | 45° C. 10 min |
|---|---|
| Step 2 | 45° C. −0.3° C./cycle, 2 seconds/cycle |
| Step 3 | go to 2 for 33 cycles |
| Step 4 | 35° C. 5 min |
| Step 5 | 45° C. 5 min |
| Step 6 | 45° C. 0.2° C./cycle, 1 sec/cycle |
| Step 7 | go to 7 for 49 cycles |
| Step 8 | 55° C. 0.1° C./cycle, 12 sec/cycle |
| Step 9 | go to 8 for 49 cycles |
| Step 10 | 55° C. 2 min |
| Step 11 | 60° C. 2 min |
| Step 12 | go to 11 for 9 times |
| Step 13 | 4° C. forever |
| Step 14 | end |

| B. First strand cDNA synthesis method 2 | |
|---|---|
| mRNA (10 µg) | 25 µl |
| water | 30 µl |
| *Not I adapter primer (5 µg) | 10 µl |
| 65° C. for 10 min, chill on ice, then add following reagents, | |
| *5x first buffer | 20 µl |
| *0.1M DTT | 10 µl |
| *10 mM dNTP mix | 5 µl |

Incubate at 45° C. for 2 min, then add 10 µl of *Superscript II RT (200 u/µl), start the following program:

| Step 1 | 45° C. for 6 sec, −0.1° C./cycle |
|---|---|
| Step 2 | go to 1 for 99 additional cycles |
| Step 3 | 35° C. for 5 min |
| Step 4 | 45° C. for 60 min |
| Step 5 | 50° C. for 10 min |
| Step 6 | 4° C. forever |
| Step 7 | end |

After the 1$^{st}$ strand cDNA synthesis, the DNA is extracted by phenol according to standard procedures, and then precipitated in NaOAc and ethanol, and stored in −20° C.

C. Oxidization of the Diol Group of mRNA for Biotin Labeling

First strand cDNA is spun down and washed once with 70% EtOH. The pellet resuspended in 23.2 µl of DEPC treated water and put on ice. Prepare 100 mM of NaIO4 freshly, and then add the following reagents:

| mRNA: 1$^{st}$ cDNA (start with 20 µg mRNA) | 46.4 µl |
|---|---|
| 100 mM NaIO4 (freshly made) | 2.5 µl |
| NaOAc 3M pH 4.5 | 1.1 µl |

To make 100 mM NaIO4, use 21.39 µg of NaIO4 for 1 µl of water. Wrap the tube in a foil and incubate on ice for 45 min. After the incubation, the reaction is then precipitated in:

| 5M NaCl | 10 µl |
|---|---|
| 20% SDS | 0.5 µl |
| isopropanol | 61 µl |

Incubate on ice for at least 30 min, then spin it down at max speed at 4° C. for 30 min and wash once with 70% ethanol and then 80% EtOH.

D. Biotinylation of the mRNA Diol Group

Resuspend the DNA in 110 µl DEPC treated water, then add the following reagents:

| 20% SDS | 5 µl |
|---|---|
| 2M NaOAc pH 6.1 | 5 µl |
| 10 mm biotin hydrazide (freshly made) | 300 µl |

Wrap in a foil and incubate at room temperature overnight.

E. RNase I Treatment

Precipitate DNA in:

| 5M NaCl | 10 µl |
|---|---|
| 2M NaOAc pH 6.1 | 75 µl |
| biotinylated mRNA:cDNA | 420 µl |
| 100% EtOH (2.5 Vol) | 1262.5 µl |

(Perform this precipitation in two tubes and split the 420 µl of DNA into 210 µl each, add 5 µl of 5 M NaCl, 37.5 µl of 2M NaOAc pH 6.1, and 631.25 µl of 100% EtOH). Store at −20° C. for at least 30 min. Spin the DNA down at 4° C. at maximal speed for 30 min. and wash with 80% EtOH twice, then dissolve DNA in 70 µl RNase free water. Pool two tubes and end up with 140 µl. Add the following reagents:

| RNase One 10 U/µl | 40 µl |
|---|---|
| 1$^{st}$ cDNA:RNA | 140 µl |
| 10X buffer | 20 µl |

Incubate at 37° C. for 15 min. Add 5 µl of 40 µg/µl yeast tRNA to each sample for capturing.

F. Full Length 1$^{st}$ cDNA Capturing

Blocking the beads with yeast tRNA:

| Beads | 1 ml |
|---|---|
| Yeast tRNA 40 µg/µl | 5 µl |

Incubate on ice for 30 min with mixing, wash 3 times with 1 ml of 2M NaCl, 50 mm EDTA, pH 8.0.

Resuspend the beads in 800 µl of 2M NaCl, 50 mm EDTA, pH 8.0, add RNase I treated sample 200 µl, and incubate the reaction for 30 min at room temperature. Capture the beads using the magnetic stand, save the supernatant, and start following washes:

2 washes with 2M NaCl, 50 mm EDTA, pH 8.0, 1 ml each time, 1 wash with 0.4% SDS, 50 µg/ml tRNA, 1 wash with 10 mm Tris-Cl pH 7.5, 0.2 mm EDTA, 10 mm NaCl, 20% glycerol, 1 wash with 50 µg/ml tRNA, 1 wash with 1$^{st}$ cDNA buffer G. Second strand cDNA synthesis Resuspend the beads in:

| *5X first buffer | 8 µl |
|---|---|
| *0.1 mM DTT | 4 µl |
| *10 mm dNTP mix | 8 µl |
| *5X 2nd buffer | 60 µl |
| *E. coli Ligase 10 U/µl | 2 µl |
| *E. coli DNA polymerase 10 U/µl | 8 µl |
| *E. coli RNaseH 2 U/µl | 2 µl |
| P32 dCTP 10 µci/µl | 2 µl |
| Or water up to 300 µl | 208 µl |

Incubate at 16° C. for 2 hr with mixing the reaction in every 30 min. Add 4 µl of T4 DNA polymerase and incubate for additional 5 min at 16° C.

Elute $_2$nd cDNA from the beads. Use a magnetic stand to separate the 2$^{nd}$ cDNA from the beads, then resuspend the beads in 200 µl of water, and then separate again, pool the samples (about 500 µl), Add 200 µl of water to the beads, then 200 µl of phenol:chloroform, vortex, and spin to separate the sample with phenol. Pool the DNA together (about 700 µl) and use phenol to clean the DNA again, DNA is then precipitated in 2 µg of glycogen and 0.5 vol of 7.5M NH4OAc and 2 vol of 100% EtOH. Precipitate overnight. Spin down the pellet and wash with 70% EtOH, air-dry the pellet.

| DNA | 250 µl | DNA | 200 µl |
|---|---|---|---|
| 7.5 M NH4OAc | 125 µl | 7.5 M NH4OAc | 100 µl |
| 100% EtOH | 750 µl | 100% EtOH | 600 µl |
| glycogen 1 µg/µl | 2 µl | glycogen 1 µg/µl | 2 µl |

H. Sal I Adapter Ligation

Resuspend the pellet in 26 µl of water and use 1 µl for TAE gel. Set up reaction as following:

| 2$^{nd}$ strand cDNA | 25 µl |
|---|---|
| *5X T4 DNA ligase buffer | 10 µl |
| *Sal I adapters | 10 µl |
| *T4 DNA ligase | 5 µl |

Mix gently, incubate the reaction at 16° C. overnight. Add 2 µl of ligase second day and incubate at room temperature for 2 hrs (optional). Add 50 µl water to the reaction and use 100 µl of phenol to clean the DNA, 90 µl of the upper phase is transferred into a new tube and precipitate in:

| Glycogen 1 µg/µl | 2 µl |
|---|---|
| Upper phase DNA | 90 µl |
| 7.5 M NH4OAc | 50 µl |
| 100% EtOH | 300 µl | precipitate at −20° C. overnight Spin down the pellet at 4° C. and wash in 70% EtOH, dry the pellet.

I. Not I digestion

| 2$^{nd}$ cDNA | 41 µl |
|---|---|
| *Reaction 3 buffer | 5 µl |
| *Not I 15 u/µl | 4 µl |

Mix gently and incubate the reaction at 37° C. for 2 hr. Add 50 µl of water and 100 µl of phenol, vortex, and take 90 µl of the upper phase to a new tube, then add 50 µl of NH4OAc and 300 µl of EtOH. Precipitate overnight at −20° C.

Cloning, ligation, and transformation are performed per the SuperScript cDNA synthesis kit. (Life Technology Inc. Gaithersburg, Md.)

EXAMPLE 3

This example describes cDNA sequencing and library subtraction.

Individual colonies can be picked and DNA prepared either by PCR with M13 forward primers and M13 reverse primers, or by plasmid isolation. cDNA clones can be sequenced using M13 reverse primers.

cDNA libraries are plated out on 22×22 cm$^2$ agar plate at density of about 3,000 colonies per plate. The plates are incubated in a 37° C. incubator for 12–24 hours. Colonies are picked into 384-well plates by a robot colony picker, Q-bot (GENETIX Limited). These plates are incubated overnight at 37° C. Once sufficient colonies are picked, they are pinned onto 22×22 cm$^2$ nylon membranes using Q-bot. Each membrane holds 9,216 or 36,864 colonies. These membranes are placed onto an agar plate with an appropriate antibiotic. The plates are incubated at 37° C. overnight.

After colonies are recovered on the second day, these filters are placed on filter paper prewetted with denaturing solution for four minutes, then incubated on top of a boiling water bath for an additional four minutes. The filters are then placed on filter paper prewetted with neutralizing solution for four minutes. After excess solution is removed by placing the filters on dry filter papers for one minute, the colony side of the filters is placed into Proteinase K solution, incubated at 37° C. for 40–50 minutes. The filters are placed on dry filter papers to dry overnight. DNA is then crosslinked to nylon membrane by UV light treatment.

Colony hybridization is conducted as described by Sambrook, J., Fritsch, E. F. and Maniatis, T., (in Molecular Cloning: A laboratory Manual, $2^{nd}$ Edition). The following probes can be used in colony hybridization:

1. First strand cDNA from the same tissue as the library was made from to remove the most redundant clones.
2. 48–192 most redundant cDNA clones from the same library based on previous sequencing data.
3. 192 most redundant cDNA clones in the entire maize sequence database.
4. A Sal-A20 oligo nucleotide of SEQ ID NO: 3 TCG ACC CAC GCG TCC GAA AAA AAA AAA AAA AAA AAA, removes clones containing a poly A tail but no cDNA.
5. cDNA clones derived from rRNA.

The image of the autoradiography is scanned into computer and the signal intensity and cold colony addresses of each colony is analyzed. Re-arraying of cold-colonies from 384 well plates to 96 well plates is conducted using Q-bot.

EXAMPLE 4

This example describes identification of the gene from a computer homology search.

Gene identities can be determined by conducting BLAST (Basic Local Alignment Search Tool; Altschul, S. F., et al., (1993) J. Mol. Biol. 215:403–410; see also the World Wide Web at ncbi.nlm.nih.gov/BLAST/) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences are analyzed for similarity to all publicly available DNA sequences contained in the "nr" database using the BLASTN algorithm. The DNA sequences are translated in all reading frames and compared for similarity to all publicly available protein sequences contained in the "nr" database using the BLASTX algorithm (Gish, W. and States, D. J. *Nature Genetics* 3:266–272 (1993)) provided by the NCBI. In some cases, the sequencing data from two or more clones containing overlapping segments of DNA are used to construct contiguous DNA sequences.

Sequence alignments and percent identity calculations can be performed using the Megalign program of the LASERGENE bioinformatics computing suite (DNASTAR Inc., Madison, Wis.). Multiple alignment of the sequences can be performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method are KTUPLE 1, GAP PENALTY=3, WINDOW=5 and DIAGONALS SAVED=5.

EXAMPLE 5

This example describes expression of transgenes in monocot cells.

A transgene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue; Stratagene). Bacterial transformants can be screened by restriction enzyme digestion of plasmid DNA and limited nucleotide sequence analysis using the dideoxy chain termination method (Sequenase DNA Sequencing Kit; U.S. Biochemical). The resulting plasmid construct would comprise a transgene encoding, in the 5' to 3' direction, the maize 27 kD zein promoter, a cDNA fragment encoding the instant polypeptides, and the 10 kD zein 3' region.

The transgene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (Hoechst Ag, Frankfurt, Germany) or equivalent may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton flying disc (Bio-Rad Labs). The particles are then accelerated into the corn tissue with a Biolistic PDS-1000/He (Bio-Rad Instruments, Hercules, Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains glufosinate (2 mg per liter) and lacks casein or proline. The tissue continues to grow slowly on this medium. After an additional 2 weeks the tissue can be transferred to fresh N6 medium containing glufosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

EXAMPLE 6

This example describes expression of transgenes in dicot cells.

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), SmaI, KpnI and XbaI. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A Du Pont Biolistic PDS1000/HE instrument (helium retrofit) can be used for these transformations.

A selectable marker gene which can be used to facilitate soybean transformation is a transgene composed of the 35S promoter from Cauliflower Mosaic Virus (Odell et a/.(1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL $CaCl_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 7

This example describes expression of a transgene in microbial cells.

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG low melting agarose gel (FMC). Buffer and agarose contain 10 µg/ml ethidium bromide for visualization of the DNA fragment. The fragment can then be purified from the agarose gel by digestion with GELase (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21 (DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One microgram of protein from the soluble fraction of the culture can be separated by SDS-polyacrylamide gel electrophoresis. Gels can be observed for protein bands migrating at the expected molecular weight.

EXAMPLE 8

Determination of Effect of Mutator (Mu) Insertion into Sus1 Gene

This example describes the procedure to identify plants containing Mu inserted into constitutive sucrose synthase gene, and phenotypic and biochemical analyses of the mutant plants.

The Trait Utility System for Corn (TUSC; see U.S. Pat. No. 5,962,764) is a method that employs genetic and molecular techniques to facilitate the study of gene function in maize. Studying gene function implies that the gene's sequence is already known, thus the method works in reverse: from sequence to phenotype. This kind of application is referred to as "reverse genetics", which contrasts with "forward" methods (such as transposon tagging) that are designed to identify and isolate the gene(s) responsible for a particular trait (phenotype).

Pioneer Hi-Bred International, Inc., has a proprietary collection of maize genomic DNA from approximately 42,000 individual F. plants (Reverse genetics for maize., Meeley, R and Briggs, S, 1995, Maize Genet. Coop. Newslett. 69:67,82). The genome of each of these individuals contains multiple copies of the transposable element family, Mutator (Mu). The Mu family is highly mutagenic; in the presence of the active element Mu-DR, these elements transpose throughout the genome, inserting into genic regions, and often disrupting gene function. By collecting genomic DNA from a large number of individuals, Pioneer has assembled a library of the mutagenized maize genome. Mu insertion events are predominately heterozygous so, given the recessive nature of most insertional mutations, the $F_1$ plants appear wild-type. Each of the plants was selfed to produce $F_2$ seed, which was collected. In generating the $F_2$ progeny, insertional mutations segregate in a Mendelian fashion so are useful for investigating a mutant allele's effect on the phenotype. The TUSC system has been successfully used by a number of laboratories to identify the function of a variety of genes (Cloning and characterization of the maize An1 gene, Bensen, R. J. et al., 1995, Plant Cell 7:75–84; Diversification of C-function activity in maize flower development, Mena, M. et al., 1996, Science 274:1537–1540; Analysis of a chemical plant defense mechanism in grasses, Frey, M. et al., 1997, Science 277:696–699; The control of maize spikelet meristem fate by the APETALA2-like gene Indeterminate spikelet 1, Chuck, G., et al., 1998, Genes & Development 12:1145–1154; A SecY homologue is required for the elaboration of the chloroplast thylakoid membrane and for normal chloroplast gene expression, Roy, L. M. et al., 1998, J. Cell Biol. 141:1–11).

PCR Screening for Mu insertions in Sus1:

Two primers were designed from within the Sus1 cDNA and designated as gene-specific primers (GSPs):

```
Forward primer (GSP1) of SEQ ID NO:8:  5'-ACGGAATCGTTCGCAAGTGGATCTC-3'

Reverse primer (GSP2) of SEQ ID NO:9:  5'-GATGATTGGCTTGTTCCTGTCGTTC-3'
```

These primers are about 1 kb apart with respect to the genomic sequence of Sus1.

Mu TIR primer of SEQ ID NO:10

5'-AGA GM GCC MC GCC AWC GCC TCY ATT TCG TC-3'

To select primers for PCR we used Pickoligo. This program chooses the $T_m$ according to the following equation:

$$Tm=[((GC*3+AT*2)*37-562)/\text{length}]-5$$

PCR reactions were run with an annealing temperature of 62 C and a thermocycling profile as follows:

```
          94 °C. - 2' (initial (denaturation)

/  94 °C. - 30"-1'
35 cycles 62 °C. - 30"-2'
       \  72 °C. - 1-3'
          ─────────────
          72 °C. - 5'    (final extension)
```

Gel electrophoresis of the PCR products confirmed that there was no false priming in single primer reactions and that only one fragment was amplified in paired GSP reactions.

The genomic DNA from 42,000 plants, combined into pools of 48 plants each, was subjected to PCR with either GSP1 or GSP2 and Mu TIR. The pools that were confirmed to be positive by dot-blot hybridization using Sus1 cDNA as a probe were subjected to gel-blot analysis in order to determine the size of fragments amplified. The pools in which clean fragments were identified were subjected to further analysis to identify the individual plants within those pools that contained Mu insertion(s).

Figure 6:
FIG. 6. In this representation of the genomic clone of ZmSus1, narrow bars represent introns and wider bars represent exons. Approximate location of the two independent Mu-insertional alleles is shown by the down arrows in the 12$^{th}$ exon (exact location is in the signature sequences shown above).

Seed from $F_1$ plants identified in this manner was planted in the field. Leaf discs from twenty plants from each $F_2$ row were collected and genomic DNA isolated. The same twenty plants were selfed and the $F_3$ seed saved. Pooled DNA (from 20 plants) from each of the twelve rows was subjected to PCR using GSP1 or GSP2 and Mu TIR primer as mentioned above. Three pools identified to contain Mu insertions were subjected to individual plant analysis and homozygotes identified. The PCR-amplified fragments were cloned into TOPO vector (Invitrogen) and sequenced. The Mu insertion sites were determined by comparing the sequences obtained with the Sus1 and Mu sequences and are presented in FIG. 6, along with the surrounding signature sequences. Both the insertions are within 3 nucleotides of each other in the open reading frame corresponding to the $12^{th}$ exon, suggesting that this region in the gene might represent a hot spot for Mu insertion.

From the stalks of homozygous mutant plants and their wildtype sibs, two internodes subtending the ear node were collected about two weeks before final harvest. Cellulose and lignin concentrations were determined on the ground samples from the dried internodes. The concentration of cellulose is 30% less in the mutant plants than in their wild-type sibs when considered as a percentage of total dry matter, and 6% less as a percentage of structural dry matter (FIG. 7). Significant reduction is also observed for structural dry matter in the mutant plants. This is consistent with the hypothesis that UDP-glucose derived from the action of sucrose synthase plays a significant role in cellulose biosynthesis. It also appears that a reduction in cellulose production adversely affects cell wall formation.

EXAMPLE 9

Alignment of Sucrose Synthase Amino Acid Sequences Including that of SUS3

Alignment was performed using AlignX program from Vector NTI. SH1 and SUS1 are about 80% identical and about 90% similar. SUS3 is about 70% identical and 80% similar to both SH1 and SUS1 (see FIG. 8). Sufficient differences exist with respect to both SH1 and SUS1 as to classify SUS3 as a different protein. Since the short arm of chromosome 1 is considered to be a duplication of the long arm of chromosome 9, the map location of Sus3 (bin 1.04) implies that it might be ancestrally related to Sus1 (map location 9.05). However, based on homology analysis, it appears to have evolved independently of Sh1 and Sus1. Like evolution of sucrose synthase genes apparently is chromosome-dependent, as Sh1 and Sus1, both on chromosome 9, share significantly greater similarity than does either of these with Sus3, although Sus3 is apparently a duplication of Sus1.

SUS3 in SEQ ID NO 1 appears to be missing 5–10 amino acids at the N-terminal end. Predicted molecular mass of the slightly truncated SUS3, 802 amino acids long, is 91 kDa. The molecular mass might be adjusted 0.5–1 kDa upward once the full-length cDNA is isolated. The predicted molecular masses of SH1 and SUS1 are 91.7 and 92.8 kDa, respectively. Respective isoelectric points (pI) of SUS3, SH1, and SUS1 are: 6.07, 5.96, and 6.04.

EXAMPLE 10

Multiple Alignment of Maize Sucrose Synthase Polynucleotides Including that of ZmSus3

The alignment was performed using the AlignX program of the Vector NTI suite. Sh1 and Sus1 are 67% similar; either of these genes is about 60% similar to Sus3 (see FIG. 9). A similar trend was observed at the amino acid sequence level (see FIG. 8 and Example 9).

EXAMPLE 11

Polynucleotide and Polypeptide Encoding Deduced Full Length Sus3 using SEQ ID NO: 1 and Sorghum Sequence (SEQ ID NO: 13) for Completion of N-Terminal End Sequencing of a complete full length native Zea mays cDNA which encodes for the full length Sus3 has not been possible to date due to the low expression level of Sus3 in maize and corresponding low representation in maize cDNA libraries. However, a sorghum EST of about 345 nucleotides, GenBank Accession No. BF481989 (SEQ ID NO: 13), shows a high level of homology at the 3' end to the 5' end of SEQ ID NO.1. By aligning SEQ ID NO: 1 and SEQ ID NO: 13 (FIG. 10 and FIG. 11), it was possible to locate the ATG encoding the first methionine in SEQ ID NO: 13 and determine an open reading frame through and into the aligned SEQ ID NO: 1. The inclusion of this short segment of sorghum sequence from SEQ ID NO: 13 with the predominantly full length cDNA sequence of Sus3 of SEQ ID NO: 1 provides the deduced full length polynucleotide of the Sus3 (SEQ ID NO: 11) which encodes the full length Sus3 polypeptide (SEQ ID NO: 12). Thus this sorghum-maize hybrid sequence was used to supply the deduced N-terminal end of the deduced full length Sus3 protein (SEQ ID NO: 12).

EXAMPLE 12

Determination of Polynucleotide Encoding Full Length Zea mays Sus3 using Genomic DNA Sequencing of a complete full length native Zea mays Sus3 can be accomplished by using SEQ ID NO. 11 or SEQ ID NO: 13 to identify for isolation the fragment of genomic Zea mays DNA encoding untranslated region and 5' end of the Zea mays Sus3 gene. This isolated genomic fragment is then sequences and the exons identified to verify the maize Sus3 cDNA sequence.

The above examples are provided to illustrate the invention but not to limit its scope. Other variants of the invention will be readily apparent to one of ordinary skill in the art and are encompassed by the appended claims. All publications, patents, patent applications, and computer programs cited are hereby incorporated by reference.

What is claimed is:

1. An isolated polynucleotide which encodes a polypeptide with sucrose synthase activity comprising a member selected from the group consisting of:
   (a) polynucleotide encoding the polypeptide of SEQ ID NO: 2 or SEQ ID NO: 12; and,
   (b) the polynucleotide of SEQ ID NO: 1 or SEQ ID NO: 11.

2. A recombinant expression cassette, comprising the polynucleotide of claim 1 operably linked to a promoter.

3. A host cell comprising the recombinant expression cassette of claim 2.

4. A transgenic plant comprising the recombinant expression cassette of claim 2.

5. The tranagenic plant of claim 4, wherein said plant is a monocot.

6. The transgenic plant of claim 4, wherein said plant is a dicot.

7. The tranagenic plant of claim 4, wherein said plant is selected from the group consisting of: maize, soybean, sunflower, sorghum, canola, wheat, alfalfa, cotton, rice, barley, millet, peanut, and cocoa.

8. A transgenic seed from the transgenic plant of claim 4.

* * * * *